(12) United States Patent
Masaki et al.

(10) Patent No.: US 9,856,250 B2
(45) Date of Patent: Jan. 2, 2018

(54) SUBSTITUTED TROPANE DERIVATIVES

(71) Applicant: TOA EIYO LTD., Chuo-ku (JP)

(72) Inventors: Hidekazu Masaki, Saitama (JP); Yoichi Iwasaki, Okegawa (JP); Masayuki Kageyama, Kawaguchi (JP); Yujiro Uchino, Saitama (JP)

(73) Assignee: TOA EIYO LTD., Chuo-ku (JP)

( * ) Notice: Subject to any disclaimer, the term of this patent is extended or adjusted under 35 U.S.C. 154(b) by 0 days.

(21) Appl. No.: 15/314,020

(22) PCT Filed: May 28, 2015

(86) PCT No.: PCT/JP2015/065471
§ 371 (c)(1),
(2) Date: Nov. 25, 2016

(87) PCT Pub. No.: WO2015/182724
PCT Pub. Date: Dec. 3, 2015

(65) Prior Publication Data
US 2017/0190699 A1 Jul. 6, 2017

(30) Foreign Application Priority Data
May 28, 2014 (JP) .................. 2014-109847

(51) Int. Cl.
*C07D 451/02* (2006.01)
*C07D 519/00* (2006.01)
*A61K 31/439* (2006.01)

(52) U.S. Cl.
CPC ......... *C07D 451/02* (2013.01); *C07D 519/00* (2013.01)

(58) Field of Classification Search
CPC .................... C07D 451/02; C07D 519/00
See application file for complete search history.

(56) References Cited

U.S. PATENT DOCUMENTS

| 5,070,094 A | 12/1991 | Fowler |
| 2005/0197351 A1 | 9/2005 | Lee et al. |
| 2011/0136833 A1 | 6/2011 | Mikamiyama et al. |
| 2013/0065898 A1 | 3/2013 | Masaki et al. |
| 2013/0150377 A1 | 6/2013 | Mikamiyama et al. |
| 2014/0038941 A1 | 2/2014 | Sawada et al. |

FOREIGN PATENT DOCUMENTS

| CA | 2449249 A1 * | 12/2002 | ............. A61K 31/44 |
| CN | 101351465 A | 1/2009 | |
| CN | 102015658 A | 4/2011 | |
| CN | 102906074 A | 1/2013 | |
| FR | 2 789 681 A1 | 8/2000 | |
| JP | 3-167184 A | 7/1991 | |
| JP | 7-503463 A | 4/1995 | |
| JP | 2005-239708 A | 9/2005 | |
| JP | 2008-533020 A | 8/2008 | |
| JP | 2008-546800 A | 12/2008 | |
| JP | 2009-500340 A | 1/2009 | |
| JP | 2009-521461 A | 6/2009 | |
| JP | 2009-521471 A | 6/2009 | |
| JP | 2009-534320 A | 9/2009 | |
| JP | 2011-529884 A | 12/2011 | |
| WF | 2009/146539 A1 | 12/2009 | |
| WO | 93/15073 A1 | 8/1993 | |
| WO | 2006/098969 A2 | 9/2006 | |

(Continued)

OTHER PUBLICATIONS

Dziegielewska, B., "T-type calcium channels blockers as new tools in cancer therapies." Pflügers Archiv—European Journal of Physiology 466.4 (2014): 801-810.*

Liu, J.K.H., "Anti-Cancer Vaccines—A One-Hit Wonder?." The Yale journal of biology and medicine 87.4 (2014): 481.*

International Search Report dated Aug. 25, 2015 in PCT/JP2015/065471 filed May 23, 2015.

Edward Perez-Reyes, "Molecular Physiology of Low-Voltage-Activated T-type Calcium Channels", Physiological Reviews, 2003, vol. 83, No. 1, 46 pages.

Lloyd S. Gray et al., "The pharmacology and regulation of T type calcium channels: New opportunities for unique therapeutics for cancer", Cell Calcium, 2006, vol. 40, No. 2, pp. 115-120.

(Continued)

*Primary Examiner* — John M Mauro
(74) *Attorney, Agent, or Firm* — Oblon, McClelland, Maier & Neustadt, L.L.P.

(57) ABSTRACT

Provided is a compound which is useful as a prophylactic or therapeutic agent for various diseases in which T-type calcium channels are involved, such as hypertension, arrhythmia, pain and cancers, the compound having antagonistic activity against T-type calcium channels, being highly stable in the body and having low risk of, for example, genotoxicity. Disclosed is a compound represented by the following general formula (I), a pharmaceutically acceptable salt thereof, or a solvate thereof:

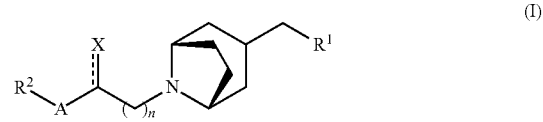

(I)

wherein $R^1$ represents —NH(C=O)—V—$R^3$ or —(C=O)NH—V—$R^3$;

V represents a single bond, methylene, or —C(CH$_3$)$_2$O—;

$R^2$ represents a optionally substituted C$_{1-6}$ alkyl group;

X represents a hydrogen atom, an oxygen atom, a hydroxyl group, a methyl group, or a methylene group;

A represents —NR$^6$—, —O—CH$_2$—, or —S—CH$_2$—;

n represents the number of methylene chains and represents an integer of 0, 1 or 2; and a doublet containing a dotted line represents a single bond or a double bond.

13 Claims, No Drawings

(56) References Cited

FOREIGN PATENT DOCUMENTS

| WO | 2007/002361 A2 | 1/2007 |
|---|---|---|
| WO | 2007/002884 A2 | 1/2007 |
| WO | 2007/073497 A2 | 6/2007 |
| WO | 2007/075852 A2 | 7/2007 |
| WO | 2007/118323 A1 | 10/2007 |
| WO | 2007/120729 A2 | 10/2007 |
| WO | 2008/133867 A1 | 11/2008 |
| WO | 2009/132454 A1 | 11/2009 |
| WO | 2011/026240 A1 | 3/2011 |
| WO | 2011/148956 A1 | 12/2011 |
| WO | 2012/105594 A1 | 8/2012 |
| WO | 2013/148640 A1 | 10/2013 |

OTHER PUBLICATIONS

Jean Chemin et al., "Molecular pathways underlying the modulation of T-type calcium channels by neurotransmitters and hormones", Cell Calcium, 2006, vol. 40, No. 2, pp. 121-134.

Paul A. Heppenstall et al., "A role for T-type $Ca^{2+}$ channels in mechanosensation", Cell Calcium, 2006, vol. 40, No. 2, pp. 165-174.

Vincenzo Crunelli et al., "Thalamic T-type $Ca^{2+}$ channels and NREM sleep", Cell Calcium, 2006, vol. 40, No. 2, pp. 175-190.

Hee-Sup Shin, "T-type $Ca^{2+}$ channels and absence epilepsy", Cell Calcium, 2006, vol. 40, No. 2, pp. 191-196.

Vesna Jevtovic-Todorovic et al., "The role of peripheral T-type calcium channels in pain transmission", Cell Calcium, 2006, vol. 40, No. 2, pp. 197-203.

Guy Vassort et al., "Role of T-type $Ca^{2+}$ channels in the heart", Cell Calcium, 2006, vol. 40, No. 2, pp. 205-220.

Alberto Darszon et al., "T-type $Ca^{2+}$ channels in sperm function", Cell Calcium, 2006, vol. 40, No. 2, pp. 241-252.

Samir Fareh et al., "The T-Type $Ca^{2+}$ Channel Blocker Mibefradil Prevents the Development of a Substrate for Atrial Fibrillation by Tachycardia-Induced Atrial Remodeling in Dogs", Circulation, 1999, vol. 100, No. 21, 8 pages.

Habib Karam et al., "Contrasting Effects of Selective T- and L-Type Calcium Channel Blockade on Giomerular Damage in DOCA Hypertensive Rats", Hypertension, 1999, vol. 34, 7 pages.

Samir Fareh et al., "Differential efficacy of L- and T-type calcium channel blockers in preventing tachycardia-induced atrial remodeling in dogs", Cardiovascular Research, 2001, vol. 49, pp. 762-770.

Nathalie Lalevee et al., "Aldosterone increases T-type calcium channel expression and in vitro beating frequency in neonatal rat cardiomyocytes", Cardiovascular Research, 2005, vol. 67, pp. 216-224.

Narutaka Ohashi et al., "Development of Newer Calcium Channel Antagonists", Drugs, 2009, vol. 69, No. 1, pp. 21-30.

James T. Taylor et al., "Selective blockade of T-type $Ca^{2+}$ channels suppresses human breast cancer cell proliferation", Cancer Letters, 2008, vol. 267, No. 1, pp. 116-124.

Matthew E. Barton et al., "The antihyperalgesic effects of the T-type calcium channel blockers ethosuximide, trimethadione, and mibefradil", European Journal of Pharmacology, 2005, vol. 521, pp. 79-85.

Combined Chinese Office Action and Search Report dated Jul. 27, 2017 in Patent Application No. 201580028221.2 (with English Translation and English Translation of Category of Cited Documents).

\* cited by examiner

SUBSTITUTED TROPANE DERIVATIVES

FIELD OF THE INVENTION

The present invention relates to a substituted tropane derivative having antagonistic activity against T-type calcium channels, and a pharmaceutical agent containing the same.

BACKGROUND OF THE INVENTION

Intracellular calcium is an important factor which induces various physiological responses such as neuronal excitement, muscle contraction, hormone secretion, fertilization, immune response, cell motility, and cell death. The concentration of intracellular calcium is regulated by means of ion channels or pumps, such as voltage-dependent calcium channels and receptor-operated calcium channels. Voltage-dependent calcium channel is a calcium channel that is opened and closed depending on the change in the potential difference between inside and outside of a cell, and exist on the cellular membranes of muscle cells or nerve cells. The voltage-dependent calcium channels are currently classified into L-type, T-type, N-type, P/Q-type and R-type calcium channels, based on electrophysiological characteristics and pharmacological characteristics. Unlike the L-type, N-type, P/Q-type and R-type calcium channels that are classified as medium potential- and high potential-activated calcium channels in view of the membrane potential activation threshold, the T-type calcium channels are activated at a potential close to the resting membrane potential. Therefore, the T-type calcium channels are considered to function as a trigger for an influx of calcium into the cell, and to participate in the pacemaker activity, production of low-threshold calcium spikes, and burst firing.

T-type calcium channels include three subtypes, i.e. Cav3.1 ($\alpha$1G), Cav3.2 ($\alpha$1H) and Cav3.3 ($\alpha$1I), and expression of the channels in, for example, the brain, nerve tissues, heart, kidneys, liver, pancreas, smooth muscles and testicles, has been reported. It has been suggested that T-type calcium channels are responsible for physiological functions such as the pacemaker function of the heart, renovascular tonus, hormone secretion, nerve firing and pain transmission, and activation of the T-type calcium channels relates to the onset and progress of various pathological conditions such as hypertension, tachyarrhythmia including atrial fibrillation, cardiac hypertrophy, cardiac failure, renal dysfunction, pain, epilepsy, sleep disorder, obesity, and cancers. Therefore, T-type calcium channel antagonist is believed to be an effective drug for the treatment or prevention of these diseases (Non Patent Documents 1 to 16).

Known examples of the T-type calcium channel antagonists include efonidipine and mibefradil, as well as 3,4-dihydroquinazoline derivatives disclosed in Patent Document 1, quinazoline derivatives disclosed in Patent Document 2, pyridylamide derivatives disclosed in Patent Document 3, indole derivatives disclosed in Patent Document 4, thiazole derivatives disclosed in Patent Documents 5 and 6, aisoxazole derivatives disclosed in Patent Document 7, and imidazopyridine derivatives disclosed in Patent Document 8.

Furthermore, regarding T-type calcium channel antagonists having a nitrogen-containing non-aromatic ring as a common mother nucleus, Patent Document 9 discloses N-piperidinylacetamide derivativeS, Patent Documents 10 and 11 disclose 3-fluoropiperidine derivatives, Patent Document 12 discloses imidazoylmethylpiperidine derivatives, Patent Document 13 discloses piperazine derivatives, and Patent Document 14 discloses oxopiperazine derivatives, as the T-type calcium channel antagonists.

CITATION LIST

Patent Documents

Patent Document 1: JP 2005-239708 A
Patent Document 2: JP 2008-533020 A
Patent Document 3: JP 2009-534320 A
Patent Document 4: WO 2008/133867 A
Patent Document 5: JP 2009-521461 A
Patent Document 6: JP 2009-521471 A
Patent Document 7: WO 2007/118323 A
Patent Document 8: WO 2012/105594 A
Patent Document 9: WO 2009/146539 A
Patent Document 10: JP 2008-546800 A
Patent Document 11: JP 2009-500340 A
Patent Document 12: WO 2013-148640 A
Patent Document 13: WO 2009-132454 A
Patent Document 14: WO 2011-026240 A

Non Patent Document

Non Patent Document 1: Physiological Reviews, Vol. 83, No. 1, p. 117-161 (2003)
Non Patent Document 2: Cell Calcium, Vol. 40, No. 2, p. 115-120 (2006)
Non Patent Document 3: Cell Calcium, Vol. 40, No. 2, p. 121-134 (2006)
Non Patent Document 4: Cell Calcium, Vol. 40, No. 2, p. 165-174 (2006)
Non Patent Document 5: Cell Calcium, Vol. 40, No. 2, p. 175-190 (2006)
Non Patent Document 6: Cell Calcium, Vol. 40, No. 2, p. 191-196 (2006)
Non Patent Document 7: Cell Calcium, Vol. 40, No. 2, p. 197-203 (2006)
Non Patent Document 8: Cell Calcium, Vol. 40, No. 2, p. 205-220 (2006)
Non Patent Document 9: Cell Calcium, Vol. 40, No. 2, p. 241-252 (2006)
Non Patent Document 10: Circulation, Vol. 100, No. 21, p. 2191-2197 (1999)
Non Patent Document 11: Hypertension, Vol. 34, p. 673-678 (1999)
Non Patent Document 12: Cardiovascular Research, Vol. 49, p. 762-770 (2001)
Non Patent Document 13: Cardiovascular Research, Vol. 67, p. 216-224 (2005)
Non Patent Document 14: Drugs, Vol. 69, No. 1, p. 21-30 (2009)
Non Patent Document 15: Cancer Letters, Vol. 267, No. 1, p. 116-124 (2008)
Non Patent Document 16: European Journal of Pharmacology, p. 79-85 (2005)

SUMMARY OF THE INVENTION

Problems to be Solved by the Invention

An object of the present invention is to provide compounds that is useful as prophylactic or therapeutic agents for various diseases in which T-type calcium channels are involved, such as hypertension, arrhythmia, pain and cancer, which show antagonistic activity against T-type calcium channels, which are highly stable in the body, and the risk of, for example, genotoxicity, is low from which.

Means for Solving the Problems

The inventors of the present invention have analyzed compounds showing antagonistic activity against T-type calcium channels, and the inventors have found that a certain compounds of T-type calcium channel antagonists having piperidine structures exhibit genotoxic risk such as mutagenicity, which may cause safety problem. Thus, the inventors of the present invention synthesized and examined a variety of compounds for searching compounds showing superior antagonistic activity against T-type calcium channels and superior safety, and found that certain substituted tropane derivatives show excellent antagonistic activity against T-type calcium channels and are highly safe with low risk of genotoxicity. Thus, the inventors completed the present invention.

The present invention provides the following [1] to [6].

[1] A compound represented by the following general formula (I), a pharmaceutically acceptable salt thereof, or a solvate thereof:

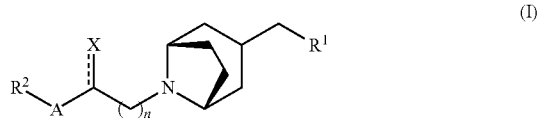

(I)

wherein $R^1$ represents —NH(C=O)—V—$R^3$, —(C=O)NH—V—$R^3$, or the following formula:

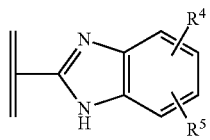

wherein V represents a single bond, methylene, or —C(CH$_3$)$_2$O—;

$R^3$ represents an optionally substituted C$_{3-6}$ alkyl group, a crosslinked cyclic hydrocarbon group, a fused polycyclic hydrocarbon group, an optionally substituted aryl group, or an optionally substituted heterocyclic group;

$R^4$ and $R^5$ may be the same or different and independently represent a hydrogen atom, a halogen atom, a cyano group, an optionally substituted C$_{1-6}$ alkyl group, or an optionally substituted C$_{1-6}$ alkoxy group, or $R^4$ and $R^5$ may be linked together and form an optionally substituted non-aromatic heterocyclic ring;

$R^2$ represents an acyl group, an optionally substituted C$_{1-6}$ alkyl group, an optionally substituted aryl group, or an optionally substituted heterocyclic group;

X represents a hydrogen atom, an oxygen atom, a hydroxyl group, a methyl group, or a methylene group;

A represents —NR$^6$—, —NHCONH—, —O—CH$_2$—, or —S—CH$_2$—;

$R^6$ represents a hydrogen atom or an optionally substituted C$_{1-6}$ alkyl group, or $R^6$ and $R^2$ may be linked together and form an optionally substituted non-aromatic heterocyclic ring;

n represents the number of methylene chains and represents an integer of 0, 1 or 2; and a doublet containing a dotted line represents a single bond or a double bond;

provided that when A is —O—CH$_2$— or —S—CH$_2$—, $R^2$ represents an optionally substituted aryl group, or an optionally substituted heterocyclic group.

[2] A pharmaceutical agent comprising the compound represented by general formula (I) according to [1], a pharmaceutically acceptable salt thereof, or a solvate thereof.

[3] A pharmaceutical composition comprising the compound represented by general formula (I) according to [1], a pharmaceutically acceptable salt thereof, or a solvate thereof, and a pharmaceutically acceptable carrier.

[4] Use of the compound represented by general formula (I) according to [1], a pharmaceutically acceptable salt thereof, or a solvate thereof, for the production of a prophylactic or therapeutic agent for diseases in which T-type calcium channel is involved.

[5] The compound represented by general formula (I) according to [1], a pharmaceutically acceptable salt thereof, or a solvate thereof, for preventing or treating diseases in which T-type calcium channel is involved.

[6] A method for preventing or treating a disease in which T-type calcium channel is involved, the method comprising administering an effective amount of the compound represented by general formula (I) according to [1], or a pharmaceutically acceptable salt thereof.

Effects of the Invention

The compound of the present invention shows excellent antagonistic activity against T-type calcium channels, is stable in the body, is highly safe in view of the risk of, for example, genotoxicity, and is useful as a prophylactic and therapeutic agent for various diseases in which T-type calcium channel is involved. Examples of the diseases that can be prevented or treated by the antagonistic activity against T-type calcium channels include hypertension, atrial fibrillation, arrhythmia, cardiac hypertrophy, cardiac failure, renal dysfunction, pain, epilepsy, sleep disorder, obesity, and cancers.

DETAILED DESCRIPTION OF THE INVENTION

In the present specification, "halogen atoms" include a fluorine atom, a chlorine atom, a bromine atom, and an iodine atom. Preferred examples of the "halogen atoms" include a fluorine atom and a chlorine atom.

In the present specification, the term "C$_{a1-a2}$" means that the number of carbon atoms included in the relevant substituent is a1 to a2.

In the present specification, a "C$_{a1-a2}$ alkyl group" represents a linear, branched or cyclic alkyl group having a1 to a2 carbon atoms. Specific examples include a linear or branched C$_{1-6}$ alkyl group and a C$_{3-6}$ cyclic alkyl group, and more specific examples include a methyl group, an ethyl group, a n-propyl group, an isopropyl group, a 1-ethylpropyl group, a n-butyl group, an isobutyl group, a sec-butyl group, a tert-butyl group, a 2,2-dimethylpropyl group, a n-pentyl group, a n-hexyl group, a cyclopropyl group, a cyclopropylmethyl group, a cyclobutyl group, a cyclopentyl group, and a cyclohexyl group. In regard to general formula (I), the "C$_{1-6}$ alkyl group" of the optionally substituted C$_{1-6}$ alkyl group, which is represented by $R^4$, $R^5$ or $R^6$, is preferably a linear or branched C$_{1-6}$ alkyl group; more preferably a methyl group, an ethyl group, a n-propyl group, or an isopropyl group; even more preferably a methyl group or an ethyl group; and particularly preferably a methyl group. The "$C_{1-6}$ alkyl group" of the optionally substituted $C_{1-6}$ alkyl group, which is represented by $R^2$, is preferably a linear or branched $C_{1-6}$ alkyl group, or a $C_{3-6}$ cyclic alkyl group; more preferably an isobutyl group, a tert-butyl group, a cyclopropyl group, a cyclopentyl group, or a cyclopropylmethyl group; and even more preferably a tert-butyl group. The "$C_{3-6}$ alkyl group" of the optionally substituted $C_{3-6}$ alkyl group, which is represented by $R^3$, is preferably a linear or branched $C_{3-6}$ alkyl group, or a $C_{3-6}$ cyclic alkyl group; more preferably a cyclopropyl group, a 2,2-dimethylpropyl group, a cyclopentyl group, or a cyclohexyl group; and even more preferably a 2,2-dimethylpropyl group or a cyclohexyl group.

In the present specification, a "$C_{2-6}$ alkenyl group" represents a linear alkenyl group having 2 to 6 carbon atoms, or a branched or cyclic alkenyl group having 3 to 6 carbon atoms. Examples of the $C_{2-6}$ alkenyl group include a vinyl group, a 1-propenyl group, a 2-propenyl group, an isopropenyl group, a 2-methyl-1-propenyl group, a 1-butenyl group, a 2-butenyl group, a 3-butenyl group, a 1-pentenyl group, a 2-pentenyl group, a 1-hexenyl group, a 2-hexenyl group, a 1-cyclohexenyl group, a 2-cyclohexenyl group, and a 3-cyclohexenyl group.

In the present specification, a "$C_{1-6}$ alkoxy group" represents a group in which the "$C_{1-6}$ alkyl group" described above is bonded through an oxygen atom, and a linear or branched $C_{1-6}$ alkoxy group and a $C_{3-6}$ cyclic alkoxy group are included in the relevant alkoxy group. Examples of the $C_{1-6}$ alkoxy group include a methoxy group, an ethoxy group, a n-propoxy group, an isopropoxy group, a n-butoxy group, a sec-butoxy group, an isobutoxy group, a tert-butoxy group, a n-pentoxy group, a n-hexyloxy group, a cyclopropoxy group, a cyclobutoxy group, a cyclopentoxy group, and a cyclohexyloxy group. In regard to general formula (I), the "$C_{1-6}$ alkoxy group" of the optionally substituted $C_{1-6}$ alkoxy group, which is represented by $R^4$ or $R^5$, is preferably a linear or branched $C_{1-6}$ alkoxy group, or a $C_{3-6}$ cyclic alkoxy group; more preferably a methoxy group, an ethoxy group, a n-propoxy group, or an isopropoxy group; and even more preferably a methoxy group.

In the present specification, the term "aryl group" represents a monocyclic or polycyclic aromatic hydrocarbon group having 6 to 10 carbon atoms. Examples of the aryl group include a phenyl group, a 1-naphthyl group, and a 2-naphthyl group. In regard to general formula (I), the "aryl group" of the optionally substituted aryl group, which is represented by $R^2$ or $R^3$, is preferably a phenyl group.

In the present specification, a "crosslinked polycyclic hydrocarbon group" represents a crosslinked polycyclic hydrocarbon group having 7 to 10 carbon atoms. Examples of the crosslinked polycyclic hydrocarbon group include crosslinked polycyclic saturated hydrocarbon groups such as a bicyclo[2.2.1]heptanyl group, a bicyclo[3.2.1]octanyl group, a bicyclo[3.3.1]nonanyl group, a noradamantyl group, and an adamantyl group. In regard to general formula (I), the "crosslinked polycyclic hydrocarbon group" of the crosslinked polycyclic hydrocarbon group represented by $R^3$ is preferably a noradamantyl group or an adamantyl group.

In the present specification, a "fused polycyclic hydrocarbon group" represents a fused polycyclic hydrocarbon group having 8 to 14 carbon atoms. Examples of the fused polycyclic hydrocarbon group include an indanyl group, a tetrahydronaphthalenyl group, an octahydroindanyl group, and a decahydronaphthalenyl group. In general formula (I), the "fused polycyclic hydrocarbon group" of the fused polycyclic hydrocarbon group represented by $R^3$ is preferably an indanyl group.

In the present specification, a "heterocyclic group" represents a monocyclic or polycyclic heterocyclic group having a 3-membered to 10-membered ring containing one to three of an oxygen atom, a nitrogen atom, or a sulfur atom, and the position of bonding is not particularly limited as long as the group is chemically stable. Examples of the heterocyclic group include the following aromatic heterocyclic groups (heteroaryl groups) and non-aromatic heterocyclic groups.

In the present specification, a "heteroaryl group" represents a monocyclic or polycyclic aromatic heterocyclic group having a 3-membered to 10-membered ring containing one to three of an oxygen atom, a nitrogen atom, or a sulfur atom, and the position of bonding is not particularly limited as long as the group is chemically stable. Examples of the heteroaryl group include a pyrrolyl group, a furyl group, a thienyl group, a pyrazolyl group, an imidazolyl group, an oxazolyl group, an isoxazolyl group, a thiazolyl group, an isothiazolyl group, an oxadiazolyl group, a thiadiazolyl group, a triazolyl group, a pyridyl group, a pyridazinyl group, a pyrimidinyl group, a pyrazinyl group, a quinolyl group, an isoquinolyl group, an indolyl group, a benzofuranyl group, a benzothiophenyl group, an indazolyl group, a benzimidazolyl group, a benzisoxazolyl group, a benzoxazolyl group, a benzisothiazolyl group, and a benzothiazolyl group. Furthermore, in the case of a fused ring, a portion of any one of the rings may be hydrogenated.

In the present specification, a "non-aromatic heterocyclic ring" represents a monocyclic, bicyclic or tricyclic non-aromatic heterocyclic ring having a 3-membered to 10-membered ring containing at least one of an oxygen atom, a nitrogen atom, or a sulfur atom. Examples of the non-aromatic heterocyclic ring include an azetidine ring, a pyrrolidine ring, a piperidine ring, a piperazine ring, a hexamethyleneimine ring, a heptamethyleneimine ring, a homopiperazine ring, a 2,5-diazabicyclo[2.2.1]heptane ring, a morpholine ring, a thiomorpholine ring, a tetrahydrofuran ring, a tetrahydropyran ring, a tetrahydrothiophene ring, a tetrahydrothiopyran ring, an oxetane ring, a dioxolane ring, a dioxane ring, and an oxaadamantane ring.

In regard to general formula (I), among the optionally substituted heterocyclic groups, which are represented by $R^2$ or $R^3$, the "heteroaryl group" of the optionally substituted heteroaryl group is preferably a pyridyl group, a pyrazolyl group, an oxazolyl group, a thiazolyl group, a thienyl group, an indazolyl group, a quinolyl group, an indolyl group, or a benzofuranyl group; and more preferably a pyrazolyl group, a thienyl group, an indolyl group, or a benzofuranyl group.

In regard to general formula (I), among the optionally substituted heterocyclic groups, which are represented by $R^2$ or $R^3$, the "non-aromatic heterocyclic ring" of the optionally substituted non-aromatic heterocyclic group is preferably a pyrrolidine ring, a piperidine ring, a hexamethyleneimine ring, an oxetane ring, or an oxaadamantane ring; and more preferably a piperidine ring or an oxaadamantane ring.

In a case in which $R^4$ and $R^5$ together form an optionally substituted non-aromatic heterocyclic ring, the relevant "non-aromatic heterocyclic ring" is preferably a dioxolane ring, a dioxane ring, or a tetrahydrofuran ring; and more preferably a dioxane ring. In a case in which $R^6$ and $R^2$ together form an optionally substituted non-aromatic heterocyclic ring, the relevant "non-aromatic heterocyclic ring" is preferably a pyrrolidine ring, a piperidine ring, or a morpholine ring; and more preferably a morpholine ring.

In the present specification, the term "optionally substituted" means that the relevant group is "unsubstituted", or has one to five, and preferably one to three, identical or different substituents at positions where substitution can be made. In the present specification, in a case in which a $C_{1-6}$ alkyl group, an aryl group, a heterocyclic group, a heteroaryl group, a non-aromatic heterocyclic ring, or a $C_{1-6}$ alkoxy group optionally has a substituent, the relevant substituent is preferably a halogen atom, a hydroxy group, a cyano group, a nitro group, a $C_{1-6}$ alkyl group, a $C_{2-6}$ alkenyl group, a $C_{1-6}$ alkoxy group, an acyl group, a carboxyl group, a $C_{1-6}$ alkylcarbonylamino group, a $C_{1-6}$ alkoxycarbonyl group, a carbamoyl group, a sulfamoyl group, a $C_{1-6}$ alkylsulfanyl group, a $C_{1-6}$ alkylsulfenyl group, a $C_{1-6}$ alkylsulfonyl group, an amino group, a $C_{1-6}$ alkylamino group, a $C_{1-6}$ dialkylamino group, an aryl group, a heteroaryl group, or a non-aromatic heterocyclic group, and these groups may further have substituents. In a case in which a $C_{1-6}$ alkyl group, a $C_{2-6}$ alkenyl group, or a $C_{1-6}$ alkoxy group substitutes an aryl group, a fused ring may be formed by having the relevant substituent substituted at two different positions on the aromatic ring.

A $C_{1-6}$ alkyl or $C_{1-6}$ alkoxy group having a substituent is preferably a $C_{1-6}$ alkyl or $C_{1-6}$ alkoxy group having one to five, and preferably one to three, substituents selected from a $C_{1-6}$ alkyl group, a halogen atom, a cyano group, a hydroxy group, or a $C_{1-6}$ alkoxy group.

An aryl, heterocyclic group, heteroaryl or non-aromatic heterocyclic ring having a substituent, is preferably an aryl, heterocyclic group, heteroaryl, or non-aromatic heterocyclic ring, all having one to five, and preferably one to three, substituents selected from a $C_{1-6}$ alkyl group, a halogen atom, a cyano group, a hydroxy group, or a $C_{1-6}$ alkoxy group.

In regard to general formula (I) of the present invention, more preferred cases include the following cases <1> to <5>, and arbitrary combinations of <1> to <5>.

<1> $R^1$ is preferably —NH(C═O)—V—$R^3$, —(C═O)NH—V—$R^3$, or the following formula:

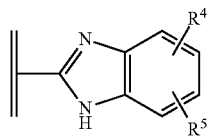

and more preferably —NH(C═O)—V—$R^3$ or —(C═O)NH—V—$R^3$.

V is preferably a single bond or methylene, and more preferably a single bond. Preferred examples of $R^3$ include a $C_{3-6}$ alkyl group, an adamantyl group, a noradamantyl group, an optionally substituted aryl group, an optionally substituted heteroaryl group (wherein regarding the substituent on the aryl group or heteroaryl group, one to three substituents selected from a linear or branched $C_{1-6}$ alkyl group, a $C_{3-6}$ cyclic alkyl group, a halogen atom, a cyano group, a hydroxy group and a $C_{1-6}$ alkoxy group are preferred), and an oxaadamantyl group; and more preferred examples include an adamantyl group, a phenyl group, a benzofuranyl group, an indolyl group, a pyrazolyl group, an oxazolyl group, a thienyl group, a thiazolyl group (here, regarding the substituent on the phenyl group or heteroaryl group, one to three substituents selected from a linear or branched $C_{1-6}$ alkyl group, a $C_{3-6}$ cyclic alkyl group, a halogen atom, a cyano group, a hydroxy group and a $C_{1-6}$ alkoxy group are preferred), and an oxaadamantyl group. Even more preferred examples include an adamantyl group; a phenyl group that is unsubstituted or is substituted with one or two substituents selected from a halogen atom, a methyl group, an ethyl group, a cyclopropyl group, a methoxy group or a cyano group; a benzofuranyl group that is unsubstituted or is substituted with one or two substituents selected from a halogen atom, a methyl group, an ethyl group, a cyclopropyl group, a methoxy group or a cyano group; an indolyl group that is unsubstituted or is substituted with one or two substituents selected from a halogen atom, a methyl group, an ethyl group, a cyclopropyl group, a methoxy group or a cyano group; a pyrazolyl group that is unsubstituted or is substituted with one or two substituents selected from a halogen atom, a methyl group, an ethyl group, a cyclopropyl group, a methoxy group or a cyano group; an oxazolyl group that is unsubstituted or is substituted with one or two substituents selected from a halogen atom, a methyl group, an ethyl group, a cyclopropyl group, a methoxy group or a cyano group; a thiazolyl group that is unsubstituted or is substituted with one or two substituents selected from a halogen atom, a methyl group, an ethyl group, a cyclopropyl group, a thienyl group substituted with a methyl group, a methoxy group, or a cyano group; and an oxaadamantyl group.

<2> $R^2$ is preferably a optionally substituted $C_{1-6}$ alkyl group; more preferably a linear or branched $C_{1-6}$ alkyl group which may be substituted with one to three substituents selected from a halogen atom, a cyano group, a hydroxy group and a $C_{1-6}$ alkoxy group, or a cyclic $C_{3-6}$ alkyl group which is optionally substituted with one to three substituents selected from a halogen atom, a cyano group, a hydroxy group and a $C_{1-6}$ alkoxy group; and even more preferably a tert-butyl group, a 1-methylcyclopropyl group, a 1-trifluoromethylcyclopropyl group, a 2-methoxy-1,1-dimethylethyl group, or a 2-hydroxy-1,1-dimethylethyl group.

<3> X is preferably an oxygen atom.

<4> A is preferably formula: —$NR^6$—, and $R^6$ is preferably a hydrogen atom or a methyl group.

<5> n is preferably 1.

As the compound of general formula (I) of the present invention, a combination of <2> to <5> is more preferred, and a combination of <1> to <5> is particularly preferred.

Specific preferred examples of the compound of general formula (I) of the present invention include the following compounds (comprising pharmaceutically acceptable salts of these compounds, and solvates of these compounds or salts).

2-[(exo)-8-(tert-Butylcarbamoyl)methyl-8-azabicyclo[3.2.1]octan-3-yl]-N-(3-chlorophenyl)acetamide;

2-[(exo)-8-(tert-Butylcarbamoyl)methyl-8-azabicyclo[3.2.1]octan-3-yl]-N-(3-fluoro-5-methoxyphenyl)acetamide;

N-[(exo)-8-(tert-Butylcarbamoyl)methyl-8-azabicyclo[3.2.1]octan-3-yl]methylbenzofuran-3-carboxamide;

3-Cyano-5-fluoro-N-{(exo)-8-[(2-hydroxy-1,1-dimethylethyl)carbamoyl]methyl-8-azabicyclo[3.2.1]octan-3-yl}methylbenzamide;

N-[(exo)-8-(tert-Butylcarbamoyl)methyl-8-azabicyclo[3.2.1]octan-3-yl]methyl-5-isopropyl-2-methyl-2H-pyrazole-3-carboxamide;

N-[(exo)-8-(tert-Butylcarbamoyl)methyl-8-azabicyclo[3.2.1]octan-3-yl]methyl-2,5-dimethyl-2H-pyrazole-3-carboxamide;

N-[(exo)-8-(tert-Butylcarbamoyl)methyl-8-azabicyclo[3.2.1]octan-3-yl]methyl-1-methyl-1H-indole-3-carboxamide;

1-acetyl-N-[(exo)-8-(tert-Butylcarbamoyl)methyl-8-azabicyclo[3.2.1]octan-3-yl]methyl-1H-indole-3-carboxamide;
N-[(exo)-8-(tert-Butylcarbamoyl)methyl-8-azabicyclo[3.2.1]octan-3-yl]methyl-5-methoxy-1,2-dimethyl-1H-indole-3-carboxamide;
N-[(exo)-8-(tert-Butylcarbamoyl)methyl-8-azabicyclo[3.2.1]octan-3-yl]methyl-5-chloro-1H-indole-3-carboxamide;
N-[(exo)-8-(tert-Butylcarbamoyl)methyl-8-azabicyclo[3.2.1]octan-3-yl]methyl-1-ethyl-1H-indole-3-carboxamide;
N-[(exo)-8-(tert-Butylcarbamoyl)methyl-8-azabicyclo[3.2.1]octan-3-yl]methyl-1,2-dimethyl-1H-indole-3-carboxamide;
N-{(exo)-8-[tert-Butyl(methyl)carbamoyl]methyl-8-azabicyclo[3.2.1]octan-3-yl}methyl-5-isopropyl-2-methyl-2H-pyrazole-3-carboxamide;
N-[(exo)-8-(tert-Butylcarbamoyl)methyl-8-azabicyclo[3.2.1]octan-3-yl]methyl-5-methyl-1H-indole-3-carboxamide;
N-[(exo)-8-(tert-Butylcarbamoyl)methyl-8-azabicyclo[3.2.1]octan-3-yl]methyl-5-fluoro-1H-indole-3-carboxamide;
N-{(exo)-8-[(1-Methylcyclopropyl)carbamoyl]methyl-8-azabicyclo[3.2.1]octan-3-yl}methyl-1-methyl-1H-indole-3-carboxamide;
1-Methyl-N-((exo)-8-{1-(trifluoromethyl)cyclopropyl]carbamoyl}methyl-8-azabicyclo[3.2.1]octan-3-yl)methyl-1H-indole-3-carboxamide;
N-{(exo)-8-[(2-Methoxy-1,1-dimethylethyl)carbamoyl]methyl-8-azabicyclo[3.2.1]octan-3-yl}methyl-1-methyl-1H-indole-3-carboxamide;
N-{(exo)-8-[tert-Butyl(methyl)carbamoyl]methyl-8-azabicyclo[3.2.1]octan-3-yl}methyl-1-methyl-1H-indole-3-carboxamide;
N-[(exo)-8-(tert-Butylcarbamoyl)methyl-8-azabicyclo[3.2.1]octan-3-yl]methyl-1,4-dimethyl-1H-indole-3-carboxamide;
N-[(exo)-8-(tert-Butylcarbamoyl)methyl-8-azabicyclo[3.2.1]octan-3-yl]methyl-1,6-dimethyl-1H-indole-3-carboxamide;
N-[(exo)-8-(tert-Butylcarbamoyl)methyl-8-azabicyclo[3.2.1]octan-3-yl]methyl-1,7-dimethyl-1H-indole-3-carboxamide;
N-[(exo)-8-(tert-Butylcarbamoyl)methyl-8-azabicyclo[3.2.1]octan-3-yl]methyl-3-chlorobenzamide;
N-[(exo)-8-(tert-Butylcarbamoyl)methyl-8-azabicyclo[3.2.1]octan-3-yl]methyl-3-chloro-5-methoxybenzamide;
N-[(exo)-8-(tert-Butylcarbamoyl)methyl-8-azabicyclo[3.2.1]octan-3-yl]methyl-3-chloro-5-fluorobenzamide;
N-[(exo)-8-(tert-Butylcarbamoyl)methyl-8-azabicyclo[3.2.1]octan-3-yl]methyl-3-fluoro-5-methylbenzamide;
N-[(exo)-8-(tert-Butylcarbamoyl)methyl-8-azabicyclo[3.2.1]octan-3-yl]methyl-3-fluoro-5-methoxybenzamide;
N-[(exo)-8-(tert-Butylcarbamoyl)methyl-8-azabicyclo[3.2.1]octan-3-yl]methyl-5-chloropyridine-3-carboxamide;
N-[(exo)-8-(tert-Butylcarbamoyl)methyl-8-azabicyclo[3.2.1]octan-3-yl]methyl-5-methylpyridine-3-carboxamide;
N-[(exo)-8-(tert-Butylcarbamoyl)methyl-8-azabicyclo[3.2.1]octan-3-yl]methyl-5-cyclopropylpyridine-3-carboxamide;
5-tert-butyl-N-[(exo)-8-(tert-Butylcarbamoyl)methyl-8-azabicyclo[3.2.1]octan-3-yl]methyl-2-methyl-2H-pyrazole-3-carboxamide;
N-[(exo)-8-(tert-Butylcarbamoyl)methyl-8-azabicyclo[3.2.1]octan-3-yl]methyl-3-methoxy-5-methylbenzamide;
N-[(exo)-8-(tert-Butylcarbamoyl)methyl-8-azabicyclo[3.2.1]octan-3-yl]methyl-1-isopropyl-1H-pyrazole-4-carboxamide;
N-[(exo)-8-(tert-Butylcarbamoyl)methyl-8-azabicyclo[3.2.1]octan-3-yl]methylbenzofuran-2-carboxamide;
N-[(exo)-8-(tert-Butylcarbamoyl)methyl-8-azabicyclo[3.2.1]octan-3-yl]methyl-3-methylbenzofuran-2-carboxamide;
N-[(exo)-8-(tert-Butylcarbamoyl)methyl-8-azabicyclo[3.2.1]octan-3-yl]methyl-4-chlorobenzamide;
N-[(exo)-8-(tert-Butylcarbamoyl)methyl-8-azabicyclo[3.2.1]octan-3-yl]methyl-4-fluorobenzamide;
N-[(exo)-8-(tert-Butylcarbamoyl)methyl-8-azabicyclo[3.2.1]octan-3-yl]methyl-3-cyano-5-fluorobenzamide;
N-[(exo)-8-(tert-Butylcarbamoyl)methyl-8-azabicyclo[3.2.1]octan-3-yl]methyl-2-isopropyl-4-methylthiazole-5-carboxamide;
2-tert-butyl-N-[(exo)-8-(tert-Butylcarbamoyl)methyl-8-azabicyclo[3.2.1]octan-3-yl]methyl-4-methyloxazole-5-carboxamide;
N-[(exo)-8-(tert-Butylcarbamoyl)methyl-8-azabicyclo[3.2.1]octan-3-yl]methyl-2-ethylbenzofuran-3-carboxamide;
N-[(exo)-8-(tert-Butylcarbamoyl)methyl-8-azabicyclo[3.2.1]octan-3-yl]methyl-2-methylbenzofuran-3-carboxamide;
N-[(exo)-8-(tert-Butylcarbamoyl)methyl-8-azabicyclo[3.2.1]octan-3-yl]methyl-5-methoxy-2-methylbenzofuran-3-carboxamide;
N-[(exo)-8-(tert-Butylcarbamoyl)methyl-8-azabicyclo[3.2.1]octan-3-yl]methyl-2,4-difluorobenzamide;
N-{(exo)-8-[(1-Methylcyclopropyl)carbamoyl]methyl-8-azabicyclo[3.2.1]octan-3-yl}methylbenzofuran-3-carboxamide;
N-((exo)-8-{[1-(Trifluoromethyl)cyclopropyl]carbamoyl}methyl-8-azabicyclo[3.2.1]octan-3-yl)methylbenzofuran-3-carboxamide;
N-{(exo)-8-[(2-Methoxy-1,1-dimethylethyl) carbamoyl]methyl-8-azabicyclo[3.2.1]octan-3-yl}methylbenzofuran-3-carboxamide;
N-{(exo)-8-[(2-Hydroxy-1,1-dimethylethyl)carbamoyl]methyl-8-azabicyclo[3.2.1]octan-3-yl}methylbenzofuran-3-carboxamide;
N-{(exo)-8-[2-(tert-Butylcarbamoyl)ethyl]-8-azabicyclo[3.2.1]octan-3-yl}methylbenzofuran-3-carboxamide;
N-{(exo)-8-[tert-Butyl(methyl) carbamoyl]methyl-8-azabicyclo[3.2.1]octan-3-yl}methylbenzofuran-3-carboxamide;
2-Methyl-N-((exo)-8-{[1-(trifluoromethyl)cyclopropyl]carbamoyl}methyl-8-azabicyclo[3.2.1]octan-3-yl)methyl-4,5,6,7-tetrahydrobenzofuran-3-carboxamide;
5-Methoxy-3-methyl-N-((exo)-8-{[1-(trifluoromethyl)cyclopropyl]carbamoyl}methyl-8-azabicyclo[3.2.1]octan-3-yl)methylbenzamide;
N-{(exo)-8-[(2-Hydroxy-1,1-dimethylethyl) carbamoyl]methyl-8-azabicyclo[3.2.1]octan-3-yl}methyl-2-methyl-4,5,6,7-tetrahydrobenzofuran-3-carboxamide;
N-[(exo)-8-(tert-Butylcarbamoyl)methyl-8-azabicyclo[3.2.1]octan-3-yl]methyl-5-chloro-1-methyl-1H-indole-3-carboxamide;
N-[(exo)-8-(tert-Butylcarbamoyl)methyl-8-azabicyclo[3.2.1]octan-3-yl]methyl-1,5-dimethyl-1H-indole-3-carboxamide;

N-[(exo)-8-(tert-Butylcarbamoyl)methyl-8-azabicyclo
[3.2.1]octan-3-yl]methyl-5-fluoro-1-methyl-1H-indole-3-
carboxamide;

N-[(exo)-8-(tert-Butylcarbamoyl)methyl-8-azabicyclo
[3.2.1]octan-3-yl]methyl-1-isopropyl-1H-indole-3-car-
boxamide;

3-Chloro-5-fluoro-N-{((exo)-8-[(2-methoxy-1,1-dimethyl-
ethyl)carbamoyl]methyl-8-azabicyclo[3.2.1]octan-3-
yl}methylbenzamide;

N-{(exo)-8-[(2-Hydroxy-1,1-dimethylethyl)carbamoyl]
methyl-8-azabicyclo[3.2.1]octan-3-yl}methyl-1-methyl-
1H-indole-3-carboxamide;

3-chloro-5-fluoro-N-[(exo)-8-(2-{[1-(Trifluoromethyl)cy-
clopropyl]carbamoyl}ethyl)-8-azabicyclo[3.2.1]octan-3-
yl]methylbenzamide;

3-Chloro-N-{(exo)-8-[(3-methyloxetan-3-yl) carbamoyl]
methyl-8-azabicyclo[3.2.1]octan-3-yl}methylbenzamide;

3-Fluoro-N-{(exo)-8-[(3-methyloxetan-3-yl)carbamoyl]
methyl-8-azabicyclo[3.2.1]octan-3-yl}methylbenzamide;

3-Chloro-5-fluoro-N-{(exo)-8-[(3-methyloxetan-3-yl)car-
bamoyl]methyl-8-azabicyclo[3.2.1]octan-3-
yl}methylbenzamide;

N-[(exo)-8-(tert-Butylcarbamoyl)methyl-8-azabicyclo
[3.2.1]octan-3-yl]methyl-3-fluorobenzamide;

3-Chloro-5-fluoro-N-((exo)-8-{[1-(trifluoromethyl)cyclo-
propyl]carbamoyl}methyl-8-azabicyclo[3.2.1]octan-3-yl)
methylbenzamide;

3-Chloro-5-fluoro-N-{(exo)-8-[(1-methylcyclopropyl) car-
bamoyl]methyl-8-azabicyclo[3.2.1]octan-3-
yl}methylbenzamide;

3-Chloro-5-fluoro-N-{(exo)-8-[(2-hydroxy-1,1-dimethyl-
ethyl)carbamoyl]methyl-8-azabicyclo[3.2.1]octan-3-
yl}methylbenzamide;

N-{(exo)-8-[tert-Butyl(methyl)carbamoyl]methyl-8-azabi-
cyclo[3.2.1]octan-3-yl}methyl-3-chloro-5-fluorobenz-
amide;

N-((exo)-8-{[1-(Methoxymethyl)cyclopropyl]
carbamoyl}methyl-8-azabicyclo[3.2.1]octan-3-yl)
methyl-1-methyl-1H-indole-3-carboxamide;

N-[(endo)-8-(tert-Butylcarbamoyl)methyl-8-azabicyclo
[3.2.1]octan-3-yl]methylbenzofuran-3-carboxamide;

N-[(endo)-8-(tert-Butylcarbamoyl)methyl-8-azabicyclo
[3.2.1]octan-3-yl]methyl-1-methyl-1H-indole-3-carbox-
amide;

N-[(endo)-8-(tert-Butylcarbamoyl)methyl-8-azabicyclo
[3.2.1]octan-3-yl]methyl-5-isopropyl-2-methyl-2H-pyra-
zole-3-carboxamide;

N-[(endo)-8-(tert-Butylcarbamoyl)methyl-8-azabicyclo
[3.2.1]octan-3-yl]methyl-3-chloro-5-fluorobenzamide;

N-[(endo)-8-(tert-Butylcarbamoyl)methyl-8-azabicyclo
[3.2.1]octan-3-yl]methyl-3,5-dichlorobenzamide;

N-[(endo)-8-(tert-Butylcarbamoyl)methyl-8-azabicyclo
[3.2.1]octan-3-yl]methyl-3-chlorobenzamide;

N-[(exo)-8-(tert-Butylcarbamoyl)methyl-8-azabicyclo
[3.2.1]octan-3-yl]methyl-2,4-dimethylthiazole-5-carbox-
amide;

2-[(endo)-8-(tert-Butylcarbamoyl)methyl-8-azabicyclo
[3.2.1]octan-3-yl]-N-(2-oxaadamantan-1-yl)acetamide;

N-[(exo)-8-(tert-Butylcarbamoyl)methyl-8-azabicyclo
[3.2.1]octan-3-yl]methyl-1-ethyl-4-methyl-1H-indole-3-
carboxamide;

N-[(exo)-8-(tert-Butylcarbamoyl)methyl-8-azabicyclo
[3.2.1]octan-3-yl]methyl-1-ethyl-2-methyl-1H-indole-3-
carboxamide;

N-[(exo)-8-(tert-Butylcarbamoyl)methyl-8-azabicyclo
[3.2.1]octan-3-yl]methyl-1-ethyl-5-methyl-1H-indole-3-
carboxamide;

1-Ethyl-4-methyl-N-[(exo)-8-{[1-(trifluoromethyl)cyclo-
propyl]carbamoyl}methyl-8-azabicyclo[3.2.1]octan-3-yl]
methyl-1H-indole-3-carboxamide;

N-[(exo)-8-(tert-Butylcarbamoyl)methyl-8-azabicyclo
[3.2.1]octan-3-yl]methyl-5-cyclopropyl-2-methyl-2H-
pyrazole-3-carboxamide;

N-[(exo)-8-(tert-Butylcarbamoyl)methyl-8-azabicyclo
[3.2.1]octan-3-yl]methyl-2-methyl-5-trifluoromethyl-2H-
pyrazole-3-carboxamide;

N-[(exo)-8-(tert-Butylcarbamoyl)methyl-8-azabicyclo
[3.2.1]octan-3-yl]methyl-2-methyl-4,5,6,7-tetrahydro-
2H-indazole-3-carboxamide;

N-tert-Butyl-2-[(exo)-3-(4-methyl-1H-benzimidazol-2-yl)
methyl-8-azabicyclo[3.2.1]octan-8-yl]acetamide;

N-tert-Butyl-2-[(exo)-3-(4-methoxy-1H-benzimidazol-2-yl)
methyl-8-azabicyclo[3.2.1]octan-8-yl]acetamide;

N-tert-Butyl-2-[(endo)-3-(4-methoxy-1H-benzimidazol-2-
yl)methyl-8-azabicyclo[3.2.1]octan-8-yl]acetamide;

N-tert-Butyl-2-[(endo)-3-(4-methyl-H-benzimidazol-2-yl)
methyl-8-azabicyclo[3.2.1]octan-8-yl]acetamide;

N-tert-Butyl-2-[(exo)-3-(4-fluoro-6-methoxy-1H-benzimi-
dazol-2-yl)methyl-8-azabicyclo[3.2.1]octan-8-yl]acet-
amide;

N-tert-Butyl-2-[(exo)-3-(4,5-dimethoxy-1H-benzimidazol-
2-yl)methyl-8-azabicyclo[3.2.1]octan-8-yl]acetamide;
and N-tert-Butyl-2-[(exo)-3-(4,7-dimethoxy-1H-benzimidazol-
2-yl)methyl-8-azabicyclo[3.2.1]octan-8-yl]acetamide.

According to the present specification, the structural formula of a compound may represent certain isomers for convenience; however, the present invention includes all of isomers such as geometric isomers, optical isomers based on asymmetric carbon, stereoisomers and tautomers, and isomer mixtures that occur due to the structure of the compound. Thus, the compound is not intended to be limited to the actual description of the formula for convenience, and may be any one isomer, or may be a mixture. Therefore, the compound of the present invention which have any asymmetric carbon atoms in the molecule may be optically active or racemic; however, according to the present invention, all of these are included in the compound without any limitation.

Furthermore, the present invention includes pharmaceutically acceptable salts of the compound of the present invention. Specific examples thereof include inorganic salts such as hydrochloride, hydrobromide, hydroiodide, sulfate, nitrate, and phosphate; acid addition salts formed with organic acids, such as formate, acetate, trichloroacetate, trifluoroacetate, propionate, oxalate, malonate, succinate, fumarate, maleate, lactate, malate, tartrate, citrate, methanesulfonate, ethanesulfonate, p-toluenesulfonate, aspartate, and glutamate; salts formed with inorganic bases, such as sodium salt, potassium salt, magnesium salt, calcium salt, and aluminum salt; salts formed with organic bases such as methylamine, ethylamine, ethanolamine, lysine, and ornithine; and ammonium salts.

Furthermore, the present invention also includes pharmaceutically acceptable prodrugs of the compound of the present invention. A pharmaceutically acceptable prodrug is a compound which is subjected to enzymatic oxidation, reduction or hydrolysis under physiological conditions in the living body, and is converted to the compound (I) of the present invention. Examples of the group that forms a prodrug include the groups described in Prog. Med., 5, 2157-2161 (1985), and "Development of Pharmaceutical Products" (Hirokawa Shoten Co., Ltd., 1990), Vol. 7 Molecular Design, p. 163-198.

Furthermore, according to the present invention, hydrates, various solvates, and crystal polymorphism of the compound of the present invention and pharmaceutically acceptable salts thereof may exist. However, similarly, without any limitations, any of the crystal forms, a single crystal form or a mixture of crystal forms, may exist, and all of them are included in the present invention.

Furthermore, the present invention includes isotope (for example, $^2H$, $^3H$, $^{14}C$, $^{35}S$, or $^{125}I$) labelled compounds obtained by labeling the compound of the present invention therewith.

The compound of the present invention and pharmaceutically acceptable salts thereof can be produced by applying various synthesis methods that are known per se. When introducing a substituent or converting a functional group, in the case in which a reactive substituent such as an amino group, a hydroxyl group or a carboxyl group is present, a desired compound may be obtained by introducing a protective group for the relevant substituent as necessary, and removing the protective group after the intended reaction is completed. In regard to the selection of a protective group, introduction of a protective group, and removal of a protective group, methods may be appropriately selected from the methods described in, for example, Greene and Wuts, "Protective Groups in Organic Synthesis (Third Edition)" (Wiley & Sons, Inc.), and carried out.

The method for producing the substituted tropane derivative of the present invention includes, for example, the following methods; however, the method for producing the compound of the present invention is not intended to be limited to these methods.

Production Method 1

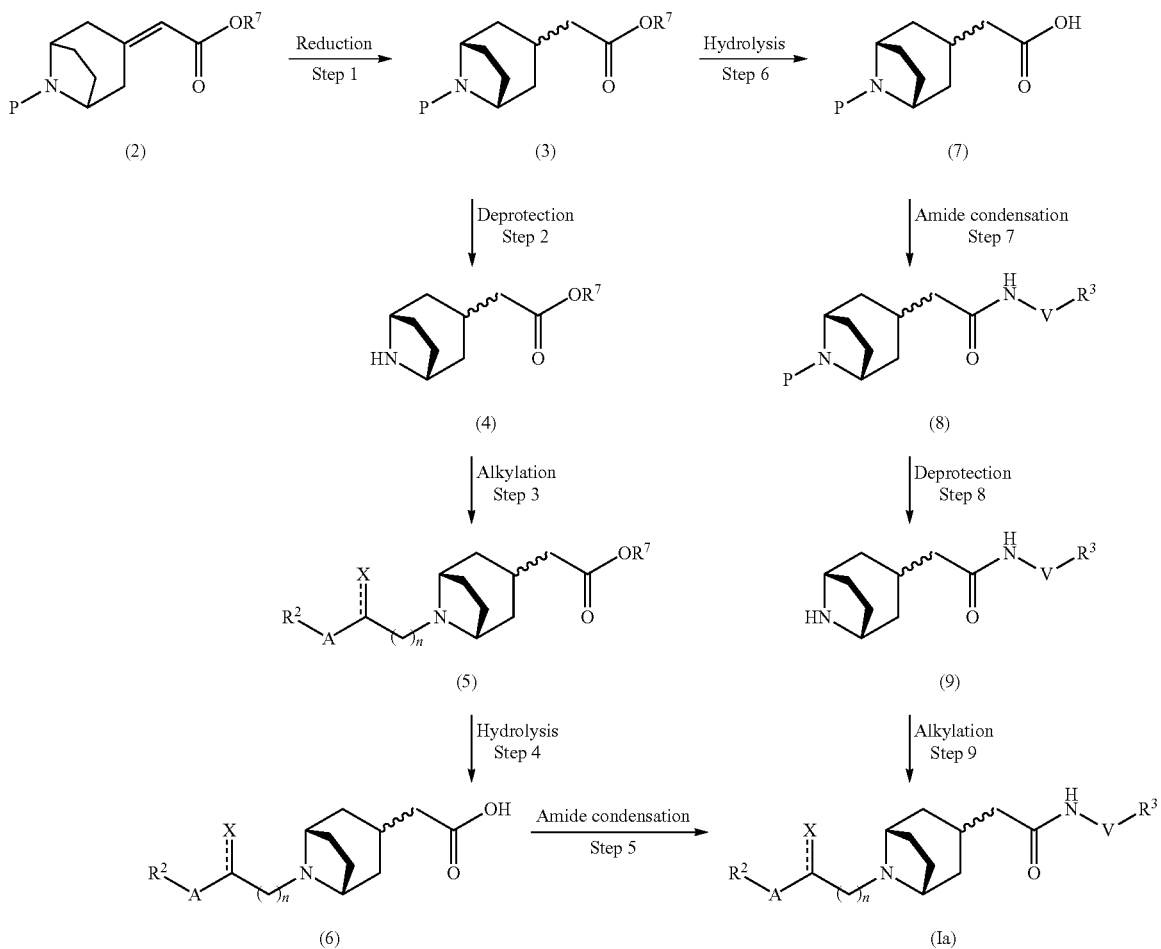

wherein $R^2$, $R^3$, V, X, A, n, and a doublet containing a dotted line respectively mean the same as defined above; $R^7$ represents a $C_{1-4}$ alkyl group; and P represents a protective group for an amino group.

Step 1: Reduction

Compound (3) can be produced by a reduction reaction of compound (2). The reduction reaction can be carried out by, for example, the reaction in an inert solvent in a hydrogen atmosphere in the presence of a metal catalyst. Regarding the metal catalyst, a palladium catalyst such as palladium or palladium hydroxide; a rhodium catalyst such as rhodium or Wilkinson's catalyst; an iridium catalyst such as Crabtree's catalyst; a ruthenium catalyst such as ruthenium or Noyori catalyst; or a platinum catalyst such as platinum or platinum oxide, can be used as a simple substance or as a supported catalyst on, for example, carbon, a hydrocarbon or a metal. Examples of the inert solvent that can be used include alcohols such as methanol, ethanol, and 2-propanol; esters such as ethyl acetate and butyl acetate; ethers such as tetrahydrofuran (THF) and 1,4-dioxane; aromatic hydrocarbons such as benzene and toluene; organic acids such as acetic acid; inorganic acids such as hydrochloric acid; water; and mixtures thereof. The reaction temperature is preferably in the range of room temperature to temperature for heating reflux, and the reaction time is preferably 0.5 to 168 hours.

Step 2: Deprotection

Compound (4) can be produced by deprotection of the protective group for the tropane ring nitrogen atom of compound (3). For the deprotection, any method can be appropriately selected for use from methods generally known in the field of organic synthetic chemistry, for example, methods described in T. W. Greene and P. G. Wuts, "Greene's Protective Groups in Organic Synthesis (Fourth Edition)" (John Wiley & Sons, Inc.). For example, in a case in which the protective group P is a tert-butoxycarbonyl (Boc) group, deprotection can be carried out by causing compound (3) to react in the presence or absence of an acid catalyst, and in the presence or absence of an inert solvent. Regarding the acid catalyst, for example, a carboxylic acid compound such as trifluoroacetic acid or acetic acid; an inorganic acid such as hydrochloric acid or sulfuric acid; or a solution of hydrogen chloride in an inert solvent can be used. Examples of the inert solvent that can be used include ethers; esters; alcohols; halogenated hydrocarbons such as dichloromethane and chloroform; nitriles such as acetonitrile, propionitrile, and benzonitrile; aromatic hydrocarbons; water; and mixtures thereof. The reaction temperature is preferably in the range of 0° C. to temperature for heating reflux, and the reaction time is preferably 0.5 to 24 hours.

Step 3: Alkylation

Compound (5) can be produced by an alkylation reaction of compound (4). The alkylation reaction can be carried out by causing compound (4) to react with an alkyl halide compound or a substituted epoxide compound in an inert solvent in the presence or absence of a base and/or additive. Examples of the base that can be used include amidines such as 1,8-diazabicyclo[5,4,0]-7-undecene (DBU); tertiary organic amines such as triethylamine and N-ethyldiisopropylamine; metal hydrides; metal alkoxides; alkali metal carbonates; alkali metal hydrogen carbonates; and alkali metal hydroxides. Examples of the additives that can be used include alkali metal iodides; quaternary ammonium salts such as tetrabutylammonium iodide; and phase transfer catalysts such as a crown ether. Examples of the inert solvent that can be used include ethers, esters, hydrogenated hydrocarbons, nitriles, aromatic hydrocarbons, ketones, water, and mixtures thereof. The reaction temperature is preferably in the range of 0° C. to temperature for heating reflux, and the reaction time is preferably 0.5 to 168 hours.

Step 4: Hydrolysis

Compound (6) can be produced by a hydrolysis reaction of compound (5). The hydrolysis reaction may be carried out under conventional conditions, and for example, the reaction can be carried out by allowing compound (5) in an inert solvent in the presence of an alkali metal hydroxide such as sodium hydroxide or potassium hydroxide. Regarding the inert solvent, alcohols; ethers; ketones such as acetone and diethyl ketone; water, or mixtures thereof can be used. The reaction temperature is preferably in the range of 0° C. to temperature for heating reflux, and the reaction time is preferably 15 minutes to 168 hours.

Step 5: Amide condensation Compound (Ia) can be produced by a known method for converting a carboxyl group of compound (6) to an amide structure, for example, by an amide condensation reaction. The amide condensation reaction can be achieved by, for example, causing compound (6) to react with an amine compound in an inert solvent in the presence of a condensing agent and in the presence or absence of a base. Furthermore, the present reaction may also be carried out by adding a condensation aid such as 1-hydroxybenzotriazole (HOBt) or 1-hydroxy-7-azabenzotriazole (HOAt). Examples of the condensing agent that can be used include dicyclohexylcarbodiimide (DCC), 1-ethyl-3-(3-dimethylaminopropyl)carbodiimide hydrochloride (EDC.HCl), diisopropylcarbodiimide (DIPC), 1-ethyl-3-(3-dimethylaminopropyl)carbonium hexafluorophosphate (BOP), (benzotriazol-1-yloxy)trispyrrolidinophosphonium hexafluorophosphate (PyBOP), diphenylphosphorylazide (DPPA), carbonyldiimidazole (CDI), (1-cyano-2-ethoxy-2-oxoethylideneaminooxy)dimethylaminomorpholinocarbenium hexafluorophosphate (COMU), and 2-(1H-7-azabenzotriazol-1-yl)-1,1,3,3-tetramethyluronium hexafluorophosphate (HATU). The inert solvent is not particularly limited as long as the reaction proceeds; however, for example, a halogenated hydrocarbon, a nitrile, an ether, an ester, N,N-dimethylformamide (DMF), N,N-dimethylacetamide (DMA), water, or a mixture thereof. Regarding the base, for example, pyridine, 4-dimethylaminopyridine, or a tertiary organic amine can be used. The reaction temperature is preferably in the range of 0° C. to temperature for heating reflux, and the reaction time is preferably 15 minutes to 168 hours.

Meanwhile, the amine compound to be condensed may be a commercially available product, or can be produced by a known method.

Step 6: Hydrolysis

Compound (7) can be produced by a hydrolysis reaction of compound (3). The hydrolysis reaction can be carried out by a method similar to that of Step 4.

Step 7: Amide Condensation

Compound (8) can be produced by an amide condensation reaction of compound (7). The amide condensation reaction can be carried out by a method similar to that of Step 5.

Step 8: Deprotection

Compound (9) can be produced by removing the protective group for a tropane ring nitrogen atom of compound (8). Deprotection can be carried out by a method similar to that of Step 2.

Step 9: Alkylation

Compound (Ia) can be produced by an alkylation reaction of compound (9). The alkylation reaction can be carried out by a method similar to that of Step 3.

Production Method 2

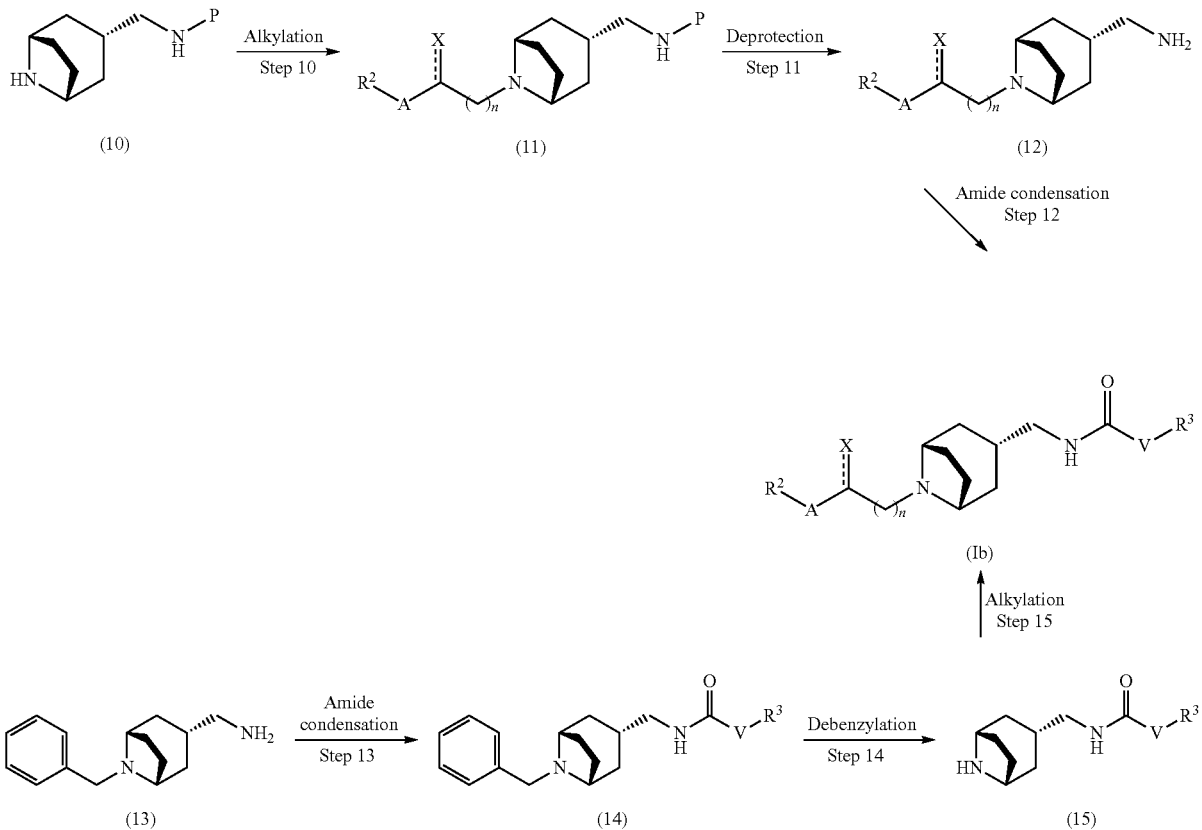

wherein R², R³, V, X, A, n, P, and a doublet containing a dotted line respectively mean the same as defined above.

Step 10: Alkylation

Compound (11) can be produced by an alkylation reaction of compound (10). The present step can be carried out by a method similar to that of Step 3.

Step 11: Deprotection

Compound (12) can be produced by removing a protective group for an amino group of compound (11). Deprotection of an amino group can be carried out by a method similar to that of Step 2.

Step 12: Amide Condensation

Compound (Ib) can be produced by a known method for converting an amino group of compound (12) to an amide structure, for example, an amide condensation reaction. The amide condensation reaction can be carried out by a method similar to that of Step 5, by replacing the amine compound to be used in Step 5 with a corresponding carboxylic acid compound or a carboxylic acid chloride (provided that in a case in which the present reagent is used, a condensing agent is not needed).

Meanwhile, the carboxylic acid compound and the carboxylic acid chloride may be commercially available products, or can be produced by known methods.

Step 13: Amide Condensation

Compound (14) can be produced by an amide condensation reaction of compound (13). The present step can be carried out by a method similar to that of Step 12.

Step 14: Debenzylation

Compound (15) can be produced by debenzylation of compound (14). The present step can be carried out by a method similar to that of Step 2.

Step 15: Alkylation

Compound (Ib) can be produced by an alkylation reaction of compound (15). The present step can be carried out by a method similar to that of Step 3.

Production Method 3

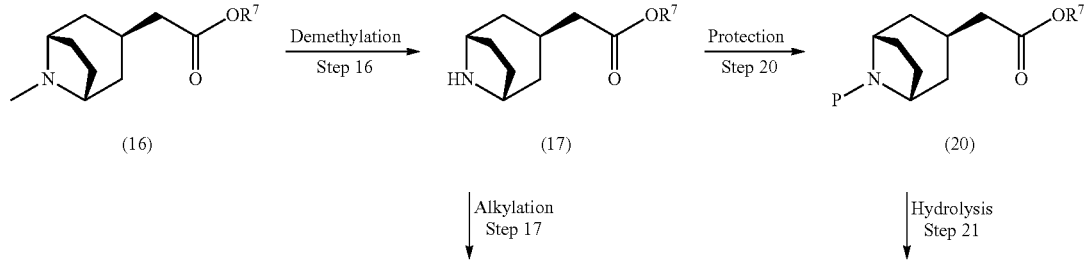

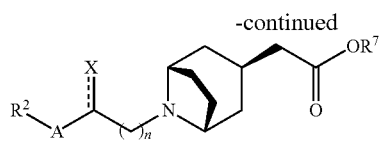
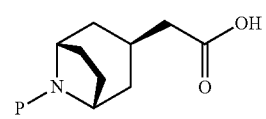
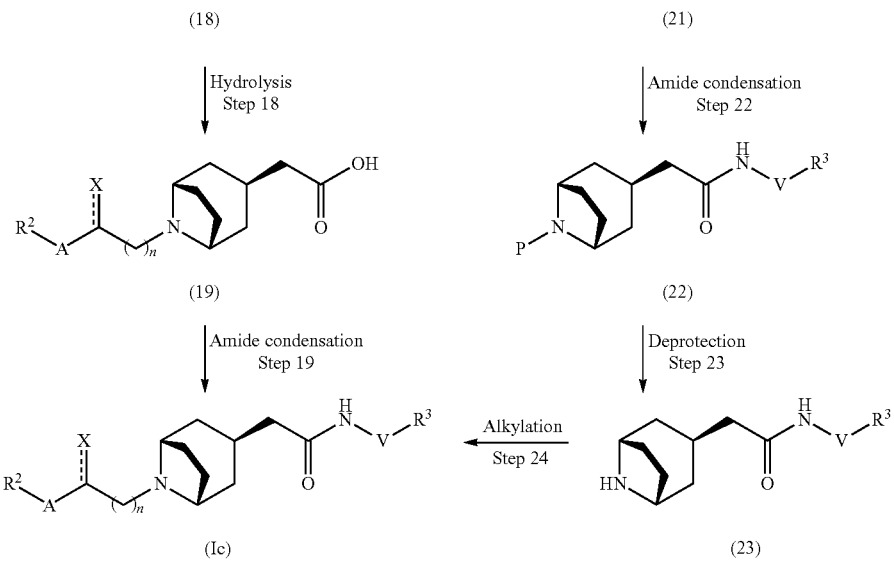

wherein $R^2$, $R^3$, V, X, A, n, $R^7$, P, and a doublet containing a dotted line respectively mean the same as defined above.

Step 16: Demethylation

Compound (17) can be produced by a demethylation reaction of compound (16). The present step can be carried out by a method similar to that of Step 2.

Step 17: Alkylation

Compound (18) can be produced by an alkylation reaction of compound (17). The present step can be carried out by a method similar to that of Step 3.

Step 18: Hydrolysis

Compound (19) can be produced by a hydrolysis reaction of compound (18). The hydrolysis reaction can be carried out by a method similar to that of Step 4.

Step 19: Amide Condensation

Compound (Ic) can be produced by an amide condensation reaction of compound (19). The present step can be carried out by a method similar to that of Step 5.

Step 20: Protection

Compound (20) can be produced by causing compound (17) to react with a protective group-introducing agent in an inert solvent in the presence or absence of a base. Examples of the protective group-introducing agent include di-tert-butyl dicarbonate ($Boc_2O$) and benzyl chloroformate (Cbz-Cl), and the protective group-introducing agent can be appropriately selected for use from the methods described in T. W. Greene and P. G. Wuts, "Greene's Protective Groups in Organic Synthesis (Fourth Edition)" (John Wiley & Sons, Inc.). For example, in a case in which a Boc group is introduced as a protective group P, organic amines such as pyridine and triethylamine, alkali metal hydroxides, and alkali metal carbonates can be used as bases. Examples of the inert solvent that can be used include ethers, nitriles, DMF, alcohol, DMSO, halogenated hydrocarbons such as dichloromethane and 1,2-dichloroethane, water, and mixtures thereof. The reaction temperature is preferably in the range of 0° C. to temperature for heating reflux, and the reaction time is preferably 0.5 to 72 hours.

Step 21: Hydrolysis

Compound (21) can be produced by a hydrolysis reaction of compound (20). The hydrolysis reaction can be carried out by a method similar to that of Step 4.

Step 22: Amide Condensation

Compound (22) can be produced by an amide condensation reaction of compound (21). The present step can be carried out by a method similar to that of Step 5.

Step 23: Deprotection

Compound (23) can be produced by deprotection of the protective group for a tropane ring nitrogen atom of compound (22) The present step can be carried out by a method similar to that of Step 2.

Step 24: Alkylation

Compound (Ic) can be produced by an alkylation reaction of compound (23). The present step can be carried out by a method similar to that of Step 3.

Production Method 4

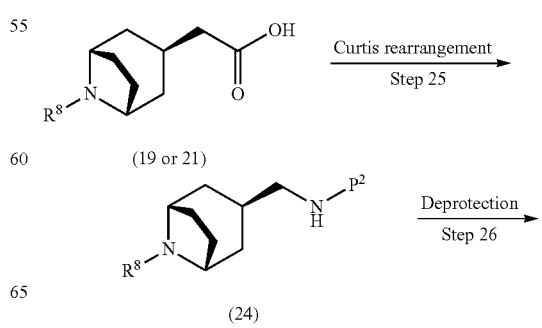

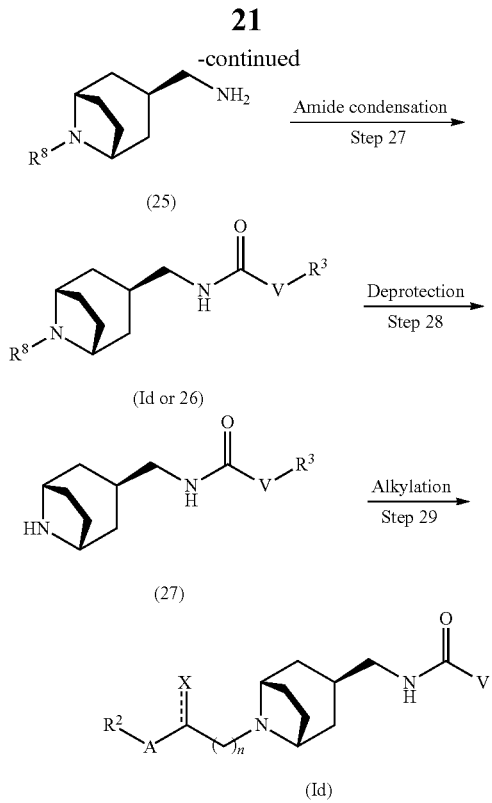

(25)

(Id or 26)

(27)

(Id)

wherein $R^8$ represents formula: —$(CH_2)_n$—C(=X)-A-$R^2$, —$(CH_2)_n$—CH(X)-A-$R^2$, or P; and $R^2$, $R^3$, V, X, A, n, P, and a doublet containing a dotted line respectively mean the same as defined above.

Step 25: Curtius Rearrangement

Compound (24) can be produced by a Curtius rearrangement reaction of compound (19) or compound (21). The Curtius rearrangement reaction can be carried out by, for example, activating compound (19) or compound (21) in the presence of an activator, a base, and an inert solvent, subsequently causing compound (19) or compound (21) with an azide group-introducing agent to obtain an acid azide, converting the acid azide to an isocyanate, and then treating the isocyanate with a corresponding alcohol in the presence or absence of an inert solvent. Regarding the activator, for example, thionyl chloride, oxalyl chloride, or ethyl chloroformate can be used. Regarding the base, an organic amine such as triethylamine or N-ethyldiisopropylamine can be used. Regarding the azide group-introducing agent, for example, sodium azide, trimethylsilyl azide, or diphenylphosphoryl azide (however, in the case of using the present reagent; a stage of activation is not needed) can be used. Examples of the solvent that can be used include ethers, DMF, halogenated carbons, nitriles, aromatic hydrocarbons, water, and mixtures thereof, and examples of the corresponding alcohol that can be used include methanol, ethanol, tert-butyl alcohol, and benzyl alcohol. The reaction temperature is preferably in the range of 0° C. to temperature for heating reflux, and the reaction time is preferably 1 to 168 hours.

Step 26: Deprotection

Compound (25) can be produced by removing the protective group for an amino group of compound (24). The present step can be carried out by a method similar to that of Step 2.

Step 27: Amide Condensation

Compound (Id) or compound (26) can be produced by an amide condensation reaction of compound (25). The present step can be carried out by a method similar to that of Step 12.

Step 28: Deprotection

In a case in which $R^8$ is P, compound (27) can be produced by removing the protective group of a tropane ring nitrogen atom of compound (26). The present step can be carried out by a method similar to that of Step 2.

Step 29: Alkylation

Compound (Id) can be produced by an alkylation reaction of compound (27). The alkylation reaction can be carried out by a method similar to that of Step 3.

Production Method 5

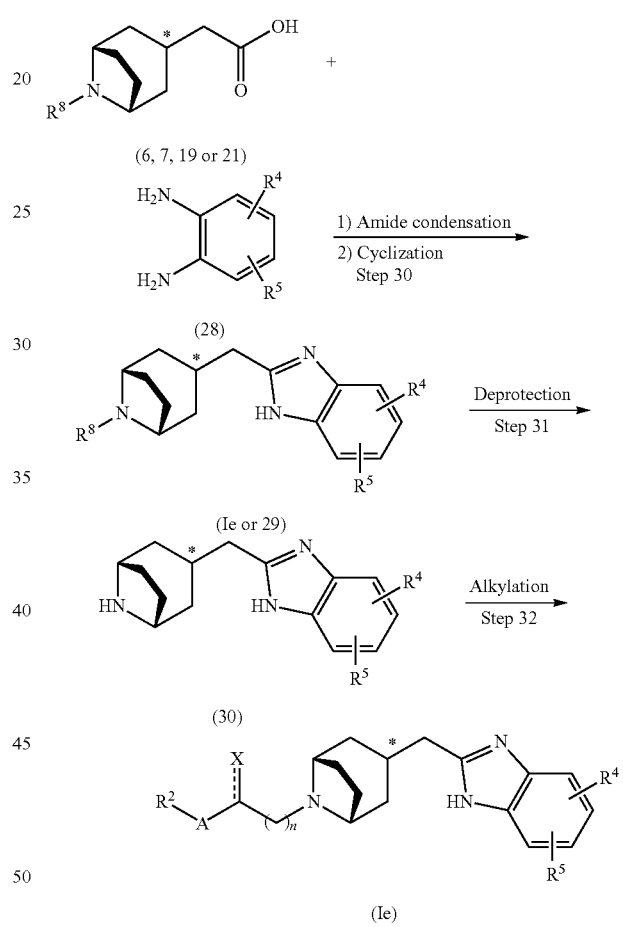

wherein $R^8$ represents formula: —$(CH_2)_n$—C(=X)-A-$R^2$, —$(CH_2)_n$—CH(X)-A-$R^2$, or P; $R^2$, $R^4$, $R^5$, X, A, n, and a doublet containing a dotted line respectively mean the same as defined above; and P represents a protective group of an amino group.

Step 30: Amide Condensation and Subsequent Cyclization

Compound (Ie) or compound (29) can be produced by an amide condensation reaction between compound (6), compound (7), compound (19), compound (21) and compound (28), and a subsequent cyclization reaction.

The amide condensation reaction can be carried out by a method similar to that of Step 5.

The subsequent cyclization reaction can be carried out by, for example, causing the reaction in the presence of an acid catalyst and in the presence or absence of an inert solvent. The reaction is carried out by, for example, heating and stirring, or by a method of irradiating the system with microwaves. Regarding the acid catalyst, carboxylic acids such as acetic acid, formic acid, and trifluoroacetic acid; sulfonic acids such as p-toluenesulfonic acid; inorganic acids such as hydrochloric acid and sulfuric acid can be used. Examples of the inert solvent that can be used include aromatic hydrocarbons such as toluene and xylene; ethers; chlorinated hydrocarbons; DMF, water, and mixtures thereof can be used. The reaction temperature is preferably in the range of 40° C. to 200° C., and the reaction time is preferably 0.5 to 48 hours.

Step 31: Deprotection

In a case in which $R^8$ is P, compound (30) can be produced by removing the protective group for a tropane ring nitrogen atom of compound (29). The present step can be carried out by a method similar to that of Step 2.

Step 32: Alkylation

Compound (Ie) can be produced by an alkylation reaction of compound (30). The alkylation reaction can be carried out by a method similar to that of Step 3.

The compound of the present invention thus obtainable shows excellent antagonistic activity against T-type calcium channels, and the compound is stable in the body, is highly safe in view of, for example, genotoxicity risk, and is useful as a prophylactic and therapeutic agent for various diseases on which T-type calcium channels act in animals including human beings. Examples of the diseases that can be prevented or treated by the antagonistic activity against T-type calcium channels include hypertension, atrial fibrillation, arrhythmia, cardiac hypertrophy, cardiac failure, renal dysfunction, pain, epilepsy, sleep disorder, obesity, and cancers.

In a case in which the compound of the present invention or a salt thereof is used as a pharmaceutical agent, the pharmaceutical agent can be administered orally or parenterally. In the dosage form for administration, for example, an excipient, a binder, a buffer agent, a thickening agent, a stabilizer, an emulsifier, a dispersant, a suspending agent, and an antiseptic agent can be added as pharmaceutically acceptable additives, and the dosage form can be formulated by any conventional method.

Examples of a preparation for oral administration include tablets (including sugar-coated tablets and film-coated tablets), pills, granules, powders, capsules (including soft capsules), syrups, emulsions, and suspensions. This preparation for oral administration can be produced according to a known method, by incorporating additives that are conventionally used in the field of formulation. Examples of such additives include excipients such as lactose, mannitol, and anhydrous calcium hydrogen phosphate; binders such as hydroxypropyl cellulose, methyl cellulose, and polyvinylpyrrolidone; disintegrants such as starch and carboxymethyl cellulose; and lubricating agents such as magnesium stearate and talc.

The pharmaceutical agent can be administered as, for example, a parenterally injectable preparation, a preparation for rectal administration, or a topical administration agent, and among them, an injectable preparation is preferred. Examples of the injectable preparation include a sterilized solution or suspension. Such an injectable preparation is produced by, for example, dissolving or suspending the compound of the present invention or a pharmaceutically acceptable salt thereof in the water for injection according to the Japanese Pharmacopoeia. If necessary, for example, an isotonizing agent such as sodium chloride; a buffer agent such as sodium dihydrogen phosphate or sodium monohydrogen phosphate; and a dissolution aid may be incorporated. Furthermore, an injectable preparation of a type that can be dissolved at the time of use (powder filling or freeze-drying) can be produced, and in this case, the injectable preparation can be produced by a conventional method by adding excipients such as mannitol and lactose.

Examples of the preparation for rectal administration include a suppository. A suppository is produced by, for example, dissolving or suspending the compound of the present invention or a pharmaceutically acceptable salt thereof in a base such as cacao fats or macrogol, and then molding the solution or suspension using a template. Furthermore, a liquid or a cream is inserted into a container for injection, and can be used as a preparation for rectal administration.

Examples of the preparation for topical administration include a liquid preparation, an eye drop, a cream, an ointment, a gel preparation, a spray preparation, and a powder preparation. A liquid preparation can be produced by adding the compound of the present invention or a pharmaceutically acceptable salt thereof to water, and adding, for example, a stabilizer, a solubilizing agent, a thickening agent, a dispersant, or a suspending agent thereto as necessary. Regarding this thickening agent, for example, gelatin, sodium hyaluronate, a polymeric dextran, sodium alginate, or sodium chondroitin sulfate can be used. An eye drop can be produced by adding an antiseptic agent in addition to a buffer agent, a pH adjusting agent, and an isotonizing agent. A cream and an ointment can be produced using an aqueous or oily base, for example, water, liquid paraffin, plant oil (for example, peanut oil or castor oil), or macrogol. A gel preparation can be produced by a known method, using gelatin, pectin, carrageenan, agar, tragacanth gum, alginate, a cellulose ether (for example, methyl cellulose or sodium carboxymethyl cellulose), a pectin derivative, a polyacrylate, a polymethacrylate, polyvinyl alcohol, and polyvinylpyrrolidone. A spray preparation can be produced by dissolving or suspending the compound of the present invention or a pharmaceutically acceptable salt thereof in, for example, water, and then introducing the resultant into a container for spray. In the case of producing a powder preparation, the compound of the present invention or a pharmaceutically acceptable salt thereof can be used directly, or the powder preparation can be produced by mixing the compound or the salt with appropriate excipients.

The dose amount per day of the compound of the present invention for an adult may vary depending on, for example, the symptoms, body weight and age of the patient, the type of the compound, and the route of administration; however, in the case of oral administration, the dose is adequately about 0.01 to 1,000 mg, and preferably about 0.1 to 300 mg. In the case of parenteral administration, an amount equivalent to one-tenth to a half of the amount used in the case of oral administration may be administered. Such a dosage can be appropriately increased or decreased in accordance with, for example, the symptoms, body weight, and age of the patient.

EXAMPLES

Hereinafter, the present invention will be specifically described by way of Examples; however, the present invention is not intended to be limited to these embodiments.

Reference Example 1

Ethyl [(exo)-8-tert-butoxycarbonyl-8-azabicyclo [3.2.1]octan-3-yl]acetate tertButyl 3-ethoxycarbonylmethylene-8-azabicyclo [3.2.1]octane-8-carboxylate (WO 2007/079239) (50.3 g)

was dissolved in ethanol/water (7:2) (567 mL), a 5% rhodium/alumina powder (12.6 g) was added thereto, and the mixture was stirred for 27 hours at room temperature in a hydrogen atmosphere. Insolubles were filtered through Celite, and the filtrate was distilled off under reduced pressure. Subsequently, saturated brine was added to the residue, and extracted with ethyl acetate. The organic layer was dried over anhydrous magnesium sulfate, and then the solvent was distilled off under reduced pressure, to yield the title compound (51.7 g) as a crude product.

$^1$H-NMR (CDCl$_3$)δ:4.35-4.02 (2H, m), 4.12 (2H, q, J=7.1 Hz), 2.40-2.21 (1H, m), 2.21-2.08 (2H, m), 2.06-1.83 (2H, m), 1.74-1.37 (6H, m), 1.46 (9H, s), 1.25 (3H, t, J=7.1 Hz).

ESI+APCI-MS Found:m/z 198 (M−Boc+2H)$^+$

Reference Example 2

[(exo)-8-tert-Butoxycarbonyl-8-azabicyclo[3.2.1]octan-3-yl]acetic acid

The compound of Reference Example 1 (50.6 g) was dissolved in methanol (340 mL), a 1 mol/L aqueous solution of sodium hydroxide (255 mL) was added thereto, and the mixture was stirred for 1 hour under heating at 40° C. Methanol was distilled off under reduced pressure, and then the aqueous layer was washed with diethyl ether. 1 mol/L Hydrochloric acid was added to the aqueous layer to adjust the pH to about 2, and the mixture was stirred for 1 hour at room temperature. After the mixture was cooled on ice, a precipitate was collected by filtration, and was washed sequentially with cold water and heptane, to yield the title compound (42.7 g) was obtained.

$^1$H-NMR (CDCl$_3$)δ:4.36-4.03 (2H, m), 2.41-2.16 (3H, m), 2.01-1.86 (2H, m), 1.72-1.58 (4H, m), 1.52-1.27 (2H, m), 1.46 (9H, s).

ESI+APCI-MS Found:m/z 268 (M−H)$^-$

Reference Example 3

Ethyl [(exo)-8-azabicyclo[3.2.1]octan-3-yl]acetate hydrochloride

The compound of Reference Example 2 (2.51 g) was dissolved in a 2 mol/L ethanol solution of hydrogen chloride (23 mL), and the solution was stirred for 2 hours while heated to reflux. The reaction solvent was distilled off under reduced pressure, and thus the title compound (2.14 g) was obtained as a crude product.

$^1$H-NMR (CDCl$_3$) δ:9.77-9.33 (2H, m), 4.12 (2H, q, J=7.1 Hz), 4.09-3.98 (2H, m), 2.40-2.19 (5H, m), 2.03-1.53 (6H, m), 1.25 (3H, t, J=7.1 Hz).

ESI+APCI-MS Found:m/z 198 (M+H)$^+$

Reference Example 4

Ethyl [(exo)-8-(tert-butylcarbamoyl)methyl-8-azabicyclo[3.2.1]octan-3-yl]acetate The compound of Reference Example 3 (2.14 g) was dissolved in 1,4-dioxane (hereinafter, dioxane) (37 mL), and 2-chloro-N-tert-butylacetamide (1.37 g) and DBU (3.01 mL) were added thereto. The mixture was stirred for 17 hours under heating at 50° C. The reaction solvent was distilled off under reduced pressure, subsequently water was added to the residue, and extracted with ethyl acetate. The organic layer was extracted with 1 mol/L hydrochloric acid, and the aqueous layer was adjusted to pH 9 to 10 with a 1 mol/L aqueous solution of sodium hydroxide. The aqueous layer was subjected to extraction again with ethyl acetate. The organic layer was washed with saturated brine and dried over anhydrous magnesium sulfate, and the solvent was distilled off under reduced pressure. A residue thus obtained was purified by silica gel column chromatography (1% to 10% methanol/chloroform), and thus the title compound (2.45 g) was obtained.

$^1$H-NMR (CDCl$_3$)δ:7.50-7.39 (1H, m), 4.12 (2H, q, J=7.1 Hz), 3.14-3.05 (2H, m), 2.84 (2H, s), 2.22-2.01 (3H, m), 2.00-1.80 (2H, m), 1.69-1.52 (4H, m), 1.40-1.29 (2H, m), 1.37 (9H, s), 1.26 (3H, t, J=7.1 Hz).

ESI+APCI-MS Found:m/z 311 (M+H)$^+$

Reference Example 5

[(exo)-8-(tert-Butylcarbamoyl)methyl-8-azabicyclo[3.2.1]octan-3-yl]acetic acid hydrochloride The compound of Reference Example 4 (2.43 g) was dissolved in ethanol (8 mL), a 2 mol/L aqueous solution of sodium hydroxide (4.50 mL) was added thereto, and the mixture was stirred for 1.5 hours under heating at 40° C. Concentrated hydrochloric acid (1.49 mL) was added to the reaction solution, and the solvent was distilled off under reduced pressure. A residue thus obtained was suspended in ethanol (16 mL), and the suspension was stirred for 10 minutes at room temperature. A precipitate was filtered and washed with ethanol, and then the filtrate was distilled off under reduced pressure. Ethyl acetate was added to a residue thus obtained, and the mixture was stirred for 15 minutes at room temperature. Subsequently, a precipitate was collected by filtration and washed with ethyl acetate, and thus the title compound (1.96 g) was obtained.

$^1$H-NMR (DMSO-d$_6$)δ:12.24 (1H, brs), 9.47 (1H, brs), 8.31-8.15 (1H, m), 4.10-3.63 (4H, m), 3.33 (2H, s), 2.34-2.02 (5H, m), 1.98-1.54 (4H, m), 1.30 (9H, s). ESI+APCI-MS Found:m/z 283 (M+H)$^+$ Reference Example 6 tert-Butyl (exo)-3-[(adamantan-1-yl)carbamoyl]methyl-8-azabicyclo[3.2.1]octane-8-carboxylate The compound of Reference Example 2 (180 mg) was dissolved in dichloromethane (2 mL), and 1-adamantaneamine (121 mg) and HATU (280 mg) were added thereto. Subsequently, N-ethyldiisopropylamine (343 µL) was added to the mixture, and the mixture was stirred for 1 hour at room temperature. The reaction solvent was distilled off under reduced pressure, and a residue thus obtained was purified by silica gel column chromatography (1% to 5% methanol/chloroform), to yield the title compound (141 mg).

$^1$H-NMR (CDCl$_3$)δ:5.07 (1H, brs), 4.32-4.02 (2H, m), 2.48-2.22 (1H, m), 2.16-2.02 (3H, m), 2.00-1.82 (10H, m), 1.76-1.52 (10H, m), 1.46 (9H, s), 1.46-1.24 (2H, m).

ESI+APCI-MS Found:m/z 403 (M+H)$^+$

Reference Example 7

N-(Adamantan-1-yl)-2-[(exo)-8-azabicyclo[3.2.1]octan-3-yl]acetamide hydrochloride The compound of Reference Example 6 (140 mg) was dissolved in dioxane (2 mL), and a 4 mol/L dioxane solution of hydrogen chloride (3 mL) was added thereto. The mixture was stirred for 1 hour at room temperature. The reaction solvent was distilled off under reduced pressure, and the title compound (118 mg) was obtained as a crude product.

$^1$H-NMR (CD$_3$OD)δ:4.03-3.92 (2H, m), 2.41-1.99 (18H, m), 1.79-1.61 (8H, m). ESI+APCI-MS Found:m/z 303 (M+H)$^+$ Reference Example 8 tert-Butyl N-[(exo)-8-(tert-butylcarbamoyl)methyl-8-azabicyclo[3.2.1]octan-3-yl]methylcarbamate tert-Butyl N-[(exo)-8-azabicyclo[3.2.1]octan-3-yl]methylcarbamate (US 2005/80085) (2.30 g) was dissolved in dioxane (38 mL), and 2-chloro-N-tert-butylacetamide (1.51 g) and DBU (1.58 mL) were added to the solution. The mixture was stirred for 16 hours under heating at 40° C. The reaction solvent was distilled off under reduced pressure, water was added to the residue, and extracted with ethyl acetate. The organic layer was washed sequentially with a saturated aqueous solution of sodium hydrogen carbonate and saturated brine, and then was dried over anhydrous sodium sulfate. The solvent was distilled off under reduced pressure. A residue thus obtained was purified by silica gel column chromatography (1% to 10% methanol/chloroform), and thus the title compound (3.26 g) was obtained.

$^1$H-NMR (CDCl$_3$)δ:7.42 (1H, brs), 4.61-4.43 (1H, m), 3.16-3.07 (2H, m), 3.02-2.93 (2H, m), 2.84 (2H, s), 1.96-1.67 (3H, m), 1.60-1.25 (6H, m), 1.44 (9H, s), 1.37 (9H, s).

ESI+APCI-MS Found:m/z 354 (M+H)$^+$

Reference Example 9

N-tert-Butyl-2-[(exo)-3-aminomethyl-8-azabicyclo[3.2.1]octan-8-yl]acetamide dihydrochloride The compound of Reference Example 8 (3.17 g) was dissolved in dioxane (18 mL), and a 4 mol/L dioxane solution of hydrogen chloride (33.7 mL) was added thereto. The mixture was stirred for 2 hours at room temperature. The reaction solvent was distilled off under reduced pressure, a residue thus obtained was suspended in ethyl acetate, and the suspension was stirred for 10 minutes at room temperature. A precipitate was collected by filtration and washed with ethyl acetate, and thus the title compound (2.35 g) was obtained.

$^1$H-NMR (CD$_3$OD)δ:4.08-4.02 (2H, m), 3.74 (2H, s), 2.94-2.86 (2H, m), 2.36-2.20 (3H, m), 2.10-1.95 (4H, m), 1.88-1.77 (2H, m), 1.36 (9H, s). ESI+APCI-MS Found:m/z 254 (M+H)$^+$ Reference Example 10

N-[(exo)-8-Benzyl-8-azabicyclo[3.2.1]octan-3-yl]methyl-3-chloro-5-fluorobenzamide The title compound (1.67 g) was obtained by a method similar to that of Reference Example 6, using [(exo)-8-benzyl-8-azabicyclo[3.2.1]octan-3-yl]methylamine (US 2002/0165241) (1.20 g) and 3-chloro-5-fluorobenzoic acid (955 mg).

$^1$H-NMR (CDCl$_3$)δ:7.52-7.49 (1H, m), 7.41-7.19 (7H, m), 6.20-6.00 (1H, m), 3.53 (2H, s), 3.32 (2H, dd, J=6.3, 6.3 Hz), 3.27-3.17 (2H, m), 2.10-1.89 (3H, m), 1.69-1.43 (6H, m).

ESI+APCI-MS Found:m/z 387 (M+H)$^+$

Reference Example 11

N-[(exo)-8-Azabicyclo[3.2.1]octan-3-yl]methyl-3-chloro-5-fluorobenzamide

The compound of Reference Example 10 (1.54 g) was dissolved in dichloromethane (25 mL), and 1-chloroethyl chloroformate (1.08 mL) was added thereto. The mixture was stirred for 7 hours while being heated to reflux. The reaction solvent was distilled off under reduced pressure, and then methanol was added to the residue. The mixture was stirred for 2 hours while being heated to reflux. The reaction solvent was distilled off under reduced pressure, and a residue thus obtained was purified by silica gel column chromatography (NH silica gel, 1% to 15% methanol/chloroform), to yield the title compound (813 mg).

$^1$H-NMR (CDCl$_3$)δ:7.54-7.48 (1H, m), 7.43-7.34 (1H, m), 7.26-7.18 (1H, m), 6.25-6.07 (1H, m), 3.60-3.50 (2H, m), 3.30 (2H, dd, J=6.2, 6.2 Hz), 2.14-1.94 (1H, m), 1.86-1.51 (6H, m), 1.42-1.26 (2H, m).

ESI+APCI-MS Found:m/z 297 (M+H)$^+$

Reference Example 12 tert-Butyl (exo)-3-(5,6-dihydro-1H-[1,4]dioxino[2,3-e]benzimidazol-2-yl)methyl-8-azabicyclo[3.2.1]octane-8-carboxylate The compound of Reference Example 2 (304 mg) was dissolved in acetonitrile (5 mL), and 2,3-dihydrobenzo[1,4]dioxin-5,6-diamine dihydrochloride (284 mg) and PyBOP (646 mg) were added thereto under ice cooling. Subsequently, triethylamine (519 μL) was added to the mixture, and the mixture was stirred for 1.5 hours at room temperature. The reaction solvent was distilled off under reduced pressure, a saturated aqueous solution of sodium hydrogen carbonate was added to the residue, and extracted with chloroform. The organic layer was dried over anhydrous sodium sulfate, and the solvent was distilled off under reduced pressure. A residue thus obtained was purified by silica gel column chromatography (0% to 10% methanol/chloroform), and thus a crude product (333 mg) was obtained.

The crude product (333 mg) thus obtained was dissolved in acetic acid (3 mL), and the solution was stirred for 2 hours under heating at 90° C. The reaction solvent was distilled off under reduced pressure, and a residue thus obtained was purified by silica gel column chromatography (0% to 12% methanol/chloroform), to yield the title compound (302 mg).

$^1$H-NMR (CDCl$_3$)δ:6.99 (1H, d, J=8.6 Hz), 6.79 (1H, d, J=8.6 Hz), 4.43-4.27 (4H, m), 4.27-4.09 (2H, m), 2.81-2.62 (2H, m), 2.57-2.36 (1H, m), 2.01-1.86 (2H, m), 1.71-1.37 (6H, m), 1.47 (9H, s).

ESI+APCI-MS Found:m/z 400 (M+H)$^+$

Reference Example 13

2-[(exo)-8-Azabicyclo[3.2.1]octan-3-yl]methyl-5,6-dihydro-1H-[1,4]dioxino[2,3-e]benzimidazole dihydrochloride The compound of Reference Example 12 (300 mg) was dissolved in dioxane (3 mL), and a 4 mol/L dioxane solution of hydrogen chloride (1.88 mL) was added thereto. The mixture was stirred for 2 hours at room temperature. The reaction solvent was distilled off under reduced pressure, and ethyl acetate/diethyl ether (1:1) was added to a residue thus obtained. The mixture was stirred for 10 minutes at room temperature. A precipitate was collected by filtration and washed with diethyl ether, and thus the title compound (230 mg) was obtained.

$^1$H-NMR (DMSO-d$_6$)δ:9.15-8.73 (2H, m), 7.20 (1H, d, J=8.8 Hz), 7.06 (1H, d, J=8.8 Hz), 4.51-4.33 (4H, m), 3.99-3.87 (2H, m), 3.02-2.93 (2H, m), 2.60-2.38 (1H, m), 2.05-1.57 (8H, m).

ESI+APCI-MS Found:m/z 300 (M+H)$^+$

Reference Example 14

Methyl [(endo)-8-azabicyclo[3.2.1]octan-3-yl]acetate hydrochloride

Methyl [(endo)-8-methyl-8-azabicyclo[3.2.1]octan-3-yl]acetate (Journal of Medicinal Chemistry, 2009, 52, 5241) (43.8 g) was dissolved in THF (577 mL), and 1-chloroethyl chloroformate (60.4 mL) was added thereto. The mixture was stirred for 1.5 hours while being heated to reflux. The reaction solvent was distilled off under reduced pressure, methanol (577 mL) was added thereto, and the mixture was stirred for 1.5 hours while being heated to reflux. The reaction solvent was distilled off under reduced pressure, subsequently ethyl acetate was added thereto, and the mixture was stirred at room temperature. A precipitate was collected by filtration, and the title compound (42.0 g) was obtained.

$^1$H-NMR (CD$_3$OD)δ:4.04-3.90 (2H, m), 3.67 (3H, s), 2.70-2.55 (2H, m), 2.47-1.96 (7H, m), 1.78-1.63 (2H, m).

ESI+APCI-MS Found:m/z 184 (M+H)$^+$

Reference Example 15

Methyl [(endo)-8-(tert-butylcarbamoyl)methyl-8-azabicyclo[3.2.1]octan-3-yl]acetate The compound of Reference Example 14 (35.0 g) was suspended in dioxane (636 mL), and 2-chloro-N-tert-butylacetamide (23.8 g) and DBU (52.4 mL) were added thereto. The mixture was stirred for 2 days at room temperature. Insolubles were filtered, and the filtrate was distilled off under reduced pressure. Subsequently, a saturated aqueous solution of ammonium chloride was added to the residue, and extracted with chloroform. The organic layer was washed sequentially with water and saturated brine, and then was dried over anhydrous sodium sulfate. The solvent was distilled off under reduced pressure. A residue thus obtained was purified by silica gel column chromatography (NH silica gel, 5% to 20% ethyl acetate/hexane), and thus the title compound (41.7 g) was obtained.

$^1$H-NMR (CDCl$_3$)δ:7.45 (1H, brs), 3.67 (3H, s), 3.15-3.02 (2H, m), 2.82 (2H, s), 2.50-2.40 (2H, m), 2.36-2.22 (1H, m), 2.20-2.05 (2H, m), 2.03-1.87 (2H, m), 1.73-1.56 (2H, m), 1.41-1.27 (2H, m), 1.37 (9H, s).

ESI+APCI-MS Found:m/z 297 (M+H)$^+$

Reference Example 16

[(endo)-8-(tert-Butylcarbamoyl)methyl-8-azabicyclo[3.2.1]octan-3-yl]acetic acid hydrochloride The title compound (35.8 g) was obtained by a method similar to that of Reference Example 5, using the compound of Reference Example 15 (34.7 g).

$^1$H-NMR (CD$_3$OD) δ:4.05-3.83 (2H, m), 3.74 (2H, s), 2.69-2.54 (2H, m), 2.54-2.34 (3H, m), 2.34-2.05 (4H, m), 1.88-1.74 (2H, m), 1.36 (9H, s).

ESI+APCI-MS Found:m/z 283 (M+H)$^+$

Reference Example 17

Methyl [(endo)-8-tert-butoxycarbonyl-8-azabicyclo[3.2.1]octan-3-yl]acetate

The compound of Reference Example 14 (2.08 g) was dissolved in dichloromethane (20 mL), and Boc$_2$O (2.48 g) and triethylamine (3.96 mL) were added thereto. The mixture was stirred for 5.5 hours at room temperature. The reaction solvent was distilled off under reduced pressure, 1 mol/L hydrochloric acid was added to the residue, and extracted with ethyl acetate. The organic layer was washed with saturated brine and then dried over anhydrous sodium sulfate, and thus the title compound (2.10 g) was obtained as a crude product.

$^1$H-NMR (CDCl$_3$)δ:4.31-4.05 (2H, m), 3.69-3.64 (3H, m), 2.54-2.43 (2H, m), 2.32-2.11 (3H, m), 2.08-1.89 (2H, m), 1.77-1.36 (4H, m), 1.46 (9H, s).

Reference Example 18

[(endo)-8-tert-Butoxycarbonyl-8-azabicyclo[3.2.1]octan-3-yl]acetic acid

The compound of Reference Example 17 (2.10 g) was dissolved in methanol (40 mL), and a 1 mol/L aqueous solution of sodium hydroxide (20 mL) was added thereto. The mixture was stirred for 2 hours under heating at 70° C. Methanol was distilled off under reduced pressure, and the aqueous layer was washed with diethyl ether. Subsequently, 1 mol/L hydrochloric acid was added to the aqueous layer to make the aqueous layer acidic, and extracted with ethyl acetate. The organic layer was dried over anhydrous sodium sulfate, and the solvent was distilled off under reduced pressure, to yield the title compound (2.00 g).

$^1$H-NMR (CDCl$_3$)δ:4.34-4.04 (2H, m), 2.56-2.46 (2H, m), 2.38-2.11 (3H, m), 2.07-1.90 (2H, m), 1.75-1.58 (2H, m), 1.46 (9H, s), 1.38-1.21 (2H, m).

ESI+APCI-MS Found:m/z 170 (M-Boc+2H)$^+$

Reference Example 19 tert-Butyl (endo)-3-[(adamantan-1-yl)carbamoyl]methyl-8-azabicyclo[3.2.1]octane-8-carboxylate The title compound (135 mg) was obtained by a method similar to that of Reference Example 6, using the compound of Reference Example 18 (100 mg) and 1-adamantaneamine (67 mg).

$^1$H-NMR (CDCl$_3$)δ:5.06 (1H, brs), 4.36-4.00 (2H, m), 2.40-1.54 (24H, m), 1.46 (9H, s), 1.35-1.21 (2H, m).

ESI+APCI-MS Found:m/z 303 (M-Boc+2H)$^+$

Reference Example 20

N-(Adamantan-1-yl)-2-[(endo)-8-azabicyclo[3.2.1]octan-3-yl]acetamide trifluoroacetate The compound of Reference Example 19 (597 mg) was dissolved in dichloromethane (20 mL), and trifluoroacetic acid (5.5 mL) was added thereto. The mixture was stirred for 2 hours at room temperature. The reaction solvent was distilled off under reduced pressure, and the title compound (498 mg) was obtained as a crude product.

$^1$H-NMR (CD$_3$OD)δ:4.03-3.91 (2H, m), 2.53-1.92 (18H, m), 1.80-1.59 (8H, m).

ESI+APCI-MS Found:m/z 303 (M+H)$^+$

Reference Example 21

N-(Adamantan-1-yl)-2-[(endo)-8-azabicyclo[3.2.1]octan-3-yl]acetamide hydrochloride The title compound (100 mg) was obtained as a crude product by a method similar to that of Reference Example 7, using the compound of Reference Example 19 (135 mg).

$^1$H-NMR (CD$_3$OD)δ:4.03-3.91 (2H, m), 2.43-1.96 (18H, m), 1.78-1.61 (8H, m).

ESI+APCI-MS Found:m/z 303 (M+H)$^+$

Reference Example 22 tert-Butyl N-[(endo)-8-(tert-butylcarbamoyl)methyl-8-azabicyclo[3.2.1]octan-3-yl]methylcarbamate The compound of Reference Example 16 (1.00 g) was dissolved in tert-butyl alcohol (16 mL), and triethylamine (1.05 mL) and diphenylphosphoryl azide (DPPA) (811 µL) were added thereto. The mixture was stirred for 22 hours while being heated to reflux. The reaction solvent was distilled off under reduced pressure, water was added to the residue, and extracted with ethyl acetate. The organic layer was washed sequentially with a saturated aqueous solution of sodium hydrogen carbonate and saturated brine, and was dried over anhydrous sodium sulfate. The solvent was distilled off under reduced pressure. A residue thus obtained was purified by silica gel column chromatography (diol silica gel, 20% to 50% ethyl acetate/hexane), and thus the title compound (480 mg) was obtained.

$^1$H-NMR (CDCl$_3$)δ:7.45 (1H, brs), 4.64-4.43 (1H, m), 3.18 (2H, dd, J=7.2, 7.2 Hz), 3.12-3.02 (2H, m), 2.83 (2H, s), 2.08-1.88 (4H, m), 1.85-1.64 (3H, m), 1.53-1.30 (2H, m), 1.44 (9H, s), 1.37 (9H, s).

ESI+APCI-MS Found:m/z 354 (M+H)$^+$

Reference Example 23

N-tert-Butyl-2-[(endo)-3-aminomethyl-8-azabicyclo[3.2.1]octan-8-yl]acetamide dihydrochloride The title compound (770 mg) was obtained as a crude product by a method similar to that of Reference Example 9, using the compound of Reference Example 22 (880 mg).

$^1$H-NMR (CD$_3$OD)δ:7.88 (1H, brs), 4.03-3.94 (2H, m), 3.76-3.69 (2H, m), 3.26-3.11 (2H, m), 2.59-2.41 (2H, m), 2.40-2.16 (3H, m), 2.17-2.05 (2H, m), 1.46-1.28 (2H, m), 1.36 (9H, s).

ESI+APCI-MS Found:m/z254 (M+H)$^+$

Reference Example 24 tert-Butyl (endo)-3-[(benzyloxycarbonyl)amino]methyl-8-azabicyclo [3.2.1]octane-8-carboxylate The compound of Reference Example 18 (300 mg) was dissolved in benzyl alcohol (5 mL), and triethylamine (202 µL) and DPPA (288 µL) were added thereto. The mixture was stirred for 3 hours while being heated to reflux. DPPA (240 µL) was added thereto, and the mixture was further stirred for 1 hour while being heated to reflux. The reaction solvent was distilled off under reduced pressure, 0.5 mol/L hydrochloric acid was added to the residue, and extracted with ethyl acetate. The organic layer was washed sequentially with a 1 mol/L aqueous solution of sodium hydroxide and saturated brine, and then was dried over anhydrous sodium sulfate. The solvent was distilled off under reduced pressure. A residue thus obtained was purified by silica gel column chromatography (10% to 60% ethyl acetate/hexane), and thus the title compound (216 mg) was obtained.

$^1$H-NMR (CDCl$_3$) δ: 7.39-7.29 (5H, m), 5.10 (2H, s), 4.84-4.68 (1H, m), 4.28-4.06 (2H, m), 3.40-3.23 (2H, m), 2.24-1.90 (4H, m), 1.84-1.68 (3H, m), 1.46 (9H, s), 1.41-1.27 (2H, m).

ESI+APCI-MS Found:m/z 275 (M-Boc+2H)$^+$

Reference Example 25 tert-Butyl (endo)-3-aminomethyl-8-azabicyclo[3.2.1]octane-8-carboxylate

The compound of Reference Example 24 (206 mg) was dissolved in a 1:1 mixed liquid (3 mL) of ethanol and ethyl acetate, and 5% palladium-carbon (53% hydrated) (66.8 mg) was added thereto. The mixture was stirred for 14 hours at room temperature in a hydrogen atmosphere. Insolubles were filtered through Celite, and then the reaction solvent was distilled off under reduced pressure, to yield the title compound (128 mg).

$^1$H-NMR (CDCl$_3$)δ: 4.29-4.03 (2H, m), 2.75 (2H, d, J=7.7 Hz), 2.33-1.52 (7H, m), 1.46 (9H, s), 1.42-1.30 (4H, m).

Reference Example 26 tert-Butyl (endo)-3-[(adamantan-1-carbonyl)amino]methyl-8-azabicyclo[3.2.1]octane-8-carboxylate The compound of Reference Example 25 (128 mg) was dissolved in dichloromethane (2 mL), and N-ethyldiisopropylamine (111 µL) was added thereto. Subsequently, 1-adamantanecarboxylic acid chloride (118 mg) was added to the mixture under ice cooling, and the mixture was stirred for 1 hour at room temperature. The reaction solvent was distilled off under reduced pressure, and a residue thus obtained was purified by silica gel column chromatography (1% to 8% methanol/chloroform), to yield the title compound (180 mg).

$^1$H-NMR (CDCl$_3$)δ:5.90-5.54 (1H, m), 4.33-3.96 (2H, m), 3.56-3.21 (2H, m), 2.21-1.90 (8H, m), 1.89-1.63 (14H, m), 1.46 (9H, s), 1.38-1.26 (2H, m).

ESI+APCI-MS Found:m/z 437 (M+Cl)$^-$

Reference Example 27

N-[(endo)-8-Azabicyclo[3.2.1]octan-3-yl]methyladamantane-1-carboxamide hydrochloride The title compound (120 mg) was obtained as a crude product by a method similar to that of Reference Example 7, using the compound of Reference Example 26 (180 mg).

$^1$H-NMR (CD$_3$OD)δ:4.03-3.89 (2H, m), 3.35 (2H, d, J=8.4 Hz), 2.32-1.93 (10H, m), 1.92-1.66 (14H, m).

ESI+APCI-MS Found:m/z 303 (M+H)$^+$

Reference Example 28 tert-Butyl (endo)-3-(4-methyl-1H-benzimidazol-2-yl)methyl-8-azabicyclo[3.2.1]octane-8-carboxylate The title compound (760 mg) was obtained by a method similar to that of Reference Example 12, using the compound of Reference Example 18 (1.00 g) and 2,3-diaminotoluene (499 mg).

$^1$H-NMR (CDCl$_3$)δ:7.47-7.29 (1H, m), 7.19-7.06 (1H, m), 7.06-6.96 (1H, m), 4.39-4.00 (2H, m), 3.20-2.92 (2H, m), 2.57 (3H, s), 2.40-1.19 (9H, m), 1.45 (9H, s).

ESI+APCI-MS Found:m/z 356 (M+H)$^+$

Reference Example 29

2-[(endo)-8-Azabicyclo [3.2.1]octan-3-yl]methyl-4-methyl-1H-benzimidazole

The compound of Reference Example 28 (760 mg) was dissolved in ethanol (10 mL), and a 2 mol/L ethanol solution of hydrogen chloride (10 mL) was divided into three parts and added thereto. The mixture was stirred overnight at room temperature. The reaction solvent was distilled off under reduced pressure, and a saturated aqueous solution of sodium hydrogen carbonate was added to the residue. The mixture was washed with ethyl acetate, and the aqueous layer was distilled off under reduced pressure. A residue thus obtained was purified by silica gel column chromatography (NH silica gel, 11% to 17% methanol/chloroform), and thus the title compound (476 mg) was obtained.

$^1$H-NMR (D$_2$O)δ:7.49-7.40 (1H, m), 7.27-7.17 (1H, m), 7.17-7.05 (1H, m), 3.78-3.65 (2H, m), 3.19-3.07 (2H, m), 2.54 (3H, s), 2.53-2.35 (1H, m), 2.19-1.96 (6H, m), 1.60-1.47 (2H,

ESI+APCI-MS Found:m/z 256 (M+H)$^+$ m).

Example 1

2-[(exo)-8-(tert-Butylcarbamoyl)methyl-8-azabicyclo[3.2.1]octan-3-yl]-N-(3-chlorophenyl)acetamide

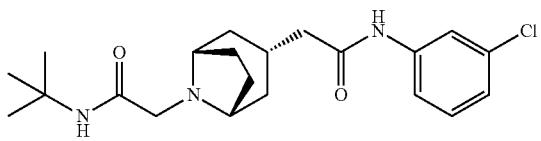 [SMILES: CC(C)(C)NC(=O)CN1[C@@H]2CC[C@H]1C[C@H](CC(=O)Nc1cccc(Cl)c1)C2]

The compound of Reference Example 5 (100 mg) was dissolved in dichloromethane (1 mL), and 3-chloroaniline (40 mg) and HATU (131 mg) were added thereto. Subsequently, triethylamine (131 μL) was added to the mixture, and the mixture was stirred for 14 hours at room temperature. The reaction solution was filtered through NH silica gel and washed with chloroform, and the filtrate was distilled off under reduced pressure. A residue thus obtained was purified by silica gel column chromatography (2% to 8% methanol/chloroform), and thus the title compound (91 mg) was obtained.

$^1$H-NMR (CDCl$_3$)δ:7.70-7.32 (4H, m), 7.29-7.18 (1H, m), 7.12-7.02 (1H, m), 3.17-3.07 (2H, m), 2.87 (2H, s), 2.28-2.18 (3H, m), 1.98-1.84 (2H, m), 1.75-1.57 (4H, m), 1.42-1.34 (2H, m), 1.37 (9H, s).

ESI+APCI-MS Found:m/z 392 (M+H)$^+$

Example Compounds 2 and 3 produced by a method similar to that of Example 1 using corresponding raw materials are shown in Table 1.

TABLE 1

| Ex. | Structural formula | $^1$H-NMR (CDCl$_3$) | ESI + APCI MS |
|---|---|---|---|
| 2 | | δ: 7.43 (1H, br s), 5.57 (1H, br s), 4.25-4.18 (1H, m), 3.14-2.97 (2H, m), 2.83 (2H, s), 2.43-1.74 (14H, m), 1.69-1.52 (6H, m), 1.45-1.21 (2H, m), 1.37 (9H, s). | 418 (M + H)$^+$ |
| 3 | Chemistry | δ: 8.36 (1H, br s), 7.48 (1H, br s), 7.03-6.92 (2H, m), 6.36 (1H, ddd, J = 10.5, 2.2, 2.2 Hz), 3.76 (3H, s), 3.13-3.06 (2H, m), 2.87 (2H, s), 2.39-2.10 (3H, m), 1.94-1.82 (2H, m), 1.71-1.57 (4H, m), 1.44-1.29 (2H, m), 1.37 (9H, s). | 406 (M + H)$^+$ |

Example 4

N-(Adamantan-1-yl)-2-[(exo)-8-(tert-butylcarbamoyl)methyl-8-azabicyclo[3.2.1]octan-3-yl]acetamide

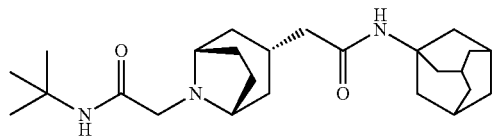 [SMILES: CC(C)(C)NC(=O)CN1[C@@H]2CC[C@H]1C[C@H](CC(=O)NC13CC4CC(CC(C4)C1)C3)C2]

The compound of Reference Example 7 (100 mg) was dissolved in dioxane (2 mL), and 2-chloro-N-tert-butylacetamide (53 mg) and DBU (220 μL) were added thereto. The mixture was stirred for 4 hours under heating at 60° C. The reaction solvent was distilled off under reduced pressure, and a residue thus obtained was purified by silica gel column chromatography (0% to 8% methanol/chloroform), to yield the title compound (86 mg).

$^1$H-NMR (CDCl$_3$)δ:7.44 (1H, brs), 5.06 (1H, brs), 3.14-3.03 (2H, m), 2.84 (2H, s), 2.23-1.79 (14H, m), 1.71-1.55 (10H, m), 1.39-1.23 (2H, m), 1.37 (9H, s).

ESI+APCI-MS Found:m/z 416 (M+H)$^+$

Example Compounds 5 to 10 produced by a method similar to that of Example 4 using corresponding raw materials are shown in Table 2 and Table 3.

TABLE 2

| Ex. | Structural formula | $^1$H-NMR (CDCl$_3$) | ESI + APCI MS |
|---|---|---|---|
| 5 | | δ: 7.43 (1H, br s), 5.19 (1H, d, J = 7.9 Hz), 4.15-4.02 (1H, m), 3.14-3.06 (2H, m), 2.85 (2H, s), 2.22-2.04 (1H, m), 1.98 (2H, d, J = 7.1 Hz), 1.94-1.83 (2H, m), 1.80-1.56 (6H, m), 1.40-1.20 (3H, m), 1.37 (9H, s), 1.09-0.98 (1H, m), 1.07 (6H, s), 0.95-0.79 (2H, m), 0.91 (6H, s). | 420 (M + H)$^+$ |
| 6 | | δ: 7.44 (1H, br s), 5.55 (1H, br s), 3.15-3.03 (2H, m), 2.85 (2H, s), 2.44-2.35 (1H, m), 2.30-2.22 (2H, m), 2.21-2.09 (1H, m), 2.08-1.95 (6H, m), 1.94-1.79 (4H, m), 1.75-1.42 (8H, m), 1.40-1.20 (2H, m), 1.36 (9H, s). | 402 (M + H)$^+$ |
| 7 | | δ: 7.77 (1H, br s), 5.57 (1H, br s), 3.60 (2H, s), 3.14-3.07 (2H, m), 2.91 (2H, s), 2.44-2.35 (1H, m), 2.30-2.23 (2H, m), 2.22-2.08 (1H, m), 2.08-1.96 (6H, m), 1.94-1.82 (4H, m), 1.72-1.49 (8H, m), 1.40-1.23 (8H, m). | 418 (M + H)$^+$ |

TABLE 3

| Ex. | Structural formula | $^1$H-NMR (CDCl$_3$) | ESI + APCI MS |
|---|---|---|---|
| 8 | | δ: 7.88 (1H, br s), 5.57 (1H, br s), 5.32 (1H, br s), 3.67 (2H, s), 3.19-3.03 (2H, m), 2.93 (2H, s), 2.46-2.32 (1H, m), 2.31-2.08 (3H, m), 2.08-1.45 (26H, m), 1.41-1.26 (2H, m). | 444 (M + H)$^+$ |
| 9 | | δ: 7.71 (1H, br s), 5.56 (1H, br s), 3.42-3.38 (5H, m), 3.16-3.06 (2H, m), 2.87 (2H, s), 2.46-2.34 (1H, m), 2.34-1.94 (9H, m), 1.93-1.47 (12H, m), 1.45-1.27 (2H, m), 1.36 (6H, s). | 432 (M + H)$^+$ |

TABLE 3-continued

| Ex. | Structural formula | ¹H-NMR (CDCl₃) | ESI + APCI MS |
|---|---|---|---|
| 10 | (structure) | δ: 7.77 (1H, br s), 5.34 (1H, br s), 5.15 (1H, br s), 3.60 (2H, s), 3.13-3.07 (2H, m), 2.90 (2H, s), 2.21-1.81 (14H, m), 1.73-1.55 (10H, m), 1.39-1.23 (2H, m), 1.30 (6H, s). | 432 (M + H)⁺ |

Example 11

N-[(exo)-8-(tert-Butylcarbamoyl)methyl-8-azabicyclo[3.2.1]octan-3-yl]methylbenzofuran-3-carboxamide

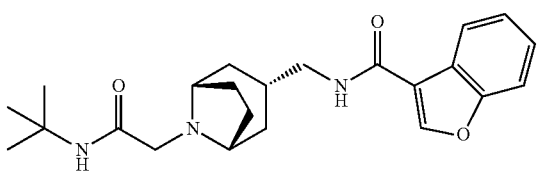 [SMILES: CC(C)(C)NC(=O)CN1[C@@H]2CC[C@H]1C[C@H](CNC(=O)c1coc3ccccc13)C2]

The compound of Reference Example 9 (85 mg) was suspended in dichloromethane (1 mL), and 1-benzofuran-3-carboxylic acid (47 mg) and HATU (109 mg) were added thereto. Subsequently, triethylamine (131 μL) was added to the mixture, and the mixture was stirred for 18.5 hours at room temperature. Water was added to the reaction solution, and extracted with chloroform. The organic layer was dried over anhydrous sodium sulfate, and the solvent was distilled off under reduced pressure. A residue thus obtained was purified by silica gel column chromatography (NH silica gel, 25% to 65% ethyl acetate/hexane), and thus the title compound (57 mg) was obtained.

¹H-NMR (CDCl₃)δ:8.11 (1H, s), 7.90-7.83 (1H, m), 7.58-7.52 (1H, m), 7.45-7.32 (3H, m), 6.04-5.94 (1H, m), 3.37 (2H, dd, J=6.5, 6.5 Hz), 3.20-3.12 (2H, m), 2.86 (2H, s), 2.06-1.85 (3H, m), 1.73-1.53 (4H, m), 1.51-1.37 (2H, m), 1.36 (9H, s).

ESI+APCI-MS Found:m/z 398 (M+H)⁺

Example Compounds 12 to 99 produced by a method similar to that of Example 11 using corresponding raw materials are shown in Table 4 to Table 31.

TABLE 4

| Ex. | Structural formula | ¹H -NMR | ESI + APCI MS |
|---|---|---|---|
| 12 | (structure) | δ: 8.22 (1H, dd, J = 8.0, 8.0 Hz), 7.69 (1H, s), 7.59 (1H, dd, J = 8.0, 1.5 Hz), 7.46 (1H, dd, J = 11.2, 1.5 Hz), 6.78-6.62 (1H, m), 5.28-5.12 (1H, m), 3.65-3.54 (2H, m), 3.38 (2H, dd, J = 6.0, 6.0 Hz), 3.23-3.10 (2H, m), 2.91 (2H, s), 2.05-1.82 (3H, m), 1.72-1.50 (4H, m), 1.47-1.34 (2H, m), 1.30 (6H, s). | 417 (M + H)⁺ |
| 13 | (structure) | δ: 7.37-7.33 (1H, m), 7.17-7.10 (1H, m), 6.95-6.88 (1H, m), 6.86-6.81 (1H, M), 6.23 (1H, s), 5.99-5.89 (1H, m), 4.09 (3H, s), 3.89 (3H, s), 3.31-3.08 (5H, m), 2.64 (1H, dd, J = 12.7, 8.0 Hz), 2.32-2.19 (2H, m), 2.24 (3H, s), 1.98-1.74 (4H, m), 1.56-1.36 (6H, m), 1.04 (3H, d, J = 6.6 Hz). | 457 (M + H)⁺ |

TABLE 5

| Ex. | Structural formula | $^1$H-NMR | ESI + APCI MS |
|---|---|---|---|
| 14 | | δ: 7.35 (1H, dd, J = 7.7, 1.7 Hz), 7.14 (1H, ddd, J = 8.0, 7.7, 1.7 Hz), 6.92 (1H, ddd, J = 7.7, 7.7, 1.1 Hz), 6.84 (1H, dd, J = 8.0, 1.1 Hz), 5.66-5.54 (1H, m), 3.90 (3H, s), 3.28 (1H, dd, J = 12.6, 4.5 Hz), 3.18-3.00 (4H, m), 2.61 (1H, dd, J = 12.6, 8.2 Hz), 2.33-2.17 (2H, m), 2.07-1.98 (3H, m), 1.93-1.64 (16H, m), 1.56-1.30 (6H, m), 1.03 (3H, d, J = 6.6 Hz). | 497 (M + H)$^+$ |
| 15 | | δ: 7.43-7.21 (6H, m), 5.24-5.04 (1H, m), 3.08-2.93 (4H, m), 2.79 (2H, s), 2.52-2.37 (2H, m), 2.08-1.08 (15H, m), 1.35 (9H, s). | 426 (M + H)$^+$ |
| 16 | | δ: 7.42 (1H, br s), 7.41 (1H, s), 6.02-5.82 (1H, m), 3.30-3.20 (2H, m), 3.18-3.08 (2H, m), 2.87-2.70 (8H, m), 2.00-1.52 (9H, m), 1.44-1.24 (2H, m), 1.36 (9H, s). | 418 (M + H)$^+$ |

TABLE 6

| Ex. | Structural formula | $^1$H-NMR | ESI + APCI MS |
|---|---|---|---|
| 17 | | δ: 7.39 (1H, br s), 6.45-6.35 (1H, m), 6.33 (1H, s), 5.52-5.45 (1H, m), 4.88-4.77 (1H, m), 3.13-3.02 (4H, m), 2.91-2.84 (1H, m), 2.81 (2H, s), 2.43-2.33 (1H, m), 2.29 (6H, s), 1.96-1.80 (2H, m), 1.78-1.17 (12H, m), 1.36 (9H, s). | 471 (M + H)$^+$ |
| 18 | | δ: 7.42 (1H, br s), 5.52-5.27 (1H, m), 3.17-3.05 (4H, m), 2.84 (2H, s), 2.02-1.50 (24H, m), 1.42-1.11 (2H, m), 1.37 (9H, s). | 430 (M + H)$^+$ |
| 19 | | δ: 7.42 (1H, br s), 5.75-5.43 (1H, m), 3.25 (2H, dd, J = 6.3, 6.3 Hz), 3.17-3.08 (2H, m), 2.84 (2H, s), 2.60-2.43 (4H, m), 2.52 (3H, s), 1.98-1.51 (11H, m), 1.44-1.28 (2H, m), 1.36 (9H, s). | 416 (M + H)$^+$ |

TABLE 6-continued

| Ex. | Structural formula | ¹H-NMR | ESI + APCI MS |
|---|---|---|---|
| 20 | | δ: 7.45 (1H, br s), 6.30 (1H, s), 6.30-6.20 (1H, m), 4.11 (3H, s), 3.26 (2H, dd, J = 6.4, 6.4 Hz), 3.20-3.08 (2H, m), 3.02-2.89 (1H, m), 2.85 (2H, s), 2.02-1.80 (3H, m), 1.68-1.53 (4H, m), 1.47-1.28 (2H, m), 1.37 (9H, s), 1.25 (6H, d, J = 7.0 Hz). | 404 (M + H)⁺ |

TABLE 7

| Ex. | Structural formula | ¹H-NMR | ESI + APCI MS |
|---|---|---|---|
| 21 | | δ: 7.40 (1H, br s), 6.80-6.71 (1H, m), 6.71 (1H, s), 6.52 (2H, s), 3.20-3.05 (4H, m), 2.82 (2H, s), 2.27 (6H, s), 1.94-1.70 (3H, m), 1.58-1.24 (4H, m), 1.50 (6H, s), 1.37-1.25 (2H, m), 1.36 (9H, s). | 444 (M + H)⁺ |
| 22 | | δ: 7.37 (1H, br s), 7.32-7.13 (4H, m), 5.29-5.10 (1H, m), 3.07-2.92 (4H, m), 2.79 (2H, s), 2.34 (3H, s), 2.28-2.13 (2H, m), 2.05-1.75 (4H, m), 1.71-1.08 (13H, m), 1.35 (9H, s). | 454 (M + H)⁺ |
| 23 | | δ: 7.41 (1H, br s), 6.26 (1H, s), 6.17-6.03 (1H, m), 4.09 (3H, s), 3.25 (2H, dd, J = 6.4, 6.4 Hz), 3.19-3.09 (2H, m), 2.84 (2H, s), 2.25 (3H, s), 1.98-1.75 (4H, m), 1.67-1.53 (3H, m), 1.44-1.25 (2H, m), 1.37 (9H, s). | 376 (M + H)⁺ |
| 24 | | δ: 7.96-7.80 (1H, m), 7.67 (1H, s), 7.52-7.23 (4H, m), 6.14-5.92 (1H, m), 3.82 (3H, s), 3.42-3.30 (2H, m), 3.28-3.03 (2H, m), 2.85 (2H, s), 2.07-1.03 (9H, m), 1.35 (9H, s). | 411 (M + H)⁺ |

TABLE 8

| Ex. | Structural formula | ¹H-NMR | ESI + APCI MS |
|---|---|---|---|
| 25 | | δ: 9.26 (1H, s), 8.60 (1H, s), 8.15 (1H, d, J = 8.4 Hz), 7.91 (1H, d, J = 7.9 Hz), 7.81 (1H, dd, J = 8.4, 7.4 Hz), 7.62 (1H, dd, J = 7.9, 7.4 Hz), 7.43 (1H, br s), 6.72-6.51 (1H, m), 3.48-3.32 (2H, m), 3.23-3.08 (2H, m), 2.84 (2H, s), 2.11-1.13 (9H, m), 1.36 (9H, s). | 409 (M + H)⁺ |

TABLE 8-continued

| Ex. | Structural formula | ¹H-NMR | ESI + APCI MS |
|---|---|---|---|
| 26 | | δ: 9.00 (1H, d, J = 4.2 Hz), 8.31 (1H, s), 8.25 (1H, d, J = 8.1 Hz), 8.16 (1H, d, J = 8.6 Hz), 8.03 (1H, d, J = 8.6 Hz), 7.48 (1H, dd, J = 8.1, 4.2 Hz), 7.42 (1H, br s), 6.44-6.28 (1H, m), 3.40 (2H, dd, J = 6.3, 6.3 Hz), 3.23-3.10 (2H, m), 2.86 (2H, s), 2.10-1.82 (3H, m), 1.73-1.30 (6H, m), 1.36 (9H, s). | 409 (M + H)⁺ |
| 27 | | δ: 7.39 (1H, br s), 7.19-7.11 (2H, m), 6.93-6.85 (2H, m), 6.75-6.66 (1H, m), 3.16 (2H, dd, J = 6.5, 6.5 Hz), 3.12-3.05 (2H, m), 2.85 (1H, dd, J = 10.2, 8.0 Hz), 2.82 (2H, s), 2.00-1.72 (5H, m), 1.66-1.25 (6H, m), 1.52 (6H, s), 1.35 (9H, s). | 524 (M + H)⁺ |

TABLE 9

| Ex. | Structural formula | ¹H-NMR | ESI + APCI MS |
|---|---|---|---|
| 28 | | δ: 7.40 (1H, br s), 7.31-7.24 (2H, m), 7.10-7.04 (1H, m), 6.94-6.87 (2H, m), 6.82-6.71 (1H, m), 3.17 (2H, dd, J = 6.5, 6.5 Hz), 3.13-3.05 (2H, m), 2.82 (2H, s), 1.97-1.72 (4H, m), 1.58-1.47 (3H, m), 1.51 (6H, s), 1.38-1.26 (2H, m), 1.36 (9H, s). | 416 (M + H)⁺ |
| 29 | | δ: 7.39 (1H, br s), 6.00 (1H, s), 5.71-5.62 (1H, m), 3.12-2.98 (4H, m), 2.81 (2H, s), 2.31 (3H, s), 2.20-2.03 (4H, m), 1.92-1.19 (15H, m), 1.36 (9H, s). | 445 (M + H)⁺ |
| 30 | | δ: 7.40 (1H, br s), 7.02-6.84 (4H, m), 6.84-6.75 (1H, m), 3.18 (2H, dd, J = 6.5, 6.5 Hz), 3.15-3.08 (2H, m), 2.83 (2H, s), 1.94-1.77 (3H, m), 1.59-1.49 (4H, m), 1.47 (6H, s), 1.39-1.29 (2H, m), 1.36 (9H, s). | 434 (M + H)⁺ |

TABLE 10

| Ex. | Structural formula | ¹H-NMR | ESI + APCI MS |
|---|---|---|---|
| 31 | | δ: 7.39 (1H, br s), 7.20 (1H, dd, J = 8.2, 8.2 Hz), 7.06 (1H, ddd, J = 8.2, 2.0, 1.0 Hz), 6.92 (1H, dd, J = 2.2, 2.0 Hz), 6.80 (1H, ddd, J = 8.2, 2.2, 1.0 Hz), 6.68-6.59 (1H, m), 3.17 (2H, dd, J = 6.5, 6.5 Hz), 3.13-3.06 (2H, m), 2.82 (2H, s), 1.94-1.74 (3H, m), 1.60-1.46 (4H, m), 1.59 (3H, s), 1.53 (3H, s), 1.37-1.26 (2H, m), 1.36 (9H, s). | 450 (M + H)⁺ |

TABLE 10-continued

| Ex. | Structural formula | ¹H-NMR | ESI + APCI MS |
|---|---|---|---|
| 32 | | δ: 7.40 (1H, br s), 7.20-7.13 (1H, m), 6.75-6.66 (1H, m), 6.65-6.59 (1H, m), 6.52-6.45 (2H, m), 3.78 (3H, s), 3.16 (2H, dd, J = 6.5, 6.5 Hz), 3.13-3.04 (2H, m), 2.82 (2H, s), 1.92-1.73 (3H, m), 1.57-1.45 (4H, m), 1.57 (3H, s), 1.52 (3H, s), 1.37-1.25 (2H, m), 1.36 (9H, s). | 446 (M + H)⁺ |
| 33 | | δ: 8.48 (1H, dd, J = 6.9, 2.1 Hz), 8.00 (1H, s), 7.87-7.80 (1H, m), 7.48-7.34 (3H, m), 6.16-6.02 (1H, m), 3.39 (2H, dd, J = 6.4, 6.4 Hz), 3.20-3.13 (2H, m), 2.86 (2H, s), 2.70 (3H, s), 2.06-1.85 (3H, m), 1.72-1.55 (4H, m), 1.50-1.39 (2H, m), 1.36 (9H, s). | 439 (M + H)⁺ |

TABLE 11

| Ex. | Structural formula | ¹H-NMR | ESI + APCI MS |
|---|---|---|---|
| 34 | | δ: 7.50-6.56 (4H, m), 6.00-5.80 (1H, m), 3.87 (3H, s), 3.66 (3H, s), 3.42-3.08 (4H, m), 2.85 (2H, s), 2.70 (3H, s), 2.05-1.12 (9H, m), 1.35 (9H, s). | 455 (M + H)⁺ |
| 35 | | δ: 8.86 (1H, br s), 7.96 (1H, d, J = 1.9 Hz), 7.75-7.73 (1H, m), 7.47-7.41 (1H, m), 7.35 (1H, d, J = 8.7 Hz), 7.23 (1H, dd, J = 8.7, 1.9 Hz), 5.99-5.84 (1H, m), 3.36 (2H, dd, J = 6.4, 6.4 Hz), 3.18-3.12 (2H, m), 2.86 (2H, s), 2.04-1.85 (3H, m), 1.70-1.57 (4H, m), 1.48-1.37 (2H, m), 1.36 (9H, s). | 431 (M + H)⁺ |
| 36 | | δ: 7.93-7.77 (1H, m), 7.75 (1H, s), 7.48-7.22 (4H, m), 6.10-5.90 (1H, m), 4.20 (2H, q, J = 6.5 Hz), 3.42-3.30 (2H, m), 3.20-3.07 (2H, m), 2.85 (2H, s), 2.07-1.10 (12H, m), 1.35 (9H, s). | 425 (M + H)⁺ |

TABLE 12

| Ex. | Structural formula | ¹H-NMR | ESI + APCI MS |
|---|---|---|---|
| 37 | | δ: 7.68-7.62 (1H, m), 7.45 (1H, br s), 7.37-7.31 (1H, m), 7.25-7.18 (2H, m), 6.10-5.91 (1H, m), 3.70 (3H, s), 3.38 (2H, dd, J = 6.3, 6.3 Hz), 3.20-3.12 (2H, m), 2.85 (2H, s), 2.74 (3H, s), 2.07-1.85 (3H, m), 1.75-1.38 (6H, m), 1.35 (9H, s). | 425 (M + H)⁺ |
| 38 | | δ: 6.26 (1H, s), 6.06-5.96 (1H, m), 4.10 (3H, s), 3.29-3.22 (4H, m), 3.13 (2H, s), 3.02-2.88 (1H, m), 3.00 (3H, s), 2.05-1.83 (3H, m), 1.62-1.44 (6H, m), 1.41 (9H, s), 1.25 (6H, d, J = 7.0 Hz). | 418 (M + H)⁺ |
| 39 | | δ: 7.30-7.24 (2H, m), 7.08-7.03 (1H, m), 6.93-6.88 (2H, m), 6.78-6.69 (1H, m), 3.24-3.18 (2H, m), 3.15 (2H, dd, J = 6.6, 6.6 Hz), 3.10 (2H, s), 3.00 (3H, s), 2.00-1.72 (3H, m), 1.58-1.35 (6H, m), 1.51 (6H, s), 1.40 (9H, s). | 430 (M + H)⁺ |

TABLE 13

| Ex. | Structural formula | ¹H-NMR | ESI + APCI MS |
|---|---|---|---|
| 40 | | δ: 7.28-7.15 (1H, m), 7.23 (1H, d, J = 2.2 Hz), 7.19 (1H, d, J = 8.8 Hz), 6.85 (1H, dd, J = 8.8, 2.2 Hz), 5.92-5.82 (1H, m), 3.65 (3H, s), 3.46-3.40 (2H, m), 3.31-3.21 (4H, m), 2.69 (3H, s), 2.16-1.90 (3H, m), 1.80-1.23 (6H, m), 1.37 (9H, s). | 441 (M + H)⁺ |
| 41 | | δ: 8.48 (1H, br s), 7.75-7.72 (1H, m), 7.70 (1H, s), 7.45 (1H, br s), 7.33 (1H, d, J = 8.4 Hz), 7.10 (1H, dd, J = 8.4, 1.4 Hz), 6.03-5.92 (1H, m), 3.38 (2H, dd, J = 6.4, 6.4 Hz), 3.20-3.10 (2H, m), 2.86 (2H, s), 2.50 (3H, s), 2.04-1.81 (3H, m), 1.73-1.38 (6H, m), 1.35 (9H, s). | 411 (M + H)⁺ |
| 42 | | δ: 8.50 (1H, br s), 7.79-7.75 (1H, m), 7.67-7.60 (1H, m), 7.44 (1H, br s), 7.36 (1H, dd, J = 8.9, 4.5 Hz), 7.08-6.99 (1H, m), 5.94-5.81 (1H, m), 3.37 (2H, dd, J = 6.4, 6.4 Hz), 3.19-3.11 (2H, m), 2.86 (2H, s), 2.04-1.86 (3H, m), 1.73-1.38 (6H, m), 1.36 (9H, s). | 415 (M + H)⁺ |

TABLE 14
| Ex. | Structural formula | ¹H-NMR | ESI + APCI MS |
|---|---|---|---|
| 43 | 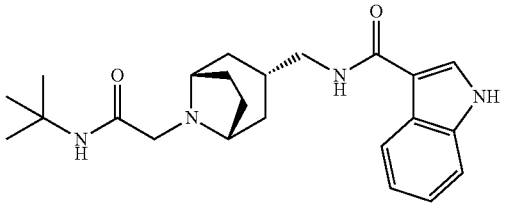 [SMILES: CC(C)(C)NC(=O)CN1[C@@H]2CC[C@H]1C[C@H](CNC(=O)c1c[nH]c3ccccc13)C2] | δ: 8.66 (1H, br s), 7.94-7.86 (1H, m), 7.83-7.78 (1H, m), 7.51-7.39 (2H, m), 7.32-7.25 (2H, m), 6.07-5.97 (1H, m), 3.39 (2H, dd, J = 6.4, 6.4 Hz), 3.20-3.10 (2H, m), 2.86 (2H, s), 2.05-1.81 (3H, m), 1.73-1.38 (6H, m), 1.36 (9H, s). | 397 (M + H)⁺ |
| 44 | 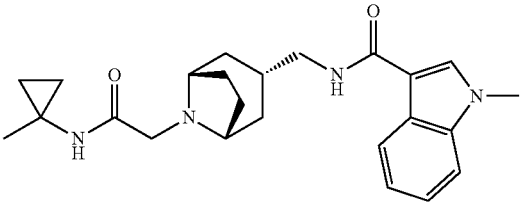 | δ: 7.90-7.84 (1H, m), 7.70 (1H, br s), 7.67 (1H, s), 7.42-7.24 (3H, m), 6.06-5.85 (1H, m), 3.83 (3H, s), 3.38 (2H, dd, J = 6.5, 6.5 Hz), 3.16-3.04 (2H, m), 2.89 (2H, s), 2.06-1.79 (3H, m), 1.71-1.36 (6H, m), 1.39 (3H, s), 0.78-0.61 (4H, m). | 409 (M + H)⁺ |
| 45 | 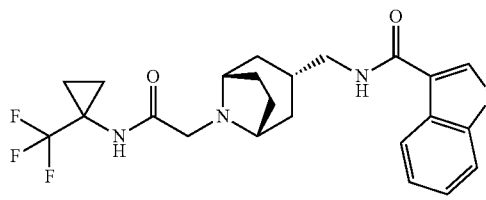 | δ: 8.07 (1H, br s), 7.92-7.84 (1H, m), 7.67 (1H, s), 7.41-7.22 (3H, m), 6.08-5.88 (1H, m), 3.83 (3H, s), 3.38 (2H, dd, J = 6.4, 6.4 Hz), 3.19-3.06 (2H, m), 2.95 (2H, s), 2.07-1.05 (13H, m). | 463 (M + H)⁺ |
TABLE 15
| Ex. | Structural formula | ¹H-NMR | ESI + APCI MS |
|---|---|---|---|
| 46 | 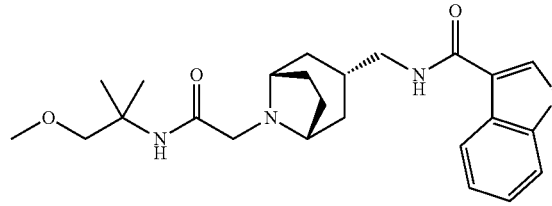 | δ: 7.90-7.83 (1H, m), 7.74 (1H, br s), 7.67 (1H, s), 7.41-7.22 (3H, m), 6.02-5.87 (1H, m), 3.83 (3H, s), 3.40-3.32 (4H, m), 3.37 (3H, s), 3.20-3.11 (2H, m), 2.87 (2H, s), 2.06-1.81 (3H, m), 1.72-1.37 (6H, m), 1.35 (6H, s). | 441 (M + H)⁺ |
| 47 | 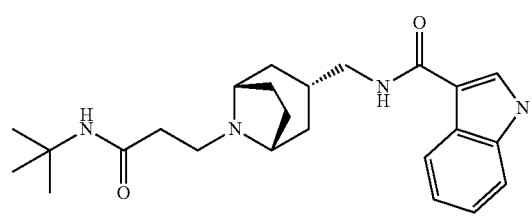 | δ: 8.77 (1H, br s), 7.91-7.84 (1H, m), 7.67 (1H, s), 7.41-7.24 (3H, m), 6.09-5.94 (1H, m), 3.83 (3H, s), 3.38-3.27 (4H, m), 2.57 (2H, t, J = 5.9 Hz), 2.22 (2H, t, J = 5.9 Hz), 2.13-1.26 (9H, m), 1.32 (9H, s). | 425 (M + H)⁺ |
| 48 | 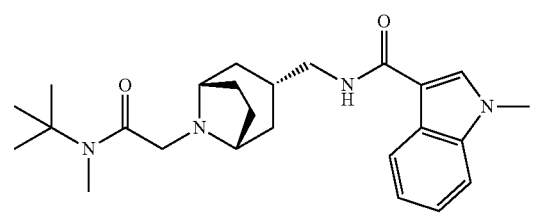 [SMILES: CN(C(=O)CN1[C@@H]2CC[C@H]1C[C@H](CNC(=O)c1cn(C)c3ccccc13)C2)C(C)(C)C] | ¹H-NMR (CD₃OD) δ: 8.12-8.04 (1H, m), 7.78 (1H, s), 7.45-7.38 (1H, m), 7.28-7.13 (2H, m), 3.84 (3H, s), 3.31-3.26 (2H, m), 3.25-3.17 (4H, m), 3.01 (3H, s), 2.13-1.89 (3H, m), 1.69-1.44 (6H, m), 1.41 (9H, s). | 425 (M + H)⁺ |

TABLE 16

| Ex. | Structural formula | ¹H-NMR | ESI + APCI MS |
|---|---|---|---|
| 49 | 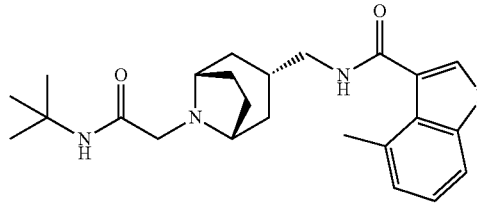 | δ: 7.42 (1H, br s), 7.34 (1H, s), 7.23-7.14 (2H, m), 7.01-6.96 (1H, m), 5.88-5.75 (1H, m), 3.78 (3H, s), 3.32 (2H, dd, J = 6.5, 6.5 Hz), 3.18-3.11 (2H, m), 2.85 (2H, s), 2.68 (3H, s), 2.05-1.81 (3H, m), 1.70-1.49 (4H, m), 1.47-1.32 (2H, m), 1.37 (9H, s). | 425 (M + H)⁺ |
| 50 | 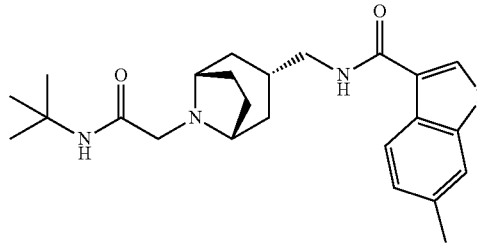 | δ: 7.72 (1H, d, J = 8.1 Hz), 7.60 (1H, s), 7.44 (1H, br s), 7.16 (1H, s), 7.13-7.08 (1H, m), 6.00-5.87 (1H, m), 3.79 (3H, s), 3.37 (2H, dd, J = 6.4, 6.4 Hz), 3.18-3.10 (2H, m), 2.85 (2H, s), 2.51 (3H, s), 2.04-1.81 (3H, m), 1.72-1.54 (4H, m), 1.49-1.37 (2H, m), 1.35 (9H, s). | 425 (M + H)⁺ |
| 51 | 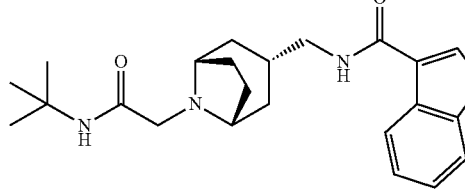 | δ: 7.71 (1H, d, J = 7.8 Hz), 7.54 (1H, s), 7.44 (1H, br s), 7.11 (1H, dd, J = 7.8, 7.8 Hz), 6.98 (1H, d, J = 7.8 Hz), 5.97-5.88 (1H, m), 4.09 (3H, s), 3.36 (2H, dd, J = 6.4, 6.4 Hz), 3.18-3.11 (2H, m), 2.85 (2H, s), 2.78 (3H, s), 2.04-1.81 (3H, m), 1.72-1.50 (4H, m), 1.49-1.37 (2H, m), 1.36 (9H, s). | 425 (M + H)⁺ |

TABLE 17

| Ex. | Structural formula | ¹H-NMR | ESI + APCI MS |
|---|---|---|---|
| 52 | 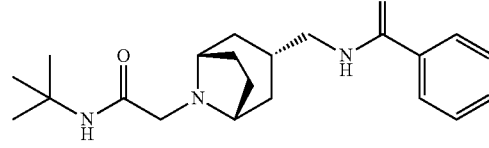 | δ: 7.75-7.72 (1H, m), 7.66-7.60 (1H, m), 7.51-7.34 (3H, m), 6.21-6.12 (1H, m), 3.33 (2H, dd, J = 6.4, 6.4 Hz), 3.18-3.12 (2H, m), 2.85 (2H, s), 2.04-1.86 (3H, m), 1.68-1.56 (4H, m), 1.46-1.30 (2H, m), 1.36 (9H, s). | 392 (M + H)⁺ |
| 53 | 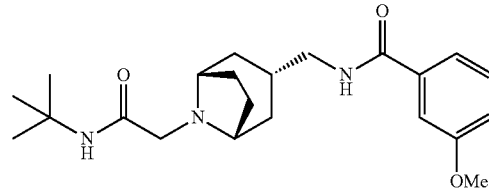 | δ: 7.43 (1H, br s), 7.26-7.21 (2H, m), 7.03-6.99 (1H, m), 6.42-6.31 (1H, m), 3.84 (3H, s), 3.30 (2H, dd, J = 6.4, 6.4 Hz), 3.17-3.10 (2H, m), 2.83 (2H, s), 2.01-1.75 (3H, m), 1.69-1.53 (4H, m), 1.46-1.33 (2H, m), 1.36 (9H, s). | 422 (M + H)⁺ |
| 54 | 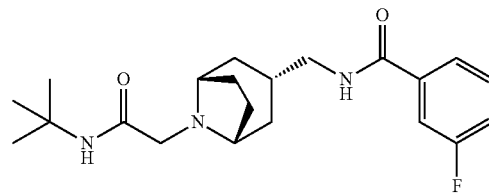 | δ: 7.53-7.50 (1H, m), 7.46-7.36 (2H, m), 7.26-7.19 (1H, m), 6.40-6.30 (1H, m), 3.32 (2H, dd, J = 6.4, 6.4 Hz), 3.18-3.11 (2H, m), 2.84 (2H, s), 2.04-1.82 (3H, m), 1.69-1.53 (4H, m), 1.46-1.33 (2H, m), 1.36 (9H, s). | 410 (M + H)⁺ |

TABLE 18

| Ex. | Structural formula | ¹H-NMR | ESI + APCI MS |
|---|---|---|---|
| 55 | (structure) | δ: 7.43 (1H, br s), 7.35-7.30 (1H, m), 7.28-7.21 (1H, m), 7.05-6.98 (1H, m), 6.27-6.17 (1H, m), 3.32 (2H, dd, J = 6.4, 6.4 Hz), 3.17-3.11 (2H, m), 2.84 (2H, s), 2.40 (3H, s), 2.01-1.82 (3H, m), 1.67-1.55 (4H, m), 1.44-1.32 (2H, m), 1.36 (9H, s). | 390 (M + H)⁺ |
| 56 | (structure) | δ: 7.43 (1H, br s), 7.14-7.11 (1H, m), 7.03-6.97 (1H, m), 6.74 (1H, ddd, J = 10.2, 2.3, 2.3 Hz), 6.33-6.23 (1H, m), 3.84 (3H, s), 3.31 (2H, dd, J = 6.4, 6.4 Hz), 3.17-3.11 (2H, m), 2.84 (2H, s), 2.04-1.87 (3H, m), 1.68-1.53 (4H, m), 1.45-1.34 (2H, m), 1.36 (9H, s). | 406 (M + H)⁺ |
| 57 | (structure) | δ: 8.07-7.90 (2H, m), 7.47 (1H, br s), 7.18-7.12 (1H, m), 6.94 (1H, dd, J = 7.6, 7.6 Hz), 4.38-4.31 (2H, m), 3.32 (2H, dd, J = 6.3, 6.3 Hz), 3.20-3.07 (2H, m), 2.90-2.83 (4H, m), 2.19-1.80 (6H, m), 1.72-1.52 (3H, m), 1.47-1.29 (2H, m), 1.36 (9H, s). | 414 (M + H)⁺ |

TABLE 19

| Ex. | Structural formula | ¹H-NMR | ESI + APCI MS |
|---|---|---|---|
| 58 | (structure) | δ: 7.72 (1H, dd, J = 7.7, 1.8 Hz), 7.65-7.58 (1H, m), 7.45 (1H, br s), 7.01-6.91 (2H, m), 4.46-4.41 (2H, m), 4.35-4.30 (2H, m), 3.32 (2H, dd, J = 6.3, 6.3 Hz), 3.20-3.11 (2H, m), 2.87 (2H, s), 2.04-1.89 (4H, m), 1.69-1.54 (3H, m), 1.48-1.32 (2H, m), 1.36 (9H, s). | 416 (M + H)⁺ |
| 59 | (structure) | δ: 7.56-7.38 (3H, m), 6.79 (1H, d, J = 8.4 Hz), 6.22-6.10 (1H, m), 4.26-4.17 (2H, m), 3.30 (2H, dd, J = 6.4, 6.4 Hz), 3.19-3.06 (2H, m), 2.89-2.76 (2H, m), 2.84 (2H, s), 2.07-1.78 (6H, m), 1.69-1.52 (3H, m), 1.46-1.30 (2H, m), 1.36 (9H, s). | 414 (M + H)⁺ |
| 60 | (structure) | δ: 7.64-7.58 (1H, m), 7.55-7.48 (1H, m), 7.44 (1H, br s), 7.30-7.22 (1H, m), 6.19-6.00 (1H, m), 3.32 (2H, dd, J = 6.4, 6.4 Hz), 3.20-3.09 (2H, m), 2.94 (4H, dd, J = 7.5, 7.5 Hz), 2.89-2.81 (2H, m), 2.16-2.06 (2H, m), 2.00-1.83 (3H, m), 1.71-1.52 (4H, m), 1.49-1.32 (2H, m), 1.36 (9H, s). | 398 (M + H)⁺ |

TABLE 20

| Ex. | Structural formula | ¹H-NMR | ESI + APCI MS |
|---|---|---|---|
| 61 | | δ: 9.04 (1H, d, J = 1.9 Hz), 8.30 (1H, dd, J = 8.1, 1.9 Hz), 7.78 (1H, d, J = 8.1 Hz), 7.39 (1H, br s), 6.48-6.33 (1H, m), 3.37 (2H, dd, J = 6.4, 6.4 Hz), 3.21-3.10 (2H, m), 2.85 (2H, s), 2.06-1.85 (3H, m), 1.69-1.53 (4H, m), 1.48-1.32 (2H, m), 1.36 (9H, s). | 427 (M + H)⁺ |
| 62 | | δ: 8.81 (1H, d, J = 2.1 Hz), 8.69 (1H, d, J = 2.2 Hz), 8.10 (1H, dd, J = 2.2, 2.1 Hz), 7.39 (1H, br s), 6.33-6.22 (1H, m), 3.35 (2H, dd, J = 6.5, 6.5 Hz), 3.19-3.12 (2H, m), 2.85 (2H, s), 2.03-1.85 (3H, m), 1.67-1.58 (4H, m), 1.46-1.35 (2H, m), 1.37 (9H, s). | 393 (M + H)⁺ |
| 63 | | δ: 8.75-8.71 (1H, m), 8.58-8.54 (1H, m), 7.95-7.90 (1H, m), 7.40 (1H, br s), 6.20-6.10 (1H, m), 3.35 (2H, dd, J = 6.5, 6.5 Hz), 3.20-3.11 (2H, m), 2.85 (2H, s), 2.43-2.38 (3H, m), 2.05-1.85 (3H, m), 1.70-1.53 (4H, m), 1.45-1.37 (2H, m), 1.37 (9H, s). | 373 (M + H)⁺ |

TABLE 21

| Ex. | Structural formula | ¹H-NMR | ESI + APCI MS |
|---|---|---|---|
| 64 | | ¹H-NMR (CD₃OD) δ: 8.15-8.00 (1H, m), 7.20-7.06 (4H, m), 4.06-3.91 (2H, m), 3.68 (2H, s), 3.28-3.03 (7H, m), 2.30-2.08 (3H, m), 2.07-1.97 (2H, m), 1.96-1.85 (2H, m), 1.81-1.68 (2H, m), 1.36 (9H, s). | 398 (M + H)⁺ |
| 65 | | δ: 7.41 (1H, br s), 5.67-5.57 (1H, m), 3.16-3.07 (4H, m), 2.83 (2H, s), 2.09-2.00 (3H, m), 1.97-1.62 (15H, m), 1.61-1.48 (4H, m), 1.40-1.25 (2H, m), 1.37 (9H, s). | 416 (M + H)⁺ |
| 66 | | δ: 7.40 (1H, br s), 5.44-5.30 (1H, m), 3.18-3.06 (4H, m), 2.84 (2H, s), 2.04 (2H, s), 1.98-1.72 (3H, m), 1.66-1.53 (4H, m), 1.41-1.27 (2H, m), 1.37 (9H, s), 1.04 (9H, s). | 352 (M + H)⁺ |
| 67 | | δ: 7.43 (1H, br s), 5.49-5.35 (1H, m), 3.15-3.06 (4H, m), 2.84 (2H, s), 1.98-1.69 (3H, m), 1.64-1.49 (4H, m), 1.43-1.28 (2H, m), 1.37 (9H, s), 1.25 (6H, s), 1.15 (6H, s), 0.82 (1H, s). | 378 (M + H)⁺ |

TABLE 22

| Ex. | Structural formula | ¹H-NMR | ESI + APCI MS |
|---|---|---|---|
| 68 | | δ: 8.67 (1H, d, J = 2.2 Hz), 8.53 (1H, d, J = 2.2 Hz), 7.73 (1H, dd, J = 2.2, 2.2 Hz), 7.40 (1H, br s), 6.25-6.14 (1H, m), 3.34 (2H, dd, J = 6.4, 6.4 Hz), 3.19-3.10 (2H, m), 2.85 (2H, s), 2.03-1.87 (4H, m), 1.68-1.55 (4H, m), 1.46-1.33 (2H, m), 1.36 (9H, s), 1.12-1.03 (2H, m), 0.84-0.76 (2H, m). | 399 (M + H)⁺ |
| 69 | | δ: 7.41 (1H, br s), 6.28 (1H, s), 6.06-5.91 (1H, m), 4.11 (3H, s), 3.26 (2H, dd, J = 6.5, 6.5 Hz), 3.19-3.11 (2H, m), 2.85 (2H, s), 1.99-1.84 (3H, m), 1.69-1.54 (4H, m), 1.44-1.34 (2H, m), 1.37 (9H, s), 1.30 (9H, s). | 418 (M + H)⁺ |
| 70 | | δ: 8.60 (1H, d, J = 1.6 Hz), 8.50 (1H, d, J = 2.8 Hz), 7.72 (1H, dd, J = 2.8, 1.6 Hz), 7.39 (1H, br s), 6.32-6.22 (1H, m), 4.46 (2H, q, J = 7.9 Hz), 3.36 (2H, dd, J = 6.5, 6.5 Hz), 3.21-3.11 (2H, m), 2.85 (2H, s), 2.02-1.89 (3H, m), 1.68-1.55 (4H, m), 1.47-1.35 (2H, m), 1.37 (9H, s). | 457 (M + H)⁺ |

TABLE 23

| Ex. | Structural formula | ¹H-NMR | ESI + APCI MS |
|---|---|---|---|
| 71 | | δ: 7.41 (1H, br s), 5.57-5.35 (1H, m), 3.16-3.08 (4H, m), 2.84 (2H, s), 2.19-2.10 (2H, m), 2.00-1.69 (3H, m), 1.62-1.48 (6H, m), 1.37-1.27 (2H, m), 1.37 (9H, s), 0.90 (9H, s). | 366 (M + H)⁺ |
| 72 | | δ: 7.43 (1H, br s), 7.15-7.10 (1H, m), 7.11-7.06 (1H, m), 6.87-6.83 (1H, m), 6.22-6.11 (1H, m), 3.83 (3H, s), 3.31 (2H, dd, J = 6.4, 6.4 Hz), 3.19-3.09 (2H, m), 2.84 (2H, s), 2.36 (3H, s), 2.02-1.84 (3H, m), 1.75-1.58 (4H, m), 1.46-1.33 (2H, m), 1.36 (9H, s). | 402 (M + H)⁺ |
| 73 | | δ: 7.91 (1H, s), 7.70 (1H, s), 7.43 (1H, br s), 5.98-5.88 (1H, m), 4.58-4.43 (1H, m), 3.27 (2H, dd, J = 6.4, 6.4 Hz), 3.17-3.10 (2H, m), 2.84 (2H, s), 1.99-1.82 (3H, m), 1.68-1.52 (4H, m), 1.51 (6H, d, J = 6.8 Hz), 1.45-1.34 (2H, m), 1.36 (9H, s). | 390 (M + H)⁺ |

TABLE 23-continued

| Ex. | Structural formula | ¹H-NMR | ESI + APCI MS |
|---|---|---|---|
| 74 | 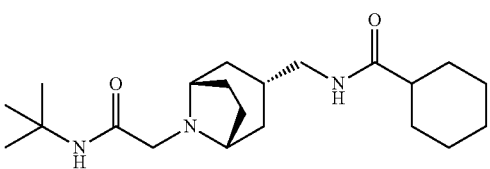 [SMILES: CC(C)(C)NC(=O)CN1[C@@H]2CC[C@H]1C[C@H](CNC(=O)C1CCCCC1)C2] | δ: 7.40 (1H, br s), 5.57-5.48 (1H, m), 3.15-3.06 (4H, m), 2.82 (2H, s), 2.14-1.94 (1H, m), 1.94-1.07 (19H, m), 1.35 (9H, s). | 364 (M + H)⁺ |

TABLE 24

| Ex. | Structural formula | ¹H-NMR | ESI + APCI MS |
|---|---|---|---|
| 75 | 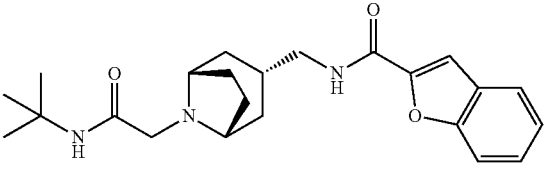 | δ: 7.68 (1H, d, J = 7.7 Hz), 7.54-7.37 (4H, m), 7.31 (1H, d, J = 7.3 Hz), 6.73-6.63 (1H, m), 3.36 (2H, dd, J = 6.4, 6.4 Hz), 3.21-3.12 (2H, m), 2.85 (2H, s), 2.08-1.87 (3H, m), 1.76-1.54 (4H, m), 1.51-1.40 (2H, m), 1.36 (9H, s). | 398 (M + H)⁺ |
| 76 | 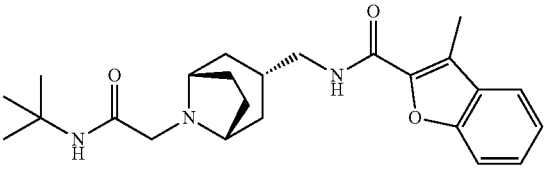 | δ: 7.64-7.59 (1H, m), 7.50-7.38 (3H, m), 7.34-7.27 (1H, m), 6.74-6.63 (1H, m), 3.34 (2H, dd, J = 6.5, 6.5 Hz), 3.20-3.11 (2H, m), 2.85 (2H, s), 2.63 (3H, s), 2.03-1.85 (3H, m), 1.73-1.55 (4H, m), 1.50-1.37 (2H, m), 1.36 (9H, s). | 412 (M + H)⁺ |
| 77 | 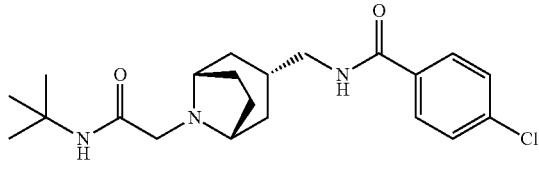 [SMILES: CC(C)(C)NC(=O)CN1[C@@H]2CC[C@H]1C[C@H](CNC(=O)c1ccc(Cl)cc1)C2] | δ: 7.73-7.65 (2H, m), 7.45-7.36 (3H, m), 6.19-6.09 (1H, m), 3.32 (2H, dd, J = 6.4, 6.4 Hz), 3.18-3.09 (2H, m), 2.85 (2H, s), 2.03-1.83 (3H, m), 1.70-1.51 (4H, m), 1.46-1.37 (2H, m), 1.36 (9H, s). | 392 (M + H)⁺ |

TABLE 25

| Ex. | Structural formula | ¹H-NMR | ESI + APCI MS |
|---|---|---|---|
| 78 | 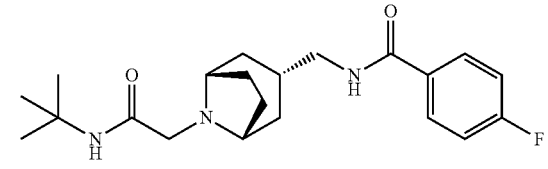 [SMILES: CC(C)(C)NC(=O)CN1[C@@H]2CC[C@H]1C[C@H](CNC(=O)c1ccc(F)cc1)C2] | δ: 7.81-7.69 (2H, m), 7.41 (1H, br s), 7.18-7.04 (2H, m), 6.17-6.04 (1H, m), 3.32 (2H, dd, J = 6.4, 6.4 Hz), 3.19-3.09 (2H, m), 2.85 (2H, s), 2.01-1.84 (3H, m), 1.70-1.51 (4H, m), 1.47-1.37 (2H, m), 1.36 (9H, s). | 376 (M + H)⁺ |
| 79 | 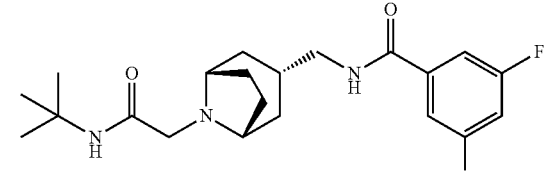 | δ: 7.83-7.78 (1H, m), 7.78-7.70 (1H, m), 7.54-7.45 (1H, m), 7.37 (1H, br s), 6.33-6.04 (1H, m), 3.34 (2H, dd, J = 6.4, 6.4 Hz), 3.21-3.12 (2H, m), 2.86 (2H, s), 2.03-1.86 (3H, m), 1.71-1.51 (4H, m), 1.47-1.39 (2H, m), 1.37 (9H, s). | 401 (M + H)⁺ |

TABLE 25-continued

| Ex. | Structural formula | ¹H-NMR | ESI + APCI MS |
|---|---|---|---|
| 80 | | δ: 7.69-7.64 (1H, m), 7.54-7.48 (1H, m), 7.42 (1H, br s), 6.78 (1H, d, J = 8.4 Hz), 6.09-5.95 (1H, m), 4.64 (2H, t, J = 8.7 Hz), 3.31 (2H, dd, J = 6.4, 6.4 Hz), 3.24 (2H, t, J = 8.7 Hz), 3.19-3.09 (2H, m), 2.84 (2H, s), 2.01-1.84 (3H, m), 1.69-1.50 (4H, m), 1.45-1.38 (2H, m), 1.36 (9H, s). | 400 (M + H)⁺ |

TABLE 26

| Ex. | Structural formula | ¹H-NMR | ESI + APCI MS |
|---|---|---|---|
| 81 | | δ: 7.42 (1H, br s), 7.32-7.27 (1H, m), 6.75-6.71 (1H, m), 5.90-5.81 (1H, m), 3.28 (2H, dd, J = 6.4, 6.4 Hz), 3.17-3.09 (2H, m), 2.84 (2H, s), 2.52-2.49 (3H, m), 1.97-1.83 (3H, m), 1.67-1.51 (4H, m), 1.44-1.37 (2H, m), 1.36 (9H, s). | 378 (M + H)⁺ |
| 82 | | δ: 7.39 (1H, br s), 5.77-5.64 (1H, m), 3.32-3.20 (3H, m), 3.19-3.10 (2H, m), 2.85 (2H, s), 2.66 (3H, s), 2.00-1.84 (3H, m), 1.67-1.51 (4H, m), 1.44-1.32 (2H, m), 1.38 (6H, d, J = 7.2 Hz), 1.36 (9H, s). | 421 (M + H)⁺ |
| 83 | | δ: 7.42 (1H, br s), 6.18-6.07 (1H, m), 3.27 (2H, dd, J = 6.5, 6.5 Hz), 3.18-3.11 (2H, m), 2.85 (2H, s), 2.48 (3H, s), 2.01-1.82 (3H, m), 1.68-1.54 (4H, m), 1.45-1.32 (2H, m), 1.40 (9H, s), 1.36 (9H, s). | 419 (M + H)⁺ |

TABLE 27

| Ex. | Structural formula | ¹H-NMR | ESI + APCI MS |
|---|---|---|---|
| 84 | | δ: 7.62-7.54 (1H, m), 7.52-7.45 (1H, m), 7.41 (1H, br s), 7.33-7.27 (2H, m), 5.99-5.89 (1H, m), 3.37 (2H, dd, J = 6.3, 6.3 Hz), 3.20-3.12 (2H, m), 3.15 (2H, q, J = 7.6 Hz), 2.86 (2H, s), 2.02-1.87 (3H, m), 1.74-1.42 (6H, m), 1.39-1.34 (3H, m), 1.36 (9H, s). | 426 (M + H)⁺ |
| 85 | | δ: 7.64-7.53 (1H, m), 7.51-7.35 (2H, m), 7.35-7.28 (2H, m), 5.98-5.92 (1H, m), 3.38 (2H, dd, J = 6.5, 6.5 Hz), 3.21-3.12 (2H, m), 2.86 (2H, s), 2.74 (3H, s), 2.06-1.85 (3H, m), 1.75-1.43 (6H, m), 1.36 (9H, s). | 412 (M + H)⁺ |

TABLE 27-continued

| Ex. | Structural formula | ¹H-NMR | ESI + APCI MS |
|---|---|---|---|
| 86 | | δ: 7.40 (1H, br s), 7.35 (1H, d, J = 9.0 Hz), 7.10 (1H, d, J = 2.6 Hz), 6.88 (1H, dd, J = 9.0, 2.6 Hz), 5.95-5.78 (1H, m), 3.87 (3H, s), 3.37 (2H, dd, J = 6.4, 6.4 Hz), 3.22-3.11 (2H, m), 2.86 (2H, s), 2.70 (3H, s), 2.08-1.85 (3H, m), 1.74-1.51 (4H, m), 1.50-1.38 (2H, m), 1.35 (9H, s). | 442 (M + H)⁺ |

TABLE 28

| Ex. | Structural formula | ¹H-NMR | ESI + APCI MS |
|---|---|---|---|
| 87 | | δ: 8.19-8.06 (1H, m), 7.42 (1H, br s), 7.05-6.96 (1H, m), 6.91-6.81 (1H, m), 6.73-6.60 (1H, m), 3.39-3.32 (2H, m), 3.19-3.11 (2H, m), 2.85 (2H, s), 2.04-1.85 (3H, m), 1.70-1.52 (4H, m), 1.48-1.38 (2H, m), 1.36 (9H, s). | 394 (M + H)⁺ |
| 88 | | δ: 7.40 (1H, br s), 5.79-5.59 (1H, m), 3.31-3.22 (2H, m), 3.19-3.09 (2H, m), 2.85 (2H, s), 2.67 (3H, s), 2.65 (3H, s), 2.00-1.80 (3H, m), 1.67-1.52 (4H, m), 1.44-1.32 (2H, m), 1.37 (9H, s). | 393 (M + H)⁺ |
| 89 | | δ: 8.12 (1H, s), 7.91-7.84 (1H, m), 7.67 (1H, br s), 7.60-7.52 (1H, m), 7.42-7.33 (2H, m), 6.09-5.91 (1H, m), 3.38 (2H, dd, J = 6.5, 6.5 Hz), 3.20-3.05 (2H, m), 2.90 (2H, s), 2.07-1.82 (3H, m), 1.73-1.52 (4H, m), 1.52-1.40 (2H, m), 1.40 (3H, s), 0.81-0.62 (4H, m). | 396 (M + H)⁺ |

TABLE 29

| Ex. | Structural formula | ¹H-NMR | ESI + APCI MS |
|---|---|---|---|
| 90 | | δ: 8.11 (1H, s), 8.04 (1H, br s), 7.91-7.84 (1H, m), 7.59-7.52 (1H, m), 7.43-7.34 (2H, m), 6.08-5.94 (1H, m), 3.39 (2H, dd, J = 6.5, 6.5 Hz), 3.22-3.11 (2H, m), 2.97 (2H, s), 2.11-1.84 (3H, m), 1.75-1.53 (4H, m), 1.53-1.39 (2H, m), 1.39-1.30 (2H, m), 1.19-1.10 (2H, m). | 450 (M + H)⁺ |
| 91 | | δ: 8.11 (1H, s), 7.92-7.83 (1H, m), 7.72 (1H, br s), 7.61-7.50 (1H, m), 7.42-7.33 (2H, m), 6.05-5.94 (1H, m), 3.42-3.31 (7H, m), 3.22-3.12 (2H, m), 2.87 (2H, s), 2.07-1.86 (3H, m), 1.72-1.54 (4H, m), 1.52-1.39 (2H, m), 1.36 (6H, s). | 428 (M + H)⁺ |

TABLE 29-continued

| Ex. | Structural formula | ¹H-NMR | ESI + APCI MS |
|---|---|---|---|
| 92 | | δ: 8.11 (1H, s), 7.90-7.82 (1H, m), 7.72 (1H, br s), 7.59-7.53 (1H, m), 7.43-7.32 (2H, m), 6.07-5.88 (1H, m), 5.21 (1H, br s), 3.64-3.56 (2H, m), 3.38 (2H, dd, J = 6.5, 6.5 Hz), 3.21-3.11 (2H, m), 2.92 (2H, s), 2.08-1.87 (3H, m), 1.74-1.59 (4H, m), 1.51-1.38 (2H, m), 1.29 (6H, s). | 414 (M + H)⁺ |

TABLE 30

| Ex. | Structural formula | ¹H-NMR | ESI + APCI MS |
|---|---|---|---|
| 93 | | δ: 8.65 (1H, br s), 8.11 (1H, s), 7.91-7.83 (1H, m), 7.59-7.52 (1H, m), 7.41-7.33 (2H, m), 6.13-5.94 (1H, m), 3.40-3.28 (4H, m), 2.58 (2H, t, J = 6.0 Hz), 2.23 (2H, t, J = 6.0 Hz), 2.12-1.89 (3H, m), 1.74-1.54 (4H, m), 1.52-1.39 (2H, m), 1.32 (9H, s). | 412 (M + H)⁺ |
| 94 | | δ: 8.12 (1H, s), 7.90-7.85 (1H, m), 7.57-7.51 (1H, m), 7.41-7.33 (2H, m), 6.08-5.95 (1H, m), 3.36 (2H, dd, J = 6.4, 6.4 Hz), 3.32-3.25 (2H, m), 3.14 (2H, s), 3.01 (3H, s), 2.06-1.91 (3H, m), 1.65-1.52 (6H, m), 1.41 (9H, s). | 412 (M + H)⁺ |
| 95 | | δ: 8.03 (1H, br s), 5.67-5.51 (1H, m), 3.27 (2H, dd, J = 6.4, 6.4 Hz), 3.18-3.08 (2H, m), 2.95 (2H, s), 2.60-2.47 (4H, m), 2.53 (3H, s), 1.99-1.73 (7H, m), 1.67-1.51 (4H, m), 1.46-1.30 (4H, m), 1.19-1.08 (2H, m). | 468 (M + H)⁺ |

TABLE 31

| Ex. | Structural formula | ¹H-NMR | ESI + APCI MS |
|---|---|---|---|
| 96 | | δ: 8.04 (1H, br s), 7.16-7.06 (2H, m), 6.89-6.83 (1H, m), 6.21-6.05 (1H, m), 3.83 (3H, s), 3.33 (2H, dd, J = 6.5, 6.5 Hz), 3.20-3.08 (2H, m), 2.95 (2H, s), 2.37 (3H, s), 2.08-1.80 (3H, m), 1.72-1.51 (4H, m), 1.51-1.29 (4H, m), 1.20-1.08 (2H, m). | 454 (M + H)⁺ |
| 97 | | δ: 7.39 (1H, br s), 5.73-5.60 (1H, m), 3.61 (2H, s), 3.53-3.34 (2H, m), 3.34-3.04 (4H, m), 2.57-2.46 (4H, m), 2.52 (3H, s), 2.14-1.36 (13H, m), 1.30 (6H, s). | 432 (M + H)⁺ |

TABLE 31-continued

| Ex. | Structural formula | ¹H-NMR | ESI + APCI MS |
|---|---|---|---|
| 98 | | δ: 7.61 (1H, br s), 7.41 (1H, s), 5.96-5.85 (1H, m), 3.60 (2H, s), 3.32-3.18 (4H, m), 3.06-2.95 (2H, m), 2.86-2.70 (4H, m), 2.06-1.53 (11H, m), 1.50-1.36 (2H, m), 1.30 (6H, s). | 434 (M + H)⁺ |
| 99 | | δ: 7.69 (1H, br s), 6.82-6.73 (1H, m), 6.73-6.69 (1H, m), 6.55-6.50 (2H, m), 3.59 (2H, s), 3.17 (2H, dd, J = 6.6, 6.6 Hz), 3.16-3.09 (2H, m), 2.90 (2H, s), 2.27 (6H, s), 1.98-1.76 (3H, m), 1.67-1.46 (4H, m), 1.50 (6H, s), 1.40-1.31 (2H, m), 1.29 (6H, s). | 460 (M + H)⁺ |

Example 100

N-[(exo)-8-(tert-Butylcarbamoyl)methyl-8-azabicyclo[3.2.1]octan-3-yl]methyl-5-chloro-1-methyl-1H-indole-3-carboxamide

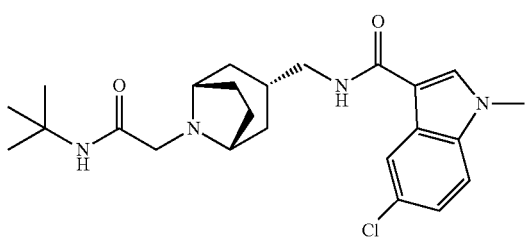 [SMILES: Cn1cc(C(=O)NC[C@@H]2C[C@H]3CC[C@@H](C2)N3CC(=O)NC(C)(C)C)c2cc(Cl)ccc21]

The compound of Example 35 (50 mg) was dissolved in acetonitrile (1 mL), and cesium carbonate (95 mg) and methyl iodide (13 μL) were added thereto. The mixture was stirred for 3 hours at room temperature. Water was added to the reaction solution, extracted with ethyl acetate, and then the organic layer was washed with saturated brine and dried over anhydrous sodium sulfate. The solvent was distilled off under reduced pressure. A residue thus obtained was purified by silica gel column chromatography (NH silica gel, 5% to 40% ethyl acetate/hexane), and thus the title compound (40 mg) was obtained.

¹H-NMR (CDCl₃)δ:7.94-7.92 (1H, m), 7.61 (1H, s), 7.44 (1H, brs), 7.37-7.20 (2H, m), 5.91-5.76 (1H, m), 3.82 (3H, s), 3.36 (2H, dd, J=6.4, 6.4 Hz), 3.18-3.12 (2H, m), 2.85 (2H, s), 2.05-1.82 (3H, m), 1.71-1.35 (6H, m), 1.36 (9H, s).

ESI+APCI-MS Found:m/z 445 (M+H)⁺

Example Compounds 101 to 103 produced by the method similar to that of Example 100 using corresponding raw materials are shown in Table 32.

TABLE 32

| Ex. | Structural formula | ¹H-NMR (CDCl₃) | ESI + APCI MS |
|---|---|---|---|
| 101 | | δ: 7.69-7.65 (1H, m), 7.62-7.58 (1H, m), 7.45 (1H, br s), 7.28-7.22 (1H, m), 7.16-7.09 (1H, m), 6.01-5.85 (1H, m), 3.79 (3H, s), 3.37 (2H, dd, J = 6.4, 6.4 Hz), 3.19-3.10 (2H, m), 2.89-2.82 (2H, m), 2.50 (3H, s), 2.05-1.81 (3H, m), 1.74-1.54 (4H, m), 1.50-1.37 (2H, m), 1.35 (9H, s). | 425 (M + H)⁺ |
| 102 | | δ: 7.71-7.57 (2H, m), 7.47 (1H, br s), 7.31-7.25 (1H, m), 7.09-7.00 (1H, m), 5.97-5.72 (1H, m), 3.82 (3H, s), 3.37 (2H, dd, J = 6.3, 6.3 Hz), 3.24-2.82 (4H, m), 2.07-1.79 (3H, m), 1.74-1.26 (6H, m), 1.36 (9H, s). | 429 (M + H)⁺ |

TABLE 32-continued

| Ex. | Structural formula | $^1$H-NMR (CDCl$_3$) | ESI + APCI MS |
|---|---|---|---|
| 103 | | δ: 7.95-7.77 (2H, m), 7.53-7.17 (4H, m), 6.12-5.89 (1H, m), 4.82-4.52 (1H, m), 3.44-3.29 (2H, m), 3.21-3.04 (2H, m), 2.85 (2H, s), 2.07-1.25 (9H, m), 1.56 (6H, d, J = 6.6 Hz), 1.35 (9H, s). | 439 (M + H)$^+$ |

Example 104

3-Chloro-5-fluoro-N-{(exo)-8-[(2-methoxy-1,1-dimethylethyl) carbamoyl]methyl-8-azabicyclo[3.2.1]octan-3-yl}methylbenzamide

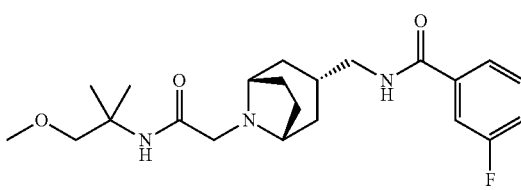

The compound of Reference Example 11 (100 mg) was dissolved in dioxane (3 mL), and 2-chloro-N-(2-methoxy-1,1-dimethylethyl)acetamide (61 mg) and DBU (126 μL) were added thereto. The mixture was stirred for 4 hours under heating at 40° C. The reaction solvent was distilled off under reduced pressure, and a residue thus obtained was purified by silica gel column chromatography (0% to 15% methanol/chloroform), to yield the title compound (83 mg).

$^1$H-NMR (CDCl$_3$)δ:7.70 (1H, brs), 7.52-7.47 (1H, m), 7.41-7.34 (1H, m), 7.29-7.19 (1H, m), 6.14-6.02 (1H, m), 3.40-3.35 (2H, m), 3.38 (3H, s), 3.31 (2H, dd, J=6.3, 6.3 Hz), 3.21-3.10 (2H, m), 2.87 (2H, s), 2.01-1.84 (3H, m), 1.68-1.50 (4H, m), 1.50-1.39 (2H, m), 1.36 (6H, s).

ESI+APCI-MS Found:m/z 440 (M+H)$^+$

Example Compounds 105 to 119 produced by a method similar to that of Example 104 using corresponding raw materials are shown in Table 33 to Table 38.

TABLE 33

| Ex. | Structural formula | $^1$H-NMR (CDCl$_3$) | ESI + APCI MS |
|---|---|---|---|
| 105 | | δ: 7.89-7.84 (1H, m), 7.75 (1H, br s), 7.68 (1H, s), 7.41-7.26 (3H, m), 6.02-5.89 (1H, m), 5.35-5.21 (1H, m), 3.84 (3H, s), 3.61-3.56 (2H, m), 3.39 (2H, dd, J = 6.4, 6.4 Hz), 3.20-3.10 (2H, m), 2.91 (2H, s), 2.05-1.82 (3H, m), 1.75-1.38 (6H, m), 1.27 (6H, s). | 427 (M + H)$^+$ |
| 106 | | δ: 9.97 (1H, br s), 7.54-7.50 (1H, m), 7.42-7.35 (1H, m), 7.26-7.20 (1H, m), 6.33-6.15 (1H, m), 3.38-3.24 (4H, m), 2.57 (2H, t, J = 5.7 Hz), 2.29 (2H, t, J = 5.7 Hz), 2.11-1.84 (3H, m), 1.74-1.55 (4H, m), 1.45-1.31 (2H, m), 1.28-1.18 (2H, m), 1.11-1.02 (2H, m). | 476 (M + H)$^+$ |
| 107 | | δ: 7.42 (1H, br s), 5.63-5.51 (1H, m), 3.21-3.09 (4H, m), 2.83 (2H, s), 2.69-2.60 (1H, m), 2.38-2.27 (2H, m), 2.05-1.71 (9H, m), 1.70-1.49 (8H, m), 1.41-1.27 (2H, m), 1.37 (9H, s). | 402 (M + H)$^+$ |

TABLE 34

| Ex. | Structural formula | ¹H-NMR (CDCl₃) | ESI + APCI MS |
|---|---|---|---|
| 108 | | ¹H-NMR (CD₃OD) δ: 7.77-7.56 (1H, m), 6.61-6.59 (1H, m), 4.03-3.94 (2H, m), 3.71 (2H, s), 3.63 (2H, s), 3.15 (2H, dd, J = 6.4, 6.4 Hz), 2.64-2.56 (1H, m), 2.34-1.55 (21H, m), 1.29 (6H, s). | 418 (M + H)⁺ |
| 109 | | δ: 7.83 (1H, br s), 5.61-5.50 (1H, m), 5.28 (1H, br s), 3.67 (2H, s), 3.19-3.09 (4H, m), 2.91 (2H, s), 2.70-2.59 (1H, m), 2.39-2.25 (2H, m), 2.03-1.46 (25H, m), 1.40-1.25 (2H, m). | 444 (M + H)⁺ |
| 110 | | δ: 7.79 (1H, br s), 7.75-7.72 (1H, m), 7.66-7.60 (1H, m), 7.51-7.45 (1H, m), 7.41-7.34 (1H, m), 6.31-6.10 (1H, m), 4.79 (2H, d, J = 6.2 Hz), 4.52 (2H, d, J = 6.2 Hz), 3.33 (2H, dd, J = 6.6, 6.6 Hz), 3.23-3.14 (2H, m), 2.93 (2H, s), 2.05-1.82 (3H, m), 1.77-1.54 (4H, m), 1.67 (3H, s), 1.50-1.35 (2H, m). | 406 (M + H)⁺ |

TABLE 35

| Ex. | Structural formula | ¹H-NMR (CDCl₃) | ESI + APCI MS |
|---|---|---|---|
| 111 | | δ: 7.79 (1H, br s), 7.54-7.36 (3H, m), 7.25-7.15 (1H, m), 6.26-6.16 (1H, m), 4.79 (2H, d, J = 6.6 Hz), 4.52 (2H, d, J = 6.6 Hz), 3.33 (2H, dd, J = 6.6, 6.6 Hz), 3.23-3.12 (2H, m), 2.93 (2H, s), 2.06-1.82 (3H, m), 1.76-1.55 (4H, m), 1.67 (3H, s), 1.51-1.36 (2H, m). | 390 (M + H)⁺ |
| 112 | | δ: 7.77 (1H, br s), 7.52-7.48 (1H, m), 7.40-7.35 (1H, m), 7.26-7.20 (1H, m), 6.22-6.07 (1H, m), 4.79 (2H, d, J = 6.6 Hz), 4.52 (2H, d, J = 6.6 Hz), 3.33 (2H, dd, J = 6.6, 6.6 Hz), 3.22-3.14 (2H, m), 2.93 (2H, s), 2.01-1.84 (3H, m), 1.72-1.52 (4H, m), 1.67 (3H, s), 1.51-1.34 (2H, m). | 424 (M + H)⁺ |
| 113 | | δ: 7.55-7.35 (4H, m), 7.24-7.15 (1H, m), 6.22-6.10 (1H, m), 3.33 (2H, dd, J = 6.4, 6.4 Hz), 3.18-3.10 (2H, m), 2.85 (2H, s), 2.03-1.85 (3H, m), 1.70-1.53 (4H, m), 1.48-1.38 (2H, m), 1.36 (9H, s). | 376 (M + H)⁺ |

TABLE 36

| Ex. | Structural formula | ¹H-NMR (CDCl₃) | ESI + APCI MS |
|---|---|---|---|
| 114 | | δ: 8.02 (1H, br s), 7.53-7.47 (1H, m), 7.41-7.33 (1H, m), 7.29-7.19 (1H, m), 6.17-6.05 (1H, m), 3.33 (2H, dd, J = 6.6, 6.6 Hz), 3.21-3.09 (2H, m), 2.96 (2H, s), 2.02-1.85 (3H, m), 1.70-1.49 (4H, m), 1.49-1.29 (4H, m), 1.20-1.07 (2H, m). | 462 (M + H)⁺ |
| 115 | | δ: 7.66 (1H, br s), 7.57-7.47 (1H, m), 7.43-7.34 (1H, m), 7.29-7.16 (1H, m), 6.30-6.13 (1H, m), 3.32 (2H, dd, J = 6.4, 6.4 Hz), 3.19-3.05 (2H, m), 2.89 (2H, s), 2.07-1.81 (3H, m), 1.76-1.50 (4H, m), 1.50-1.32 (2H, m), 1.39 (3H, s), 0.85-0.60 (4H, m). | 408 (M + H)⁺ |

TABLE 37

| Ex. | Structural formula | ¹H-NMR (CDCl₃) | ESI + APCI MS |
|---|---|---|---|
| 116 | | δ: 7.70 (1H, br s), 7.52-7.48 (1H, m), 7.40-7.34 (1H, m), 7.27-7.20 (1H, m), 6.17-6.03 (1H, m), 5.26-5.07 (1H, m), 3.60 (2H, s), 3.33 (2H, dd, J = 6.5, 6.5 Hz), 3.21-3.09 (2H, m), 2.91 (2H, s), 2.04-1.83 (3H, m), 1.71-1.47 (4H, m), 1.46-1.33 (2H, m), 1.30 (6H, s). | 426 (M + H)⁺ |
| 117 | | δ: 7.53-7.48 (1H, m), 7.41-7.34 (1H, m), 7.26-7.18 (1H, m), 6.22-6.06 (1H, m), 3.80-3.72 (2H, m), 3.71-3.64 (2H, m), 3.37 (2H, s), 3.30 (2H, dd, J = 6.4, 6.4 Hz), 3.26-3.19 (2H, m), 3.12 (2H, s), 2.05-1.86 (3H, m), 1.72-1.36 (6H, m), 1.42 (6H, s). | 452 (M + H)⁺ |

TABLE 38

| Ex. | Structural formula | ¹H-NMR (CDCl₃) | ESI + APCI MS |
|---|---|---|---|
| 118 | | δ: 7.67-7.60 (1H, m), 7.55-7.47 (1H, m), 7.23-7.16 (1H, m), 6.88-6.66 (1H, m), 3.65-3.48 (2H, m), 3.43-3.30 (4H, m), 2.98 (3H, s), 2.24-1.97 (3H, m), 1.97-1.75 (2H, m), 1.75-1.56 (4H, m), 1.41 (9H, s). | 424 (M + H)⁺ |
| 119 | | δ: 7.92-7.81 (2H, m), 7.67 (1H, s), 7.43-7.24 (3H, m), 6.01-5.93 (1H, m), 3.83 (3H, s), 3.45 (2H, s), 3.42-3.32 (5H, m), 3.16-3.09 (2H, m), 2.93 (2H, s), 2.06-1.84 (3H, m), 1.71-1.54 (4H, m), 1.52-1.38 (2H, m), 0.90-0.78 (4H, m). | 439 (M + H)⁺ |

Example 120

N-tert-Butyl-2-[(exo)-3-(4-methyl-1H-benzimidazol-2-yl)methyl-8-azabicyclo[3.2.1]octan-8-yl]acetamide

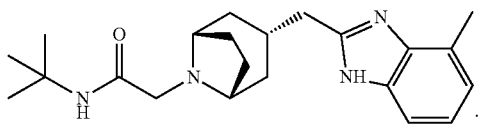 [SMILES: Cc1cccc2[nH]c(C[C@@H]3C[C@H]4CC[C@@H](C3)N4CC(=O)NC(C)(C)C)nc12]

The compound of Reference Example 5 (150 mg) was dissolved in acetonitrile (2 mL), and 2,3-diaminotoluene (60 mg) and PyBOP (269 mg) were added thereto. Subsequently, triethylamine (262 μL) was added to the mixture, and the mixture was stirred for 16 hours at room temperature. The reaction solvent was distilled off under reduced pressure, water was added to the residue, and extracted with chloroform. The organic layer was dried over anhydrous sodium sulfate, and the solvent was distilled off under reduced pressure. A residue thus obtained was purified by silica gel column chromatography (0% to 15% methanol/chloroform), and thus a crude product was obtained.

The crude product thus obtained was dissolved in acetic acid (2 mL), and the solution was stirred for 4 hours under heating at 80° C. The reaction solvent was distilled off under reduced pressure, 1 mol/L hydrochloric acid was added to the residue, and the mixture was washed with chloroform. A 10% aqueous solution of sodium hydroxide was added to the aqueous layer to adjust the aqueous layer to pH 10 to 11, and extracted with chloroform. The organic layer was washed with saturated brine and then was dried over anhydrous sodium sulfate, and the solvent was distilled off under reduced pressure. A residue thus obtained was purified by silica gel column chromatography (0% to 10% methanol/chloroform), and thus the title compound (118 mg) was obtained.

$^1$H-NMR (CDCl$_3$)δ:9.25(1H,brs),7.65-7.18(2H,m),7.17-7.08(1H,m),7.06-6.98(1H,m),3.14-3.06(2H,m),2.85(2H,s),2.76(2H,d,J=7.1 Hz),2.70-2.48(3H,m),2.31-2.10 (1H,m),1.92-1.82(2H,m),1.71-1.52(4H,m),1.52-1.23(2H,m),1.37 (9H,s).

ESI+APCI-MS Found:m/z 369 (M+H)$^+$

Example Compounds 121 and 122 produced by a method similar to that of Example 120 using corresponding raw materials are shown in Table 39.

TABLE 39

| Ex. | Structural formula | $^1$H-NMR (CDCl$_3$) | ESI + APCI MS |
|---|---|---|---|
| 121 | | δ: 9.03-8.79 (1H, m), 7.43 (1H, br s), 7.03-6.56 (2H, m), 3.83 (3H, s), 3.18-3.05 (2H, m), 2.86 (2H, s), 2.74 (2H, d, J = 7.0 Hz), 2.30-2.07 (1H, m), 1.97-1.84 (2H, m), 1.69-1.40 (6H, m), 1.36 (9H, s). | 403 (M + H)$^+$ |
| 122 | | δ: 9.12-8.85 (1H, m), 7.54-6.85 (3H, m), 4.30-3.82 (6H, m), 3.17-3.05 (2H, m), 2.85 (2H, s), 2.74 (2H, d, J = 7.1 Hz), 2.33-2.10 (1H, m), 1.96-1.23 (8H, m), 1.36 (9H, s). | 415 (M + H)$^+$ |

Example 123

N-tert-Butyl-2-[(exo)-3-(5,6-dihydro-1H-[1,4]dioxino[2,3-e]benzimidazol-2-yl)methyl-8-azabicyclo[3.2.1]octan-8-yl]acetamide

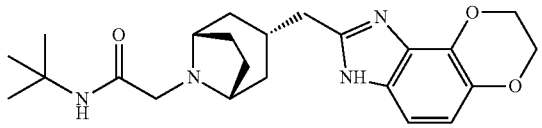 [SMILES: CC(C)(C)NC(=O)CN1[C@@H]2CC[C@H]1C[C@H](Cc1nc3c4c(ccc3[nH]1)OCCO4)C2]

The compound of Reference Example 13 (230 mg) was dissolved in dioxane (3 mL), and 2-chloro-N-(2-methoxy-1,1-dimethylethyl)acetamide (97 mg) and DBU (296 μL) were added thereto. The mixture was stirred for 4 hours under heating at 40° C., and then was stirred for another 4 hours under heating at 50° C. The reaction solvent was distilled off under reduced pressure, and a residue thus obtained was purified by silica gel column chromatography (2% to 20% methanol/chloroform), to yield the title compound (203 mg).

$^1$H-NMR (CDCl$_3$)δ:9.15-8.92 (1H,m),7.44(1H,brs),7.21-6.74(2H,m),4.45-4.27(4H,m),3.13-3.04(2H,m),2.85(2H,s),2.72(2H,d,J=7.1 Hz),2.31-2.07(1H,m),1.94-1.78(2H,m),1.67-1.38(6H,m),1.36(9H,s).

ESI+APCI-MS Found:m/z 413 (M+H)$^+$

Example Compounds 124 and 125 produced by a method similar to that of Example 123 using corresponding raw materials are shown in Table 40.

TABLE 40

| Ex. | Structural formula | $^1$H-NMR (CDCl$_3$) | ESI + APCI MS |
|---|---|---|---|
| 124 | | δ: 9.57-9.19 (1H, m), 7.53-6.95 (3H, m), 6.73-6.62 (1H, m), 4.04-3.90 (3H, m), 3.14-3.03 (2H, m), 2.84 (2H, s), 2.75 (2H, d, J = 7.0 Hz), 2.28-2.12 (1H, m), 1.96-1.77 (2H, m), 1.74-1.22 (6H, m), 1.36 (9H, s). | 385 (M + H)$^+$ |
| 125 | | δ: 8.88 (1H, br s), 8.05 (1H, br s), 7.24-6.70 (2H, m), 4.50-4.25 (4H, m), 3.16-3.02 (2H, m), 2.95 (2H, s), 2.73 (2H, d, J = 7.3 Hz), 2.38-2.10 (1H, m), 1.97-1.77 (2H, m), 1.74-1.52 (4H, m), 1.52-1.39 (2H, m), 1.38-1.30 (2H, m), 1.20-1.09 (2H, m). | 465 (M + H)$^+$ |

Example 126

2-[(endo)-8-(tert-Butylcarbamoyl)methyl-8-azabicyclo[3.2.1]octan-3-yl]-N-(2-oxaadamantan-1-yl) acetamide

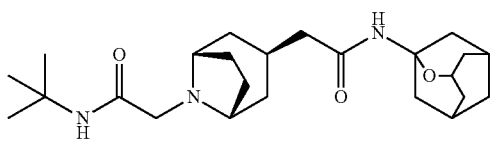 [SMILES: CC(C)(C)NC(=O)CN1[C@@H]2CC[C@H]1C[C@@H](CC(=O)NC13CC4CC(CC(C4)O1)C3)C2]

The compound of Reference Example 16 (4.08 g) was suspended in acetonitrile (51 mL), and 1-oxaadamantaneamine (2.31 g) and PyBOP (7.33 g) were added thereto. Subsequently, triethylamine (8.93 mL) was added to the mixture under ice cooling, and the mixture was stirred for 2.5 hours at room temperature. The reaction solvent was distilled off under reduced pressure, a saturated aqueous solution of sodium hydrogen carbonate was added to the residue, and extracted with chloroform. The organic layer was washed with saturated brine and then dried over anhydrous sodium sulfate, and the solvent was distilled off under reduced pressure. Acetonitrile was added to a residue thus obtained, and the mixture was stirred at room temperature. Subsequently, a precipitate was collected by filtration and washed with acetonitrile, and thus the title compound (4.54 g) was obtained.

$^1$H-NMR (CDCl$_3$)δ:7.46(1H,brs),5.62-5.45(1H,m),4.30-4.13(H,m),3.14-3.02(2H,m),2.82(2H,s),2.42-2.05(9H,m),2.06-1.52(12H,m),1.43-1.30(2H,m),1.36(9H,s).

ESI+APCI-MS Found:m/z 418 (M+H)$^+$

Example 127

2-[(endo)-8-(tert-Butylcarbamoyl)methyl-8-azabicyclo[3.2.1]octan-3-yl]-N-(2,2-dimethylpropyl) acetamide

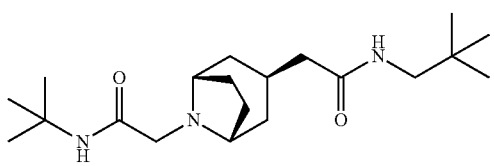 [SMILES: CC(C)(C)CNC(=O)C[C@H]1C[C@H]2CC[C@@H](C1)N2CC(=O)NC(C)(C)C]

The title compound (23 mg) was obtained by a method similar to that of Example 126, using the compound of Reference Example 16 (100 mg) and neopentylamine (57 mg).

$^1$H-NMR (CDCl$_3$)δ:7.45(1H,brs),5.46-5.34(1H,m),3.14-3.04 (4H,m),2.82(2H,s),2.39-2.27(3H,m),2.23-2.06 (2H,m), 2.06-1.88(2H,m),1.69-1.55(2H,m),1.42-1.32(2H,m),1.37 (9H,s),0.91(9H,s).

ESI+APCI-MS Found:m/z 352 (M+H)$^+$

Example 128

N-(Adamantan-1-yl)-2-{(endo)-8-[2-hydroxy-3-(2-methoxyphenoxy) propyl]-8-azabicyclo[3.2.1]octan-3-yl}acetamide

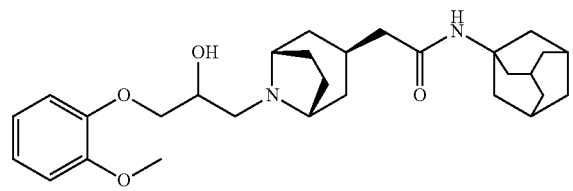 [SMILES: COc1ccccc1OCC(O)CN1[C@@H]2CC[C@H]1C[C@@H](CC(=O)NC13CC4CC(CC(C4)C1)C3)C2]

The compound of Reference Example 20 (150 mg) was dissolved in a 1:1 mixed liquid (2 mL) of acetonitrile and water, and 1,2-epoxy-3-(2-methoxyphenoxy)propane (65 mg) and potassium carbonate (124 mg) were added thereto. The mixture was stirred for 4 hours under heating at 70° C., and then the mixture was heated for 10 minutes at 140° C. in a microwave reaction apparatus. The reaction solvent was distilled off under reduced pressure, water was added to the residue, and extracted with chloroform. The organic layer was dried over anhydrous sodium sulfate, and the solvent was distilled off under reduced pressure. A residue thus obtained was purified by silica gel column chromatography (NH silica gel, 2% to 5% methanol/chloroform), and thus the title compound (50 mg) was obtained.

$^1$H-NMR (CDCl$_3$)δ:7.02-6.83(4H,m),5.04(1H,brs),4.12-3.93(4H,m),3.85(3H,s),3.25-3.12(2H,m),2.63(1H,dd, J=12.7,3.9 Hz),2.47-1.49(25H,m),1.39-1.24(2H,m).

ESI+APCI-MS Found:m/z 483 (M+H)$^+$

Example 129

N-(Adamantan-1-yl)-2-[(endo)-8-(tert-butylcarbamoyl)methyl-8-azabicyclo[3.2.1]octan-3-yl]acetamide

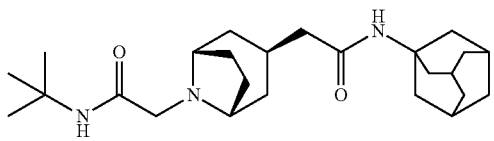 [SMILES: CC(C)(C)NC(=O)CN1[C@@H]2CC[C@H]1C[C@@H](CC(=O)NC13CC4CC(CC(C4)C1)C3)C2]

The compound of Reference Example 21 (100 mg) was suspended in dioxane (3 mL), and 2-chloro-N-tert-butylacetamide (53 mg) and DBU (220 μL) were added thereto. The mixture was stirred for 14 hours at room temperature. The reaction solvent was distilled off under reduced pressure, and a residue thus obtained was purified by silica gel column chromatography (3% to 8% methanol/chloroform), to yield the title compound (90 mg).

$^1$H-NMR (CDCl$_3$)δ:7.46(1H,brs),5.06(1H,brs),3.12-3.04(2H,m),2.81(2H,s),2.33-2.03(7H,m),2.02-1.89(7H,m),1.72-1.56(10H,m),1.37-1.29(2H,m),1.37(9H,s).

ESI+APCI-MS Found:m/z 416 (M+H)$^+$

Example Compounds 130 and 131 produced by a method similar to that of Example 129 using corresponding raw materials are shown in Table 41.

TABLE 41

| Ex. | Structural formula | $^1$H-NMR (CDCl$_3$) | ESI + APCI MS |
|---|---|---|---|
| 130 | | δ: 8.76 (1H, br s), 5.05 (1H, br s), 3.29-3.16 (2H, m), 2.55 (2H, dd, J = 5.8, 5.8 Hz), 2.35-2.18 (5H, m), 2.18-2.03 (5H, m), 2.02-1.93 (8H, m), 1.71-1.57 (8H, m), 1.43-1.35 (2H, m), 1.34 (9H, s). | 430 (M + H)$^+$ |
| 131 | | δ: 7.47 (1H, br s), 5.55 (1H, br s), 3.17-3.01 (2H, m), 2.81 (2H, s), 2.43-2.37 (1H, m), 2.34-2.20 (5H, m), 2.18-1.92 (8H, m), 1.90-1.82 (2H, m), 1.69-1.51 (6H, m), 1.45-1.32 (2H, m), 1.36 (9H, s). | 402 (M + H)$^+$ |

Example 132

N-[(endo)-8-(tert-Butylcarbamoyl)methyl-8-azabicyclo[3.2.1]octan-3-yl]methyl-3-chloro-5-methoxybenzamide

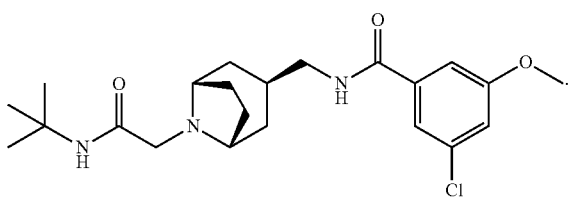 [SMILES: COc1cc(Cl)cc(C(=O)NC[C@H]2C[C@H]3CC[C@@H](C2)N3CC(=O)NC(C)(C)C)c1]

The compound of Reference Example 23 (70 mg) was suspended in dichloromethane (1 mL), and 3-chloro-5-methoxybenzoic acid (44 mg) and HATU (90 mg) were added thereto. Subsequently, triethylamine (108 μL) was added to the mixture, and the mixture was stirred for 4 hours at room temperature. 1 mol/L hydrochloric acid was added to the reaction solution, and the mixture was washed with chloroform. Subsequently, basicity of the aqueous layer was adjusted with a 2 mol/L aqueous solution of sodium hydroxide, and extracted with chloroform. The organic layer was dried over anhydrous sodium sulfate, and the solvent was distilled off under reduced pressure. A residue thus obtained was purified by silica gel column chromatography (NH silica gel, 25% to 50% ethyl acetate/hexane), and thus the title compound (54 mg) was obtained.

$^1$H-NMR (CDCl$_3$)δ:7.43(1H,brs),7.30-7.20(2H,m),7.05-6.99(1H,m),6.12-6.00(1H,m),3.84(3H,s),3.59-3.46(2H,m),3.15-3.06(2H,m),2.86(2H,s),2.14-1.87(5H,m),1.87-1.73(2H,m),1.55-1.43(2H,m),1.37(9H,s).

ESI+APCI-MS Found:m/z 422 (M+H)$^+$

Example Compounds 133 to 143 produced by a method similar to that of Example 132 using corresponding raw materials are shown in Table 42 to Table 45.

TABLE 42

| Ex. | Structural formula | $^1$H-NMR (CDCl$_3$) | ESI + APCI MS |
|---|---|---|---|
| 133 | | δ: 8.11 (1H, s), 7.90-7.85 (1H, m), 7.58-7.52 (1H, m), 7.44 (1H, br s), 7.42-7.32 (2H, m), 6.07-5.90 (1H, m), 3.58 (2H, dd, J = 7.8, 6.1 Hz), 3.18-3.04 (2H, m), 2.86 (2H, s), 2.14-1.90 (5H, m), 1.87-1.77 (2H, m), 1.59-1.49 (2H, m), 1.37 (9H, s). | 398 (M + H)$^+$ |
| 134 | | δ: 7.91-7.84 (1H, m), 7.67 (1H, s), 7.47 (1H, br s), 7.41-7.22 (3H, m), 6.03-5.84 (1H, m), 3.83 (3H, s), 3.59 (2H, dd, J = 7.5, 6.2 Hz), 3.15-3.04 (2H, m), 2.86 (2H, s), 2.14-1.78 (7H, m), 1.63-1.49 (2H, m), 1.37 (9H, s). | 411 (M + H)$^+$ |

TABLE 43

| Ex. | Structural formula | $^1$H-NMR (CDCl$_3$) | ESI + APCI MS |
|---|---|---|---|
| 135 | | δ: 7.42 (1H, br s), 6.45-6.36 (1H, m), 6.33 (1H, s), 5.55-5.48 (1H, m), 4.90-4.77 (1H, m), 3.38-3.22 (2H, m), 3.12-2.98 (2H, m), 2.92-2.80 (1H, m), 2.82 (2H, s), 2.46-2.32 (1H, m), 2.29 (6H, s), 2.02-1.19 (14H, m), 1.35 (9H, s). | 471 (M + H)$^+$ |
| 136 | | δ: 7.44 (1H, br s), 5.63-5.47 (1H, m), 3.46 (2H, dd, J = 8.1, 6.2 Hz), 3.15-3.05 (2H, m), 2.85 (2H, s), 2.57-2.48 (4H, m), 2.52 (3H, s), 2.10-1.72 (11H, m), 1.63-1.30 (2H, m), 1.37 (9H, s). | 416 (M + H)$^+$ |

TABLE 43-continued

| Ex. | Structural formula | ¹H-NMR (CDCl₃) | ESI + APCI MS |
|---|---|---|---|
| 137 | | δ: 7.41 (1H, br s), 6.27 (1H, s), 6.00-5.90 (1H, m), 4.11 (3H, s), 3.47 (2H, dd, J = 8.0, 6.3 Hz), 3.17-3.05 (2H, m), 3.04-2.89 (1H, m), 2.86 (2H, s), 2.11-1.72 (7H, m), 1.60-1.40 (2H, m), 1.37 (9H, s), 1.25 (6H, d, J = 7.0 Hz). | 404 (M + H)⁺ |

TABLE 44

| Ex. | Structural formula | ¹H-NMR (CDCl₃) | ESI + APCI MS |
|---|---|---|---|
| 138 | | δ: 7.43 (1H, br s), 6.80-6.71 (1H, m), 6.71 (1H, s), 6.52 (2H, s), 3.38 (2H, dd, J = 8.1, 6.2 Hz), 3.12-3.02 (2H, m), 2.83 (2H, s), 2.27 (6H, s), 2.07-1.72 (7H, m), 1.51 (6H, s), 1.47-1.31 (2H, m), 1.36 (9H, s). | 444 (M + H)⁺ |
| 139 | | δ: 7.45 (1H, s), 5.62-5.32 (1H, m), 3.48-3.20 (2H, m), 3.20-2.96 (2H, m), 2.84 (2H, s), 2.16-1.50 (24H, m), 1.49-1.19 (2H, m), 1.36 (9H, s). | 430 (M + H)⁺ |
| 140 | | δ: 7.37 (1H, br s), 5.64-5.53 (1H, m), 3.38 (2H, dd, J = 8.2, 6.2 Hz), 3.25-3.09 (2H, m), 2.95 (2H, br s), 2.70-2.57 (1H, m), 2.38-2.26 (2H, m), 2.12-1.71 (13H, m), 1.69-1.53 (4H, m), 1.52-1.41 (2H, m), 1.36 (9H, s). | 402 (M + H)⁺ |

TABLE 45

| Ex. | Structural formula | ¹H-NMR (CDCl₃) | ESI + APCI MS |
|---|---|---|---|
| 141 | | δ: 7.55-7.49 (1H, m), 7.45-7.34 (2H, m), 7.28-7.20 (1H, m), 6.22-6.03 (1H, m), 3.53 (2H, dd, J = 6.9, 6.9 Hz), 3.16-3.05 (2H, m), 2.85 (2H, s), 2.14-1.91 (5H, m), 1.86-1.72 (2H, m), 1.53-1.41 (2H, m), 1.37 (9H, s). | 410 (M + H)⁺ |
| 142 | | δ: 7.62 (2H, d, J = 1.8 Hz), 7.49 (1H, t, J = 1.8 Hz), 7.41 (1H, br s), 6.13-6.00 (1H, m), 3.59-3.46 (2H, m), 3.14-3.07 (2H, m), 2.86 (2H, s), 2.12-1.90 (5H, m), 1.84-1.73 (2H, m), 1.51-1.43 (2H, m), 1.37 (9H, s). | 426 (M + H)⁺ |

TABLE 45-continued

| Ex. | Structural formula | $^1$H-NMR (CDCl$_3$) | ESI + APCI MS |
|---|---|---|---|
| 143 | | δ: 7.76-7.72 (1H, m), 7.65-7.60 (1H, m), 7.51-7.33 (3H, m), 6.17-6.06 (1H, m), 3.59-3.50 (2H, m), 3.16-3.05 (2H, m), 2.86 (2H, s), 2.15-1.87 (5H, m), 1.85-1.75 (2H, m), 1.54-1.43 (2H, m), 1.37 (9H, s). | 392 (M + H)$^+$ |

Example 144

N-[(endo)-8-(tert-Butylcarbamoyl)methyl-8-azabicyclo[3.2.1]octan-3-yl]methyladamantane-1-carboxamide

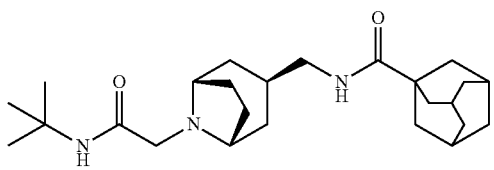 [SMILES: CC(C)(C)NC(=O)CN1[C@@H]2CC[C@H]1C[C@@H](CNC(=O)C13CC4CC(CC(C4)C1)C3)C2]

The title compound (105 mg) was obtained by a method similar to that of Example 129, using the compound of Reference Example 27 (120 mg).

$^1$H-NMR (CDCl$_3$)δ: 7.45(1H,brs),5.71-5.60(1H,m),3.36-3.28(2H,m),3.16-2.99 (2H,m),2.84(2H,s),2.13-1.89(7H,m), 1.88-1.63(15H,m),1.44-1.34(2H,m),1.36(9H,s).

ESI+APCI-MS Found:m/z 416 (M+H)$^+$

Example 145

N-tert-Butyl-2-[(endo)-3-(4-methoxy-1H-benzimidazol-2-yl)methyl-8-azabicyclo[3.2.1]octan-8-yl]acetamide

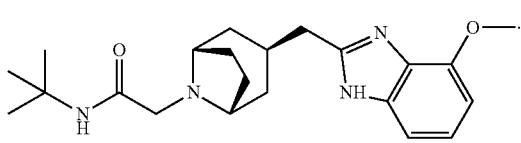 [SMILES: COc1cccc2[nH]c(C[C@H]3C[C@H]4CC[C@@H](C3)N4CC(=O)NC(C)(C)C)nc12]

The compound of Reference Example 16 (500 mg) was suspended in acetonitrile (6 mL), and 1,2-diamino-3-methoxybenzene dihydrochloride (348 mg) was added thereto. Subsequently, PyBOP (898 mg) and triethylamine (929 µL) were added to the mixture under ice cooling, and the mixture was stirred for 4 hours at room temperature. The reaction solvent was distilled off under reduced pressure, water was added to the residue, and extracted with ethyl acetate. Subsequently, the extract was dried over anhydrous sodium sulfate, and the solvent was distilled off under reduced pressure. A residue thus obtained was purified by silica gel column chromatography (0% to 15% methanol/ethyl acetate), and thus a crude product was obtained.

The crude product thus obtained was dissolved in acetic acid (6 mL), and the solution was stirred for 4 hours under heating at 80° C. The reaction solvent was distilled off under reduced pressure, 1 mol/L hydrochloric acid was added to the residue, and the mixture was washed with chloroform. A 10% aqueous solution of sodium hydroxide was added to the aqueous layer to adjust the pH of the aqueous layer to 10 to 11, and extracted with chloroform. The organic layer was dried over anhydrous sodium sulfate, and the solvent was distilled off under reduced pressure. A residue thus obtained was purified by silica gel column chromatography (0% to 15% methanol/chloroform), and the title compound (426 mg) was obtained.

$^1$H-NMR (CDCl$_3$)δ:7.43(1H,brs),7.37-6.95(2H,m),6.73-6.64(1H,m),4.04-3.92(3H,m),3.17-3.06(2H,m),3.03(2H,d, J=8.4 Hz),2.84(2H,s),2.54-2.33(1H,m),2.21-1.93(4H,m), 1.88-1.70(2H,m),1.51-1.40(2H,m),1.35(9H,s).

ESI+APCI-MS Found:m/z 385 (M+H)$^+$

Example Compounds 146 to 148 produced by a method similar to that of Example 145 using corresponding raw materials are shown in Table 46.

TABLE 46

| Ex. | Structural formula | $^1$H-NMR (CDCl$_3$) | ESI + APCI MS |
|---|---|---|---|
| 146 | | δ: 9.24-8.96 (1H, m), 7.43 (1H, br s), 7.30-5.98 (2H, m), 3.86-3.60 (3H, m), 3.21-2.91 (4H, m), 2.85 (2H, s), 2.50-1.64 (5H, m), 1.60-1.18 (4H, m), 1.36 (9H, s). | 403 (M + H)$^+$ |

TABLE 46-continued

| Ex. | Structural formula | $^1$H-NMR (CDCl$_3$) | ESI + APCI MS |
|---|---|---|---|
| 147 | | δ: 7.45 (1H, br s), 7.30-6.94 (3H, m), 3.19-3.05 (2H, m), 3.05 (2H, d, J = 8.4 Hz), 2.85 (2H, s), 2.72-2.36 (4H, m), 2.18-1.92 (4H, m), 1.86-1.72 (2H, m), 1.54-1.39 (2H, m), 1.36 (9H, s). | 369 (M + H)$^+$ |
| 148 | | δ: 8.95-8.64 (1H, m), 7.51-6.81 (3H, m), 4.34-3.82 (6H, m), 3.18-3.05 (2H, m), 3.00 (2H, d, J = 8.1 Hz), 2.84 (2H, s), 2.48-1.20 (9H, m), 1.36 (9H, s). | — |

Example 149

N-tert-Butyl-2-[(endo)-3-(5,6-dihydro-1H-[1, 4]dioxino[2,3-e]benzimidazol-2-yl)methyl-8-azabicyclo[3.2.1]octan-8-yl]acetamide dihydrochloride

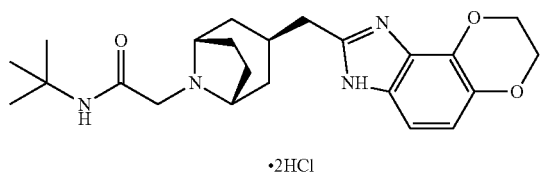 [SMILES: CC(C)(C)NC(=O)CN1[C@@H]2CC[C@H]1C[C@@H](Cc1nc3c4c(ccc3[nH]1)OCCO4)C2]

·2HCl

The compound of Reference Example 16 (150 mg) was suspended in acetonitrile (2 mL), and 2,3-dihydrobenzo[1,4]dioxin-5,6-diamine dihydrochloride (118 mg) and PyBOP (269 mg) were added thereto. Subsequently, triethylamine (279 µL) was added to the mixture, and the mixture was stirred for 1.5 hours at room temperature. The reaction solvent was distilled off under reduced pressure, water was added to the residue, and extracted with chloroform. The organic layer was dried over anhydrous sodium sulfate, and the solvent was distilled off under reduced pressure. A residue thus obtained was purified by silica gel column chromatography (0% to 10% methanol/chloroform), and a crude product was obtained.

The crude product thus obtained was dissolved in acetic acid (2 mL), and the solution was stirred for 4 hours under heating at 80° C. The reaction solvent was distilled off under reduced pressure, 1 mol/L hydrochloric acid was added to the residue, and the mixture was washed with chloroform. Subsequently, the aqueous layer was adjusted to pH 10 to 11 with a 2 mol/L aqueous solution of sodium hydroxide, and extracted with chloroform. The organic layer was washed with saturated brine and then was dried over anhydrous sodium sulfate, and the solvent was distilled off under reduced pressure. A residue thus obtained was purified by silica gel column chromatography (0% to 10% methanol/chloroform), and a crude product was obtained.

A 2 mol/L ethanol solution of hydrogen chloride (2 mL) was added to the crude product thus obtained, and the mixture was stirred for 15 minutes at room temperature. The reaction solvent was distilled off under reduced pressure, ethyl acetate was added to the residue, and the mixture was stirred at room temperature. A precipitate was collected by filtration, and the precipitate was washed with ethyl acetate, to yield the title compound (76 mg).

$^1$H-NMR (DMSO-d$_6$)δ:9.66(1H,brs),8.46-8.26(1H,m),7.20(1H,d,J=8.6 Hz),7.06(1H,d,J=8.6 Hz),4.52-4.42(2H,m),4.42-4.32(2H,m),3.94-3.82(2H,m),3.78-3.69(2H,m),3.42-3.28(2H,m),2.61-2.39(3H,m),2.32-2.14(4H,m),1.77-1.52(2H,m),1.30(9H,s).

ESI+APCI-MS Found:m/z 413 (M+H)+

Example 150

1-(2-Methoxyphenoxy)-3-[(endo)-3-(4-methyl-1H-benzimidazol-2-yl)methyl-8-azabicyclo[3.2.1]octan-8-yl]propan-2-ol

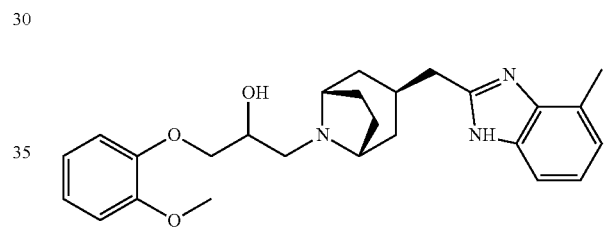

The compound of Reference Example 29 (70 mg) was dissolved in ethanol (2 mL), and 1,2-epoxy-3-(2-methoxyphenoxy)propane (49 mg) was added thereto. The mixture was stirred for 69 hours at room temperature. The reaction solvent was distilled off under reduced pressure, and a residue thus obtained was purified by silica gel column chromatography (NH silica gel, 50% to 100% ethyl acetate/hexane, 5% to 20% methanol/chloroform), to yield the title compound (108 mg).

$^1$H-NMR (CDCl$_3$)δ:9.14-8.83(1H,m),7.65-6.80(7H,m),4.10-3.92(3H,m),3.84(3H,s),3.28-3.13(2H,m),3.04(2H,d,J=8.6 Hz),2.75-2.26(6H,m),2.24-1.91(4H,m),1.90-1.66(2H,m),1.49-1.30(2H,m).

ESI+APCI-MS Found:m/z 436 (M+H)$^+$

Example 151

N-tert-Butyl-3-[(endo)-3-(4-methyl-1H-benzimidazol-2-yl)methyl-8-azabicyclo[3.2.1]octan-8-yl]propanamide

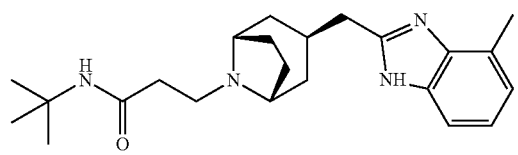 [SMILES: Cc1cccc2[nH]c(C[C@H]3C[C@H]4CC[C@@H](C3)N4CCC(=O)NC(C)(C)C)nc12]

The compound of Reference Example 29 (180 mg) was dissolved in acetonitrile (4 mL), and 3-bromo-N-tert-butyl-propanamide (154 mg) and potassium carbonate (107 mg) were added thereto. Subsequently, water (2 mL) was added thereto, and the mixture was stirred for 24 hours under heating at 80° C. Water was added to the reaction solution, and extracted with chloroform. The organic layer was dried over anhydrous sodium sulfate, and the solvent was distilled off under reduced pressure. A residue thus obtained was purified by silica gel column chromatography (NH silica gel, 5% to 22% methanol/chloroform), and thus the title compound (270 mg) was obtained.

$^1$H-NMR (CDCl$_3$)δ: 9.96-9.22(1H,m),8.79(1H,brs),7.60-7.19(1H,m),7.18-7.06(1H,m),7.06-6.99(1H,m),3.32-3.17(2H,m),3.08(2H,d,J=8.6 Hz),2.70-2.34(4H,m),2.56(2H,t,J=5.8 Hz),2.22(2H,t,J=5.8 Hz),2.16-1.93(4H,m),0.93-1.63(2H,m),1.58-1.41(2H,m),1.33(9H,s).

ESI+APCI-MS Found:m/z 383 (M+H)+

Example 152

2-[(endo)-8-(tert-Butylcarbamoyl)methyl-8-azabicyclo[3.2.1]octan-3-yl]-N-(2-oxaadamantan-1-yl)acetamide hydrochloride

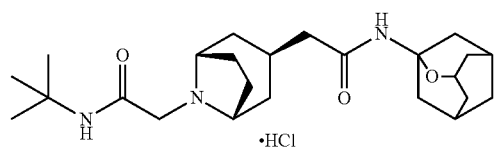 [SMILES: CC(C)(C)NC(=O)CN1[C@@H]2CC[C@H]1C[C@@H](CC(=O)NC13CC4CC(CC(C4)O1)C3)C2 ; Cl]

The compound of Example 126 (811 mg) was dissolved in a 1:1 mixed liquid (8 mL) of ethanol and chloroform, and a 2 mol/L ethanol solution of hydrogen chloride (3.9 mL) was added thereto. The mixture was stirred for 30 minutes at room temperature. The reaction solvent was distilled off under reduced pressure, acetonitrile was added to the residue, and the mixture was stirred at room temperature. A precipitate was collected by filtration and was washed with acetonitrile, and thus the title compound (803 mg) was obtained.

$^1$H-NMR (CD$_3$OD)δ: 8.04(1H,brs),4.20-4.09(1H,m),4.00-3.63(4H,m),2.52-2.09(13H,m),2.06-1.59(10H,m),1.36(9H,s).

ESI+APCI-MS Found:m/z 418 (M+H)$^+$

Example Compounds 153 to 155 produced by a method similar to that of Example 152 using corresponding raw materials are shown in Table 47.

TABLE 47

| Ex. | Structural formula | $^1$H-NMR (CD$_3$OD) | ESI + APCI MS |
|---|---|---|---|
| 153 | | δ: 7.86-7.78 (1H, m), 4.04-3.94 (2H, m), 3.70 (2H, s), 3.39-3.21 (2H, m), 2.79 (3H, s), 2.62 (3H, s), 2.36-2.17 (3H, m), 2.11-1.69 (6H, m), 1.36 (9H, s). | 393 (M + H)$^+$ |
| 154 | | δ: 7.84 (1H, br s), 7.12-6.97 (2H, m), 4.06-4.00 (2H, m), 3.90 (3H, s), 3.72 (2H, s), 3.14 (2H, d, J = 7.0 Hz), 2.66-2.49 (1H, m), 2.35-2.20 (2H, m), 2.14-2.03 (2H, m), 1.99-1.92 (4H, m), 1.36 (9H, s). | 403 (M + H)$^+$ |
| 155 | | δ: 7.86 (1H, br s), 7.42 (1H, d, J = 9.0 Hz), 7.36 (1H, d, J = 9.0 Hz), 4.08 (3H, s), 4.06-3.98 (2H, m), 3.96 (3H, s), 3.77 (2H, s), 3.46 (2H, d, J = 8.1 Hz), 2.72-2.46 (3H, m), 2.47-2.22 (4H, m), 1.98-1.80 (2H, m), 1.36 (9H, s). | 415 (M + H)$^+$ |

Example Compounds 156 to 166 produced by a method similar to that of Example 11 using corresponding raw materials are shown in Table 48 to Table 51.

TABLE 48

| Ex. | Structural formula | ¹H-NMR (CDCl₃) | ESI + APCI MS |
|---|---|---|---|
| 156 | 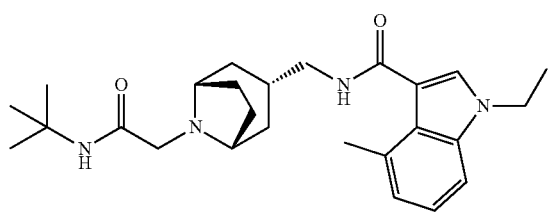 [SMILES: CCn1cc(C(=O)NC[C@@H]2C[C@H]3CC[C@@H](C2)N3CC(=O)NC(C)(C)C)c2c(C)cccc21] | δ: 7.42 (1H, br s), 7.40-7.36 (2H, m), 7.22-7.13 (2H, m), 7.00-6.93 (1H, m), 5.91-5.80 (1H, m), 4.15 (2H, q, J = 7.3 Hz), 3.32 (2H, dd, J = 6.5, 6.5 Hz), 3.19-3.08 (2H, m), 2.85 (2H, s), 2.68 (3H, s), 2.04-1.81 (3H, m), 1.70-1.54 (4H, m), 1.47 (3H, t, J = 7.3 Hz), 1.42-1.32 (2H, m), 1.37 (9H, s). | 439 (M + H)⁺ |
| 157 | 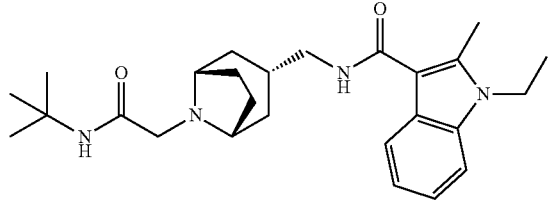 [SMILES: CCn1c(C)c(C(=O)NC[C@@H]2C[C@H]3CC[C@@H](C2)N3CC(=O)NC(C)(C)C)c2ccccc21] | δ: 7.69-7.63 (1H, m), 7.45 (1H, br s), 7.25-7.18 (3H, m), 6.02-5.94 (1H, m), 4.18 (2H, q, J = 7.3 Hz), 3.38 (2H, dd, J = 6.4, 6.4 Hz), 3.20-3.13 (2H, m), 2.86 (2H, s), 2.75 (3H, s), 2.09-1.82 (3H, m), 1.75-1.54 (4H, m), 1.51-1.40 (2H, m), 1.36 (3H, t, J = 7.3 Hz), 1.36 (9H, s). | 439 (M + H)⁺ |
| 158 | 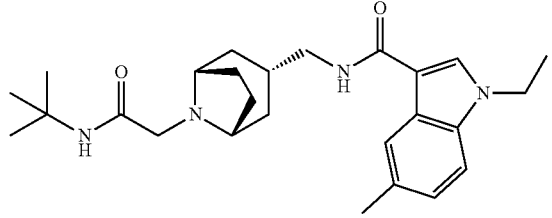 [SMILES: CCn1cc(C(=O)NC[C@@H]2C[C@H]3CC[C@@H](C2)N3CC(=O)NC(C)(C)C)c2cc(C)ccc21] | δ: 7.68-7.64 (1H, m), 7.68 (1H, s), 7.45 (1H, br s), 7.30-7.24 (1H, m), 7.13-7.08 (1H, m), 5.98-5.89 (1H, m), 4.17 (2H, q, J = 7.3 Hz), 3.37 (2H, dd, J = 6.3, 6.3 Hz), 3.18-3.11 (2H, m), 2.85 (2H, s), 2.50 (3H, s), 2.06-1.81 (3H, m), 1.73-1.53 (4H, m), 1.49 (3H, t, J = 7.3 Hz), 1.48-1.38 (2H, m), 1.35 (9H, s). | 439 (M + H)⁺ |

TABLE 49

| Ex. | Structural formula | ¹H-NMR (CDCl₃) | ESI + APCI MS |
|---|---|---|---|
| 159 | 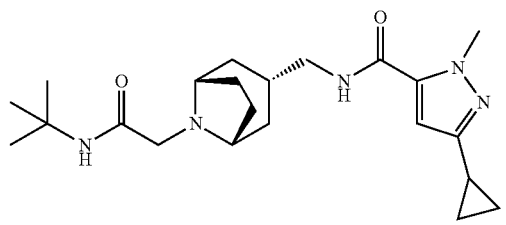 [SMILES: Cn1nc(C2CC2)cc1C(=O)NC[C@@H]1C[C@H]2CC[C@@H](C1)N2CC(=O)NC(C)(C)C] | δ: 7.39 (1H, br s), 6.11 (1H, s), 6.00-5.86 (1H, m), 4.08 (3H, s), 3.25 (2H, dd, J = 6.5, 6.5 Hz), 3.18-3.08 (2H, m), 2.85 (2H, s), 1.99-1.80 (4H, m), 1.69-1.51 (4H, m), 1.44-1.29 (2H, m), 1.37 (9H, s), 0.96-0.86 (2H, m), 0.74-0.65 (2H, m). | 402 (M + H)⁺ |
| 160 | 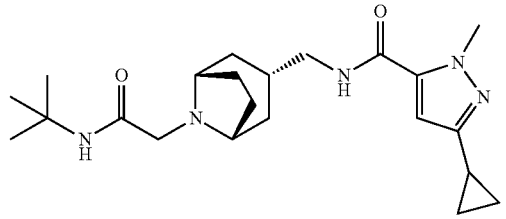 | 1H-NMR (CDCl3) δ: 7.38 (1H, br s), 6.73 (1H, s), 6.16-6.04 (1H, m), 4.22 (3H, s), 3.29 (2H, dd, J = 6.4, 6.4 Hz), 3.22-3.08 (2H, m), 2.86 (2H, s), 2.07-1.77 (3H, m), 1.71-1.50 (4H, m), 1.50-1.29 (2H, m), 1.37 (9H, s). | 430 (M + H)⁺ |

TABLE 49-continued

| Ex. | Structural formula | ¹H-NMR (CDCl₃) | ESI + APCI MS |
|---|---|---|---|
| 161 | | δ: 7.39 (1H, br s), 5.82-5.68 (1H, m), 4.09 (3H, s), 3.29 (2H, dd, J = 6.4, 6.4 Hz), 3.20-3.12 (2H, m), 2.86 (2H, s), 2.72-2.59 (4H, m), 2.01-1.86 (3H, m), 1.86-1.76 (4H, m), 1.71-1.52 (4H, m), 1.46-1.32 (2H, m), 1.37 (9H, s). | 416 (M + H)⁺ |
| 162 | | δ: 7.42 (1H, br s), 6.16-6.04 (1H, m), 3.26 (2H, dd, J = 6.5, 6.5 Hz), 3.18-3.10 (2H, m), 2.85 (2H, s), 2.43 (3H, s), 2.06-1.80 (4H, m), 1.68-1.48 (4H, m), 1.44-1.33 (2H, m), 1.36 (9H, s), 1.16-1.05 (4H, m). | 403 (M + H)⁺ |

TABLE 50

| Ex. | Structural formula | ¹H-NMR (CDCl₃) | ESI + APCI MS |
|---|---|---|---|
| 163 | | δ: 8.07 (1H, br s), 7.70-7.61 (1H, m), 7.40-7.18 (3H, m), 6.07-5.92 (1H, m), 3.71 (3H, s), 3.39 (2H, dd, J = 6.4, 6.4 Hz), 3.21-3.10 (2H, m), 2.96 (2H, s), 2.74 (3H, s), 2.09-1.85 (3H, m), 1.75-1.56 (4H, m), 1.54-1.41 (2H, m), 1.38-1.08 (4H, m). | 477 (M + H)⁺ |
| 164 | | δ: 8.06 (1H, br s), 7.70-7.61 (1H, m), 7.68 (1H, s), 7.31-7.24 (1H, m), 7.11 (1H, d, J = 8.2 Hz), 6.00-5.89 (1H, m), 4.17 (2H, q, J = 7.3 Hz), 3.38 (2H, dd, J = 6.4, 6.4 Hz), 3.19-3.08 (2H, m), 2.96 (2H, s), 2.50 (3H, s), 2.08-1.81 (3H, m), 1.73-1.54 (4H, m), 1.51-1.40 (2H, m), 1.49 (3H, t, J = 7.3 Hz), 1.37-1.09 (4H, m). | 491 (M + H)⁺ |
| 165 | | δ: 8.06 (1H, br s), 7.69-7.63 (1H, m), 7.40-7.33 (1H, m), 7.31-7.18 (2H, m), 6.04-5.93 (1H, m), 4.18 (2H, q, J = 7.3 Hz), 3.40 (2H, dd, J = 6.4, 6.4 Hz), 3.19-3.12 (2H, m), 2.96 (2H, s), 2.74 (3H, s), 2.07-1.86 (3H, m), 1.76-1.60 (4H, m), 1.53-1.42 (2H, m), 1.37-1.10 (4H, m), 1.36 (3H, t, J = 7.3 Hz). | 491 (M + H)⁺ |

TABLE 51

| Ex. | Structural formula | ¹H-NMR (CDCl₃) | ESI + APCI MS |
|---|---|---|---|
| 166 | 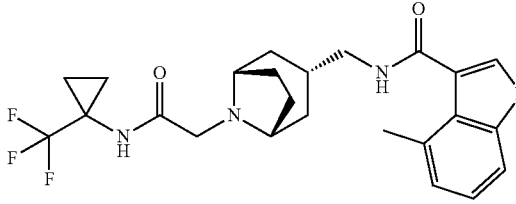 | δ: 8.04 (1H, br s), 7.39 (1H, s), 7.20-7.16 (2H, m), 7.00-6.94 (1H, m), 5.92-5.79 (1H, m), 4.16 (2H, q, J = 7.3 Hz), 3.34 (2H, dd, J = 6.6, 6.6 Hz), 3.20-3.10 (2H, m), 2.95 (2H, s), 2.68 (3H, s), 2.03-1.86 (3H, m), 1.71-1.54 (4H, m), 1.51-1.42 (2H, m), 1.47 (3H, t, J = 7.3 Hz), 1.37-1.08 (4H, m). | 491 (M + H)⁺ |

Example Compounds 167 to 171 produced by a method similar to that of Example 120 using corresponding raw materials are shown in Table 52.

TABLE 52

| Ex. | Structural formula | ¹H-NMR (CDCl₃) | ESI + APCI MS |
|---|---|---|---|
| 167 | 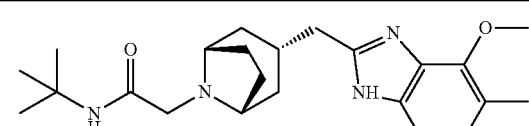 | δ: 9.03-8.83 (1H, m), 7.43 (1H, br s), 7.40-6.93 (2H, m), 4.26-3.87 (3H, m), 3.14-3.06 (2H, m), 2.85 (2H, s), 2.74 (2H, d, J = 7.1 Hz), 2.40-2.32 (3H, m), 2.30-2.11 (1H, m), 1.94-1.82 (2H, m), 1.64-1.53 (4H, m), 1.52-1.39 (2H, m), 1.37 (9H, s). | 399 (M + H)⁺ |
| 168 | 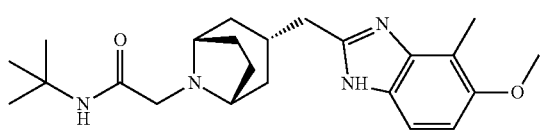 [SMILES: COc1ccc2[nH]c(C[C@@H]3C[C@H]4CC[C@@H](C3)N4CC(=O)NC(C)(C)C)nc2c1C] | δ: 9.02-8.84 (1H, m), 7.51-7.11 (1H, m), 7.43 (1H, br s), 6.88 (1H, d, J = 8.8 Hz), 3.88 (3H, s), 3.14-3.06 (2H, m), 2.85 (2H, s), 2.78-2.68 (2H, m), 2.57-2.31 (3H, m), 2.27-2.10 (1H, m), 1.92-1.82 (2H, m), 1.65-1.53 (4H, m), 1.50-1.39 (2H, m), 1.36 (9H, s). | 399 (M + H)⁺ |
| 169 | 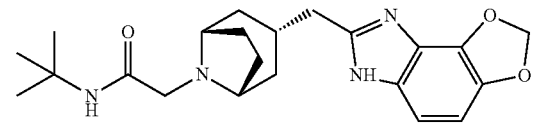 [SMILES: CC(C)(C)NC(=O)CN1[C@@H]2CC[C@H]1C[C@H](Cc1nc3c4c(ccc3[nH]1)OCO4)C2] | δ: 7.43 (1H, br s), 6.89-6.78 (2H, m), 6.04 (2H, s), 3.15-3.06 (2H, m), 2.86 (2H, s), 2.73 (2H, d, J = 8.1 Hz), 2.30-2.13 (1H, m), 1.96-1.82 (2H, m), 1.75-1.52 (4H, m), 1.52-1.39 (2H, m), 1.36 (9H, s). | 399 (M + H)⁺ |
| 170 | 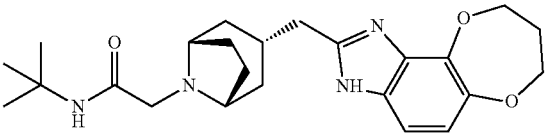 [SMILES: CC(C)(C)NC(=O)CN1[C@@H]2CC[C@H]1C[C@H](Cc1nc3c4c(ccc3[nH]1)OCCCO4)C2] | δ: 9.21-8.95 (1H, m), 7.43 (1H, br s), 7.32-6.83 (2H, m), 4.47-4.13 (4H, m), 3.16-3.03 (2H, m), 2.85 (2H, s), 2.73 (2H, d, J = 7.3 Hz), 2.31-2.14 (3H, m), 1.91-1.81 (2H, m), 1.70-1.16 (6H, m), 1.36 (9H, s). | — |
| 171 | 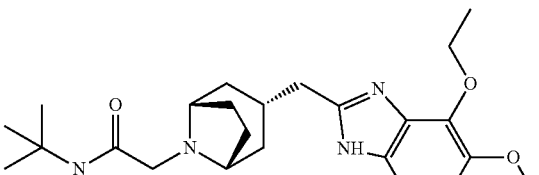 | δ: 8.96-8.93 (1H, m), 7.43 (1H, br s), 7.32 (1H, d, J = 8.8 Hz), 6.90 (1H, d, J = 8.8 Hz), 4.29 (2H, q, J = 7.0 Hz), 4.12 (2H, q, J = 7.0 Hz), 3.14-3.05 (2H, m), 2.85 (2H, s), 2.73 (2H, d, J = 7.3 Hz), 2.27-2.09 (1H, m), 1.95-1.80 (2H, m), 1.68-1.31 (6H, m), 1.44 (3H, t, J = 7.0 Hz), 1.41 (3H, t, J = 7.0 Hz), 1.36 (9H, s). | 443 (M + H)⁺ |

Example Compounds 172 and 173 produced by a method similar to that of Example 149 using corresponding raw materials are shown in Table 53.

10% (v/v) fetal bovine serum (FBS), penicillin (100 U/mL), streptomycin (100 μg/mL), and G418 (250 g/mL) had been added. The cells were suspended in the culture liquid and

TABLE 53

| Ex. | Structural formula | $^1$H-NMR (CD$_3$OD) | ESI + APCI MS |
|---|---|---|---|
| 172 | | δ: 7.89 (1H, s), 7.85 (1H, br s), 6.99 (2H, s), 6.60 (1H, s), 4.05-3.96 (2H, m), 4.00 (6H, s), 3.73 (2H, s), 3.14 (2H, d, J = 7.0 Hz), 2.67-2.47 (1H, m), 2.36-2.19 (2H, m), 2.13-1.99 (2H, m), 1.99-1.87 (4H, m), 1.35 (9H, s). | 415 (M + H)$^+$ |
| 173 | | δ: 7.84 (1H, br s), 6.79 (1H, d, J = 2.0 Hz), 6.70 (1H, d, J = 2.0 Hz), 4.06-3.99 (2H, m), 4.02 (3H, s), 3.88 (3H, s), 3.74-3.70 (2H, m), 3.12 (2H, d, J = 7.0 Hz), 2.63-2.50 (1H, m), 2.33-2.20 (2H, m), 2.13-2.01 (2H, m), 1.99-1.89 (4H, m), 1.36 (9H, s). | 415 (M + H)$^+$ |
| 174 | | δ: 6.84-6.90 (1H, m), 4.17 (3H, s), 3.94-4.05 (2H, m), 3.67-3.77 (2H, m), 3.24-3.38 (2H, m), 2.39 (3H, s), 2.16-2.33 (3H, m), 1.71-2.11 (6H, m), 1.36 (9H, s). | 376 (M + H)$^+$ |

Example 175

N-tert-Butyl-N'-{2-[(exo)-3-(5,6-dihydro-1H-[1,4]dioxino[2,3-e]benzimidazol-2-yl)methyl-8-azabicyclo[3.2.1]octan-8-yl]ethyl}urea

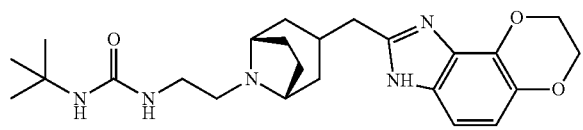 [SMILES: CC(C)(C)NC(=O)NCCN1[C@@H]2CC[C@H]1CC(Cc1nc3c4c(ccc3[nH]1)OCCO4)C2]

The title compound (40 mg) was obtained by a method similar to that of Example 123, using 2-[(exo)-8-azabicyclo[3.2.1]octan-3-yl]methyl-5,6-dihydro-1H-[1,4]dioxino[2,3-e]benzimidazole (122 mg)

$^1$H-NMR (CD$_3$OD)δ:6.91(1H,d,J=8.8 Hz),6.71(1H,d,J=8.8 Hz),4.32-4.37(2H,m),4.24-4.29(2H,m),3.22-3.27(2H,m),3.17(2H,t,J=6.8 Hz),2.68(2H,d,J=7.3 Hz),2.46(2H,t,J=6.8 Hz), 2.15-2.32(1H,m),1.90-2.00(2H,m),1.39-1.69(6H, m),1.28(9H,s).

ESI+APCI-MS Found:m/z 442 (M+H)+

Test Example 1

For representative compounds of the present invention, the antagonistic activity against T-type calcium channels (Cav3.2) was examined by the Test Examples described below. For the respective tests, human embryo kidney cells (HEK293 cells) in which human T-type calcium channels (human Cav3.2) were stably expressed were used.

The HEK293 cells having human Cav3.2 stably expressed therein were cultured at 37° C. in Alpha-MEM, to which were inoculated onto a 96-well plate. Subsequently, the cells were cultured for 48 hours. The culture liquid was removed, and the liquid was changed to S-MEM, to which 5% (v/v) FBS, calcium chloride (0.5 mmol/L), L-glutamine (2 mmol/L), L-alanine (8.9 ng/mL), L-asparagine (13.2 ng/mL), L-aspartic acid (1.33 ng/mL), L-glutamic acid (14.7 ng/mL), glycine (7.5 ng/mL), L-proline (11.5 ng/mL, L-serine (10.5 ng/mL), penicillin (100 U/mL), and streptomycin (100 μg/mL) had been added. The cells were cultured for another 24 hours. The culture liquid was removed again, and the cells were washed with an assay buffer (140 mmol/L sodium chloride, 5 mmol/L potassium chloride, 0.5 mmol/L magnesium chloride, 0.5 mmol/L calcium chloride, 10 mmol/L glucose, 0.4 mmol/L magnesium sulfate, 10 mmol/L HEPES, and 250 mol/L sulfinpyrazone, pH 7.4) that had been kept warm at 37° C. Subsequently, an assay buffer prepared by dissolving Fura2-AM, which is a fluorescent Ca$^{2+}$ indicator, to a concentration of 5 μM, was added to the cells, and the system was incubated for 30 minutes at 37° C. The assay buffer having Fura2 dissolved therein was removed, and the cells were washed with the assay buffer. Subsequently, an assay buffer prepared by adding a test compound was added to the cells, and the system was incubated for 15 minutes. The plate was mounted on a fluorescence analyzer (FLEX STATION II, Molecular Devices, LLC), and the baseline was measured for 20 seconds. Subsequently, any change in the intracellular calcium concentration that was induced when an assay buffer prepared by adding 100 mmol/L calcium chloride was added to the cells, was measured (excited at 340 nm or 380 nm, and detected at 510 nm). The fluorescence intensity ratios obtainable at the respective wavelengths were calculated.

Meanwhile, the test compound solution was prepared by dissolving each test compound in DMSO to a concentration of 10 mmol/L, and then adjusting the concentration with the assay buffer so as to obtain the set concentration. For the control solution, DMSO was used instead of a test compound.

The inhibitory activity level (%) of a test compound was calculated by subtracting the average value of the fluorescence intensity ratio for a period of 0 to 20 seconds after initiation of measurement, from the average value of the fluorescence intensity ratio for a period of 45 to 50 seconds after initiation of measurement, taking the value obtained using the control solution as the maximum activity of Cav3.2, and comparing this value with the activity in the presence of the test compound.

Calculation of IC$_{50}$ Value:

The inhibitory activity of each test compound was measured at concentrations of 0.3, 0.5, 1, 3, 5, 10, and 30 mol/L, and the IC$_{50}$ value was calculated using the curve fitting formula (Model 08: sigmoidal inhibition curve) of ASSAY EXPLORER (Symyx Technologies, Inc.).

Curve fitting formula (Model 08: Sigmoidal Inhibition Curve, Vmax+Y2 to Y2)

$$Y = V\max \times (1 - (X^n/(K^n + X^n))) + Y2$$

X=Concentration
Y=% inhibitory value
% inhibitory value=(RFU (compound)−RFU (LC))/(RFU (HC)−RFU (LC))

HC:
Average of RFU value obtained for 25 to 30 seconds after the addition of a Ca$^{2+}$-containing assay buffer after treatment with the control solution (for 45 to 50 seconds after the initiation of measurement)

LC:
Average of RFU value obtained for 25 to 30 seconds after the addition of a non-Ca$^{2+}$-containing assay buffer after treatment with the control solution (for 45 to 50 seconds after the initiation of measurement). The RFU in the formula represents the Relative Fluorescence Unit.

The test results are shown in Tables 54 and 55.

TABLE 54

| Example | IC$_{50}$ (μM) |
|---|---|
| 1 | 0.068 |
| 3 | 0.069 |
| 4 | 0.082 |
| 11 | 0.003 |
| 16 | 0.047 |
| 18 | 0.073 |
| 19 | 0.048 |
| 23 | 0.203 |
| 24 | 0.078 |
| 27 | 0.094 |
| 28 | 0.065 |
| 31 | 0.073 |
| 32 | 0.098 |
| 36 | 0.049 |
| 37 | 0.067 |
| 45 | 0.103 |
| 52 | 0.048 |
| 53 | 0.049 |
| 54 | 0.020 |
| 55 | 0.036 |
| 56 | 0.034 |
| 59 | 0.061 |
| 60 | 0.078 |
| 65 | 0.099 |
| 67 | 0.042 |
| 69 | 0.051 |
| 71 | 0.064 |
| 72 | 0.055 |
| 74 | 0.101 |
| 77 | 0.022 |
| 78 | 0.044 |
| 79 | 0.045 |

TABLE 54-continued

| Example | IC$_{50}$ (μM) |
|---|---|
| 81 | 0.093 |
| 84 | 0.010 |
| 85 | 0.015 |
| 86 | 0.091 |
| 95 | 0.088 |
| 96 | 0.058 |
| 100 | 0.085 |
| 104 | 0.013 |
| 107 | 0.049 |
| 109 | 0.094 |

TABLE 55

| Example | IC$_{50}$ (μM) |
|---|---|
| 112 | 0.093 |
| 113 | 0.039 |
| 114 | 0.070 |
| 115 | 0.063 |
| 118 | 0.078 |
| 120 | 0.059 |
| 122 | 0.138 |
| 124 | 0.096 |
| 127 | 0.073 |
| 129 | 0.066 |
| 131 | 0.049 |
| 144 | 0.044 |
| 145 | 0.098 |
| 147 | 0.083 |
| 154 | 0.078 |
| 160 | 0.049 |

The compounds of the present invention are highly safe in terms of, for example, genotoxicity risk, compared to those antagonists for T-type calcium channels having a piperidine structure. This will be shown by the Test Example described below.

Test Example 2

Reverse Mutation Test (Ames Test)

The presence or absence of genotoxicity in the compounds of the present invention was evaluated by a reverse mutation test (Ames test) using bacteria. The test was performed by a pre-incubation method using two bacterial strains of Salmonella typhimurium TA98 and TA100, in the absence of a metabolic activation system (S9mix (−)) and in the presence of a metabolic activation system (S9mix (+)). The compounds were dissolved in dimethyl sulfoxide (DMSO), and thus test liquids were prepared. Regarding the negative control, the solvent DMSO was used. Regarding the positive control, 2-(2-furyl)-3-(5-nitro-2-furyl)acrylamide (AF-2) was used for S9mix (−), and 2-aminoanthracene (2-AA) was used for S9mix (+).

0.1 mL of a test liquid was introduced into a sterilized test tube, and then 0.5 mL of a 0.1 mol/L sodium phosphate buffer solution (pH 7.4) was added to the test tube in the case of S9mix (−), or 0.5 mL of rat liver S9mix was added to the test tube in the case of S9mix (+). Furthermore, 0.1 mL of a precultured test strain suspension was added to the test tube, and then the test strain was subjected to shaking culture for 20 minutes at 37° C. (preincubation). After completion of the preincubation, 2 mL of TOP AGAR (soft agar containing histidine and biotin respectively at a concentration of 0.05 mM) was added thereto, and the content was mixed such that foaming did not occur. Subsequently, the content of the test tube was superposed on a minimum glucose agar medium plate and was spread evenly. The plate was cultured for 48 hours at 37° C. in a thermostat. After completion of culture, the number of reverse mutation colonies grown on the plate was measured using a colony counter. Regarding the determination, a case in which the number of reverse mutation colonies increased to twice or more of the number of colonies of the negative control, and concentration-dependency was recognized, was regarded as positive.

For comparison, Control compounds 1 to 3 having a piperidine structure were synthesized by the method described below, and the compounds were similarly evaluated by a genotoxicity test.

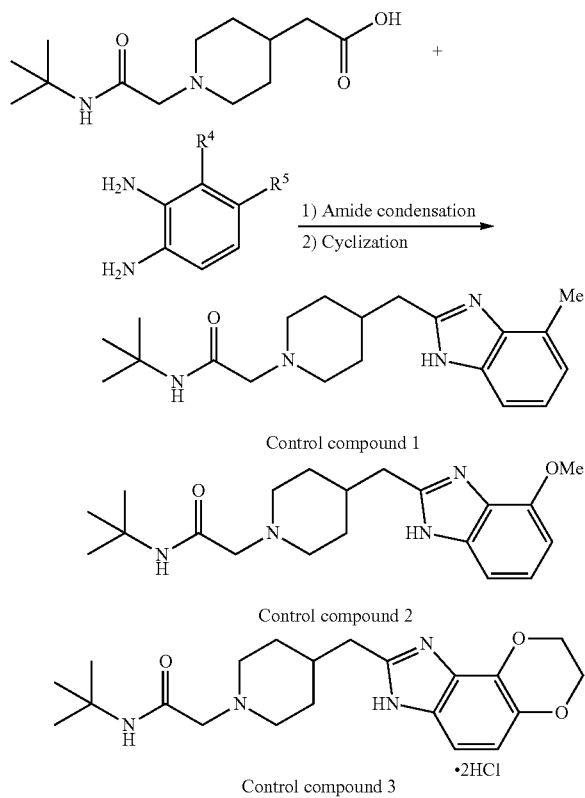

wherein $R^4$ and $R^5$ respectively mean the same as defined above.

Reference Example 30

N-tert-Butyl-2-[4-(4-methyl-1H-benzimidazol-2-yl)methylpiperidin-1-yl]acetamide (Control Compound 1)

[1-(tert-Butylcarbamoyl)methylpiperidin-4-yl]acetic acid hydrochloride (1.50 g) was suspended in acetonitrile (20 mL), and 2,3-diaminotoluene (657 mg) and PyBOP (2.93 g) were added thereto. Subsequently, triethylamine (3.03 mL) was added thereto, and the mixture was stirred for 5 hours at room temperature. The reaction solvent was distilled off under reduced pressure, water was added thereto, and extracted with ethyl acetate. The organic layer was washed with saturated brine and then was dried over anhydrous sodium sulfate, and the solvent was distilled off under reduced pressure. A residue thus obtained was purified by silica gel column chromatography (0% to 10% methanol/ethyl acetate), and a crude product was obtained.

The crude product thus obtained was dissolved in acetic acid (14 mL), and the solution was stirred for 4 hours under heating at 80° C. The reaction solvent was distilled off under reduced pressure, 1 mol/L hydrochloric acid was added to the residue, and the mixture was washed with chloroform. Subsequently, the aqueous layer was adjusted to pH 10 to 11 with a 2 mol/L aqueous solution of sodium hydroxide, and extracted with chloroform. The organic layer was washed with saturated brine and then was dried over anhydrous sodium sulfate, and the solvent was distilled off under reduced pressure. A residue thus obtained was purified by silica gel column chromatography (0% to 11% methanol/chloroform), to yield the title compound (1.25 g).

$^1$H-NMR (CDCl$_3$)δ: 7.37(1H,d,J=7.9 Hz),7.16-6.98(3H, m),2.86-2.70(6H,m),2.57(3H,s),2.12-1.98(2H,m),1.94-1.76 (H,m),1.73-1.58(2H,m),1.40-1.19(2H,m),1.35(9H,s).

ESI+APCI-MS Found:m/z 343 (M+H)+

Reference Example 31

N-tert-Butyl-2-[4-(4-methoxy-1H-benzimidazol-2-yl)methylpiperidin-1-yl]acetamide (Control Compound 2)

The title compound was obtained by a method similar to that of Reference Example 31, using corresponding raw materials.

$^1$H-NMR (CDCl$_3$)δ:7.23-7.00(3H,m),6.72-6.63(1H,m), 3.96(3H,s),2.84(2H,s),2.84-2.72(4H,m),2.14-2.02(2H,m), 1.98-1.78(1H,m),1.76-1.64(2H,m),1.42-1.24(2H,m),1.35 (9H,s).

ESI+APCI-MS Found:m/z 359 (M+H)+

Reference Example 32

N-tert-Butyl-2-[4-(5,6-dihydro-1H-[1,4]dioxino[2,3-e]benzimidazol-2-yl)methylpiperidin-1-yl]acetamide dihydrochloride (Control Compound 3)

The title compound (3.90 g) was obtained by a method similar to that of Example 149, using [1-(tert-butylcarbamoyl)methylpiperidin-4-yl]acetic acid hydrochloride (5.10 g) and 2,3-dihydrobenzo[1,4]dioxin-5,6-diamine dihydrochloride (4.37 g).

$^1$H-NMR (DMSO-d$_6$)δ:9.62 (1H,brs),8.24(1H,brs),7.15 (1H,d,J=9.2 Hz),6.98(1H,d,J=9.2 Hz), 4.46-4.30(4H,m), 3.76(2H,brs),3.43-2.88(6H,m),2.20-1.98(1H,m),1.85-1.48 (4H,m),1.27(9H,s).

ESI+APCI-MS Found:m/z 387 (M+H)+

The results thus obtained are shown in the following Table 56.

TABLE 56

|  | Ames test | |
| --- | --- | --- |
| Example | S9 (−) | S9 (+) |
| 54 | Negative | Negative |
| 123 | Negative | Negative |
| 145 | Negative | Negative |
| 152 | Negative | Negative |
| 155 | Negative | Negative |
| 172 | Negative | Negative |
| 174 | Negative | Negative |
| Control Compound 1 | Negative | Positive |
| Control Compound 2 | Negative | Positive |
| Control Compound 3 | Negative | Positive |

The invention claimed is:

1. A compound of formula (I), a pharmaceutically acceptable salt thereof, or a solvate thereof:

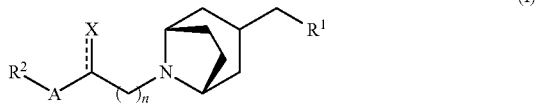

wherein $R^1$ represents —NH(C=O)—V—$R^3$, —(C=O)NH—V—$R^3$, or the following formula:

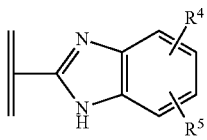

wherein V represents a single bond, methylene, or —C(CH$_3$)$_2$O—;

$R^3$ represents an optionally substituted C$_{3-6}$ alkyl group, a crosslinked cyclic hydrocarbon group, a fused polycyclic hydrocarbon group, an optionally substituted aryl group, or an optionally substituted heterocyclic group; and $R^4$ and $R^5$ are the same or different and independently represent a hydrogen atom, a halogen atom, a cyano group, an optionally substituted C$_{1-6}$ alkyl group, or an optionally substituted C$_{1-6}$ alkoxy group, or $R^4$ and $R^5$ are optionally linked together and form an optionally substituted non-aromatic heterocyclic ring;

$R^2$ represents an acyl group, an optionally substituted C$_{1-6}$ alkyl group, an optionally substituted aryl group, or an optionally substituted heterocyclic group;

X represents a hydrogen atom, an oxygen atom, a hydroxyl group, a methyl group, or a methylene group;

A represents —NR$^6$—, —NHCONH—, —O—CH$_2$—, or —S—CH$_2$—;

$R^6$ represents a hydrogen atom or an optionally substituted C$_{1-6}$ alkyl group, or $R^6$ and $R^2$ are optionally linked together and form an optionally substituted non-aromatic heterocyclic ring;

n represents the number of methylene groups and represents an integer of 0, 1 or 2; and a doublet containing a dotted line represents a single bond or a double bond; and when A is —O—CH$_2$— or —S—CH$_2$—, $R^2$ represents an optionally substituted aryl group or an optionally substituted heterocyclic group.

2. The compound of claim 1, a pharmaceutically acceptable salt thereof, or a solvate thereof, wherein V represents a single bond or methylene.

3. The compound of claim 1, a pharmaceutically acceptable salt thereof, or a solvate thereof, wherein V represents a single bond.

4. The compound of claim 1, a pharmaceutically acceptable salt thereof, or a solvate thereof, wherein $R^3$ represents a C$_{3-6}$ alkyl group, an adamantyl group, a noradamantyl group, an optionally substituted aryl group, or an optionally substituted heteroaryl group, wherein the aryl group or the heteroaryl group has one to three substituents selected from the group consisting of a linear or branched C$_{1-6}$ alkyl group, a C$_{3-6}$ cyclic alkyl group, a halogen atom, a cyano group, a hydroxy group, and a C$_{1-6}$ alkoxy group.

5. The compound of claim 1, a pharmaceutically acceptable salt thereof, or a solvate thereof, wherein $R^3$ represents an adamantyl group, a phenyl group, a benzofuranyl group, an indolyl group, a pyrazolyl group, an oxazolyl group, or a thiazolyl group, wherein the phenyl group or heteroaryl group has one to three substituents selected from the group consisting of a linear or branched. C$_{1-6}$ alkyl group, a C$_{3-6}$ cyclic alkyl group, a halogen atom, a cyano group, a hydroxy group, and a C$_{1-6}$ alkoxy group.

6. The compound of claim 1, a pharmaceutically acceptable salt thereof, or a solvate thereof, wherein $R^3$ represents an adamantyl group; an unsubstituted phenyl group or a phenyl group substituted with one or two of a halogen atom, a methyl group, an ethyl group, a cyclopropyl group, a methoxy group or a cyano group; an unsubstituted benzofuranyl group or a benzofuranyl group substituted with one or two of a halogen atom, a methyl group, an ethyl group, a cyclopropyl group, a methoxy group or a cyano group; an unsubstituted indolyl group or an indolyl group substituted with one or two of a halogen atom, a methyl group, an ethyl group, a cyclopropyl group, a methoxy group or a cyano group; an unsubstituted pyrazolyl group or a pyrazolyl group substituted with one or two of a halogen atom, a methyl group, an ethyl group, a cyclopropyl group, a methoxy group or a cyano group; an unsubstituted oxazolyl group or an oxazolyl group substituted with one or two of a halogen atom, a methyl group, an ethyl group, a cyclopropyl group, a methoxy group or a cyano group; or an unsubstituted thiazolyl group or a thiazolyl group substituted with one or two of a halogen atom, a methyl group, an ethyl group, a cyclopropyl group, a methoxy group or a cyano group.

7. The compound of claim 1, a pharmaceutically acceptable salt thereof, or a solvate thereof, wherein $R^2$ represents a linear or branched C$_{1-6}$ alkyl group optionally substituted with one to three substituents selected from the group consisting of a halogen atom, a cyano group, a hydroxy group and a C$_{1-6}$ alkoxy group; or a cyclic C$_{3-6}$ alkyl group optionally substituted with one to three substituents selected from the group consisting of a halogen atom, a cyano group, a hydroxy group and a C$_{1-6}$ alkoxy group.

8. The compound of claim 1, a pharmaceutically acceptable salt thereof, or a solvate thereof, wherein X represents an oxygen atom.

9. The compound of claim 1, a pharmaceutically acceptable salt thereof, or a solvate thereof, wherein A represents —NR$^6$—, and R$^6$ represents a hydrogen atom or a methyl group.

10. The compound of claim 1, a pharmaceutically acceptable salt thereof, or a solvate thereof, wherein n is 1.

11. A pharmaceutical composition, comprising:
the compound of claim 1, a pharmaceutically acceptable salt thereof, or a solvate thereof; and
a pharmaceutically acceptable carrier.

12. The pharmaceutical composition of claim 11, wherein the pharmaceutically acceptable carrier is at least one selected from the group consisting of an excipient, a binder, a buffer agent, a thickening agent, a stabilizer, an emulsifier, a dispersant, a suspending agent, and an antiseptic agent, a disintegrant, a lubricating agent, a dissolution aid, a solubilizing agent, a pH adjusting agent, and an isotonizing agent.

13. A method for treating a disease or condition in which T-type calcium channel is involved, comprising:
administering an effective amount of the compound of claim 1 or a pharmaceutically acceptable salt thereof,
wherein the disease is at least one selected from the group consisting of hypertension, atrial fibrillation, arrhythmia, cardiac hypertrophy, cardiac failure, renal dysfunction, pain, epilepsy, sleep disorder, obesity, and cancer.

* * * * *